US007563612B2

(12) United States Patent
Saxena et al.

(10) Patent No.: US 7,563,612 B2
(45) Date of Patent: Jul. 21, 2009

(54) RECOMBINANT BIFUNCTIONAL PROTEIN OF HUMAN LUTROPIN RECEPTOR AND HUMAN CHORIONIC GONADOTROPIN B-SUBUNIT AND USES THEREOF

(75) Inventors: Brij B. Saxena, Englewood, NJ (US); Premila Rathnam, Englewood Cliffs, NJ (US); Makul Singh, Teaneck, NJ (US); Meirong Hao, Rego Park, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 152 days.

(21) Appl. No.: 11/235,621

(22) Filed: Sep. 26, 2005

(65) Prior Publication Data

US 2006/0073571 A1 Apr. 6, 2006

Related U.S. Application Data

(60) Provisional application No. 60/613,246, filed on Sep. 27, 2004.

(51) Int. Cl.

| | |
|---|---|
| ***C12N 1/19*** | (2006.01) |
| ***C12N 1/21*** | (2006.01) |
| ***C12N 5/16*** | (2006.01) |
| ***C12N 15/62*** | (2006.01) |
| ***C12N 15/63*** | (2006.01) |
| ***A61K 38/24*** | (2006.01) |

(52) U.S. Cl. .............. 435/252.3; 435/69.1; 435/254.11; 435/320.1; 435/69.7; 435/69.4; 435/325; 435/348; 435/350; 435/351; 536/23.1; 536/23.5

(58) Field of Classification Search ....................... None
See application file for complete search history.

(56) References Cited

U.S. PATENT DOCUMENTS

| | | | |
|---|---|---|---|
| 4,237,224 | A | 12/1980 | Cohen et al. |
| 4,458,066 | A | 7/1984 | Caruthers et al. |
| 4,873,192 | A | 10/1989 | Kunkel |
| 5,491,084 | A | 2/1996 | Chalfie et al. |
| 6,723,556 | B1 | 4/2004 | Saxena et al. |

FOREIGN PATENT DOCUMENTS

| | | |
|---|---|---|
| WO | WO 97/49432 | * 12/1997 |

OTHER PUBLICATIONS

Narayan et al., Endocrinol. 2000; 141: 67-71.*

Puett et al., Indian Journal of Experimental Biol. 2002; 40: 415-423.*

Akman et al., "The Development of an Enzymeimmunometric Assay for LH and the Effects of the Methods on the Immunoreactivity of the Conjugates," *J Immunoassay Immunochem* 19(2&3), 113-128 (1998).

Altschul et al., "Gapped BLAST and PSI-BLAST: A New Generation of Protein Database Search Programs," *Nucleic Acids Res.* 25:3389-3402 (1997).

Alvarez et al., "Characterization of a Region of the Lutropin Receptor Extracellular Domain Near Transmembrane Helix 1 That is Important in Ligand-Mediated Signaling," *Endocrinilogy* 140(4):1775-82 (1999).

Ascoli et al., The Lutropin/Choriogonadotropin Receptor, A 2002 Perspective, *Endocr Rev* 23(2):141-174 (2002).

Bhowmick et al., "Identification of Ionizable Amino Acid Residues on the Extracellular Domain of the Lutropin Receptor Involved in Ligand Binding," Endocrinology 140(10): 4558-4563 (1999).

Bukovsky et al., "Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disease," *Reprod Biol Endocrinol* 1:46 (2003).

Campbell et al., "Conversion of Human Choriogonadotropin Into a Follitropin by Protein Engineering," *Proc. Natl Acad Sci USA* 88(3):760-764 (1991).

Damas Rocha et al., "Recombinant Viruses as Tools to Induce Protective Cellular Immunity Against Infectious Diseases," *Int Microbiol* 7(2):83-94 (2004).

Fraley et al., "Liposome-Mediated Delivery of Tobacco Mosaic Virus RNA Into Tobacco Protoplasts: A Sensitive Assay for Monitoring Liposome-Protoplast Interactions," *Proc Natl Acad Sci USA* 79:1859-63 (1982).

Fralish et al., "Structural Analysis of Yoked Chorionic Gonadotropin-Luteinizing Hormone Receptor Ectodomain Complexes by Circular Dichroic Spectroscopy," *Mol Endocrinol* 17(7):1192-1202 (2003).

Garcia-Carrancá, A., "Vaccines Against Human Papillomavirus and Perspectives for the Prevention and Control of Cervical Cancer," *Salud Publica Mex* 45(Suppl 3):S437-442 (2003).

Garmory et al., "DNA Vaccines: Improving Expression of Antigens," *Genetic Vaccines and Therapy* 1(1):2 (2003).

(Continued)

*Primary Examiner*—Bridget E Bunner
*Assistant Examiner*—Christina Borgeest
(74) *Attorney, Agent, or Firm*—Nixon Peabody LLP

(57) ABSTRACT

The present invention relates to a chimeric nucleic acid molecule encoding a fusion protein having a human lutropin hormone-receptor domain and a human chorionic gonadotropin-β subunit domain, the isolated human lutropin hormone-receptor/human chorionic gonadotropin-β fusion protein, and antibodies which recognize part or all the domains of the fusion protein. Also provided are compositions having the human lutropin hormone-receptor/human chorionic gonadotropin-β fusion protein and a pharmaceutical carrier and compositions including antibodies to the fusion protein and a pharmaceutical carrier. The present invention also relates to methods of treating androgen-excess-mediated disease conditions by administering to a subject an antibody to the human lutropin hormone-receptor/human chorionic gonadotropin-β fusion protein under conditions suitable to treat the conditions, and methods of immunocontraception that involve administering to a subject the chimeric nucleic acid molecule encoding the human lutropin hormone receptor/human chorionic gonadotropin-β fusion protein, the fusion protein in whole or in part, or antibodies thereto.

12 Claims, 15 Drawing Sheets

OTHER PUBLICATIONS

Hao and Saxena, "Bifunctional Recombinant Protein Expressed by Chimeric Human Lutropin Receptor & Chorionic Gonadotropin Beta-Subunit Fragments as Potential Contraceptive Antigen in Vertebrates," *Presentation at SSR 37th Annual Meeting*, Aug. 1-4, 2004.

Hao et al., "Expression of A Recombinant Bifunctional Protein from a Chimera of Human Lutropin Receptor and Human Chorionic Gonadotropin β-Subunit," *Journal of Reproductive Immunology* 63:123-135 (2004).

Jeyakumar et al., "Demonstration of Complimentarity Between Monoclonal Antibodies (Mabs) to Human Chorionic Gonadotropin (Hcg)and Polyclonal Antibodies to Luteinizing Hormone/Hcg Receptor (LH-R) and Their Use in Better Understanding Hormone-Receptor Interaction," *Recept Signal Transduct* 7(4):299-310 (1997).

Jones, "Vaccination for Contraception," *Aust NƵ J Obstet Gynaecol* 34:3:320 (1994).

Karlin and Altschul, "Applications and Statistics for Multiple High-Scoring Segments in Molecular Sequences," *Proc. Natl. Acad. Sci. USA* 90(12):5873-5877 (1993).

Karlin and Altschul, "Methods for Assessing the Statistical Significance of Molecular Sequence Features by Using General Scoring Schemes," *Proc. Natl. Acad. Sci. USA* 87(6): 2264-2268 (1990).

Khan et al., "Purification and Properties of Human Chorionic Gonadotropin/Lutropin Receptor from Plasma-Membrane and Soluble Fractions of Bovine Corpora Lutea," *Biochem J* 197(1):7-22 (1981).

Köhler and Milstein, "Continuous Cultures of Fused Cells Secreting Antibody of Predefined Specificity," *Nature* 256(5517):495-497 (1975).

Kunkel, T.A., Rapid and Efficient Site-Specific Mutagenesis Without Phenotypic Selection, *Proc Natl Acad Sci USA* 82(2):488-492 (1985).

Manoj et al., "Approaches to Enhance the Efficacy of DNA Vaccines," *Crit Rev Clin Lab Sci* 41(1):1-39 (2004).

Minegishi et al., "Cloning and Sequencing of Human LH/hCG Receptor cDNA," *Biochem Biophys Res Commun* 201:1057 (1994).

Moudgal et al., "Development of Male Contraceptive Vaccine—A Perspective," *Hum Reprod Update* 3(4):335-46 (1997).

Nagayama et al., "Binding Domains of Stimulatory and Inhibitory Thyrotropin (TSH) Receptor Autoantibodies Determined With Chimeric TSH-Lutropin/Chorionic Gonadotropin Receptors," *J Clin Invest* 88(1):336-40 (1991).

Narayan et al., "Expression of Functional Lutropin/Choriogonadotropin Receptor in the Baculovirus System," *Mol Cell Endocrinol* 117(1):95-100 (1996).

Narayan et al., "Yoked Complexes of Human Choriogonadotropin and the Lutropin Receptor: Evidence that Monomeric Individual Subunits are Inactive," *Mol Endocrinol* 16(12):2733-2745 (2002).

Needham-Vandevanter et al., "Characterization of an Adduct Between CC-1065 and a Defined Oligodeoxynucleotide Duplex," *Nucleic Acids Res* 12(15):6159-6168 (1984).

Neumann et al., "Gene Transfer into Mouse Lyoma Cells by Electroporation in High Electric Fields," *EMBO J.* 1:841-45 (1982).

Paukku et al., "Persistance of Biological Activity of Biotinylated Human Chorionic Gonadotropin and its Use for Visualization of Rat Luteinizing Hormone Receptors in Tissue Sections," *J Histochem Cytochem* 46(9):993-998 (1998).

Pearson and Lipman, "Improved tools for biological sequence comparison," *Proc Natl Acad Sci USA* 85:2444-8 (1988).

Pierce and Parsons, "Glycoprotein Hormones: Structure and Function," *Ann Rev Biochem* 50:465-95 (1981).

Potter et al., "Enhancer-Dependent Expression of Human Kappa Immunoglobulin Genes Introduced into Mouse pre-B Lymphocytes by Electroporation," *Proc. Natl. Acad. Sci. USA* 81:7161-65 (1984).

Sugahara et al., "Biosynthesis of a Biologically Active Single Chain Containing the Human Common α and Chorionic Gonadotropin β Subunits in Tandem," *Proc Natl Acad Sci USA* 92:2041-2045 (1995).

Rajagopalan-Gupta, et al., "Luteinizing hormone/choriogonadotropin-dependent, cholera toxin-catalyzed adenosine 5'-diphosphate (ADP)-ribosylation of the long and short forms of Gs alpha and pertussis toxin-catalyzed ADP-ribosylation of Gi alpha," *Mol Endocrinol* (5):538-49 (1997).

Rao, "Is there a Role for Contraceptive Vaccines in Fertility Control?" *J Biosci* 26(4 Suppl): 425-7 (2001).

Rathnam and Saxena, "Subunits of Luteinizing Hormone from Human Pituitary Glands," *J Biol Chem* 246(23):7087-94 (1971).

Saxena and Rathnam, "Dissociation Phenomenon and Subunit Nature of Follicle-stimulating Hormone from Human Pituitary Glands," *J Biol Chem* 246(11):3549-3554 (1971).

Stevens, "Progress in the Development of Human Chorionic Gonadotropin Antifertility Vaccines," *Am J Reprod Immunol* 35(3):148-55 (1996).

Talwar et al., "A Vaccine that Prevents Pregnancy in Women," *Proc Natl Acad Sci U S A* 91(18):8532-6 (1994).

Talwar, "Fertility Regulating and Immunotherapeutic Vaccines Reaching Human Trials Stage," *Hum Reprod Update* 3(4):301-10 (1997).

Wolchok et al., "DNA Vaccines: An Active Immunization Strategy for Prostate Cancer," *Semin Oncol* 30(5):659-666 (2003).

Wu et al., "Protein Engineering of Novel Constitutively Active Hormone-Receptor Complex," *J Biol Chem* 271:31638-31642 (1996).

Xie et al., "Extracellular Domain of Lutropin/Choriogonadotropin Receptor Expressed in Transfected Cells Binds Choriogonadotropin with High Affinity," *J Biol Chem* 265(35):21411-21414 (1990).

Xu and Ulmer, "Attenuated Salmonella and Shigella as Carriers for DNA Vaccines," *J. Drug Target* 11(8-10):481-488 (2003).

Abraham et al., "Simultaneous Radioimmunoassay of Plasma FSH, LH, Progesterone, 17-Hydroxyprogesterone, and Estradiol-17β During the Menstrual Cycle," The Division of Reproductive Biology, Department of Obstetrics and Gynecology, and the Division of Endocrinology, Department of Medicine, Harbor General Hospital, Torrance, CA pp. 312-318 (1971).

Atger et al.., "Structure of the Human Luteinizing Hormone-choriogonadotropin Receptor Gene: Unusual Promoter and 5' Non-coding Regions," *Molecular and Cellular Endocrinology* 111:113-23 (1995).

Chen et al., "Needle-free Epidermal Powder Immunization," *Expert Rev. Vaccines* 1(3):265-76 (2002).

Choi et al., "Topical Vaccination of DNA Antigens: Topical Delivery of DNA Antigens," *Skin Pharmacol Appl Skin Physiol* 16:271-82 (2003).

Christenson et al., "Maturation of Ovarian Follicles in the Prepubertal Gilt," *J. Reprod. Fert.* 33:21-36 (1985).

Garcia-Carrancá, "Vaccines Against Human Papillomavirus and Perspectives for the Prevention and Control of Cervical Cancer," *Salud Publica de México* 45(3):S437-42 (2003).

Gupta et al., "Contraceptive Vaccines," National Institute of Immunology, New Delhi, India vol. 10 pp. 255-265 (1994).

Haynes et al., "Particle-mediated DNA Vaccine Delivery to the Skin," *Expert. Opin. Biol. Ther.* 4(6):889-900 (2004).

Hobson et al., "Mucosal Immunization with DNA Vaccines," *Science Direct* 31:217-224 (2003).

Igarashi et al., Functional Expression of Recombinanat Human Luteinizing Hormone/Human Choriogonadotropin Receptor, *Biochemical and Biophysical Research Communications* 201(1):248-56 (1994).

Ji et al., "Exons 1-10 of the Rat LH Receptor Encode a High Affinity Hormone Binding Site and Exon 11 Encodes G-Protein Modulation and a Potential Second Hormone Binding Site," *Endocrinology* 128(5):2648-50 (1991).

Köhler et al., "Continuous Cultures of Fused Cells Secreting Antibody of Predefined Specificity," *Nature* 256:495-7 (1975).

Köhler et al., "Derivation of Specific Antibody-producing tissue Culture and Tumor Lines by Cell Fusion," *Eur. J. Immunol.* 6:511-9 (1976).

Leung et al., "Interactions of Steroids and Gonadotropins in the Control of Steroidogenesis in the Ovarian Follicle," *Ann. Rev. P)hysiol.* 42:71-82 (1980).

Lobel et al., "Expression and Characterization of Recominant β-subunit hCG Homodimer," *Endocrine* 10(3):261-70 (1999).

McFarland et al., "Lutropin-Choriogonadotropin Receptor: An Unusual Member of the G Protein-Coupled Receptor Family," *Science* 245:494-9 (1989).

Minegishi et al., "Cloning and Sequencing of Human FSH Receptor cDNA," *Biochemical and Biophysical Research Communications* 175(3):1125-30 (1991).
Pal et al., "Active Immunization of Baboons (*Papio Anubis*) with the Bovine LH Receptor," *Journal of Reproductive Immunology* 21:163-74 (1992).
Pal et al., "Biological Actions of Monoclonal Antibodies to Bovine Lutropin Receptor," *Journal of Reproductive Immunology* 22:87-103 (1992).
Rathnam et al., "Conjugation of a Fetuin Glycopeptide to Human Follicle-Stimulating Hormone and its Subunits by Photoactivation," *Biochimica et Biophysica Acta* 624:436-442 (1980).
Remy et al., "Immunization Against Exon 1 Decapeptides From the Lutropin/Choriogonadotropin Receptor or the Follitropin Receptor as Potential Male Contraceptive," *Journal of Reproduction Immunology* 32:37-54 (1996).
Ross et al., "Clinical Relevance of Research on the Structure of Human Chorionic Gonadotropin," *Am. J. Obstet. Gynecol.* 129(7):795-805 (1977).
Sasaki et al., "Adjuvant Formulations and Delivery Systems for DNA Vaccines," *Methods* 31:243-54 (2003).
Saxena et al., "Effect of Immunization with Bovine Luteinizing Hormone Receptor on Ovarian Function in Cats," *AJVR* 64(3):292-8 (2003).
Saxena et al., "Modulation of Ovarian Function in Female Dogs Immunized with Bovine Luteinizing Hormone Receptor," *Reprod Domest Anim* 37(1)1-17 (2002).
Saxena et al., "New Approaches in Fertility Regulation," *Journal of Obstetrics and Gynaecology* 4(1):S16-S22 (1984).
Saxena, "Measurement and Clinical Significance of Preimplantation Blastocyst Gonadotrophins," *J. Reprod. Fert.* 37:115-9 (1989).
Sheu et al., "The Gene Pill and its Therapeutic Applications," *Current Opinion in Molecular Therapeutics* 5(4):420-7 (2003).
Singh et al., "Effect of Immunization with Lutropin-Receptor on the Ovarian Function of Rabbits," *Journal of Immunoassay* 16(1):1-16 (1995).
Vaitukaitis et al., "Gonadotropins and Their Subunits: Basic and Clinical Studies," Thorndike Memorial Laboratory, Section of Endocrinology and Metabolism, Boston City Hospital, and Department of Medicine, Boston University School of Medicine, Boston Massachusetts, and Reproduction Research Branch, National Institute of Child Health and Human Development, National Institutes of Health, Bethesda, Maryland pp. 289-321 (1976).
Wolchok et la., "DNA Vaccines: An Active Immunization Strategy for Prostate Cancer," *Seminars in Oncology* 30(5):659-66 (2003).
Wong et al., "Electric Field Mediated Gene Transfer," *Biochemical and Biophysical Research Communications* 107(2):584-7 (1982).
Xu et al., "Attenuated *Salmonella* and *Shigella* as Carriers for DNA Vaccines," *Journal of Drug Targeting* 11(8-10):481-8 (2003).
Cole et al., "The Structures of the Serine-linked Sugar Chains on Human Chorionic Gonadotropin," Biochemical and Biophysical Research Communications 126(1):333-339 (1985).
Altschul et al., "Basic Local Alignment Search Tool," J. Mol. Biol. 215:403-410 (1990).
Arnon et al., "Old and New Vaccine Approaches," International Immunopharmacology 3:1195-1204 (2003).
Atger et al., "Structure of the Human Luteinizing Hormone-choriogonadotropin Receptor Gene: Unusual Promoter and 5' Non-coding Regions," Molecular and Cellular Endocrinology 111:113-123 (1995).
Brown et al., "Chemical Synthesis and Cloning of a Tyrosine tRNA Gene," Methods in Enzymology 68:109-151 (1979).
Heikoop et al., "Evaluation of Subunit Truncation and the Nature of the Spacer for Single Chain Human Gonadotropins," Eur. J. Biochem. 245:656-662 (1997).
Dattatreyamurty et al., "Isolation of the Luteinizing Hormone-chorionic Gonadotropin Receptor in High Yield from Bovine Corpora Lutea," 258(5):3140-3158 (1983).
Garmory et al., "DNA Vaccines: Improving Expression of Antigens," Genetic Vaccines and Therapy 1:1-5 (2003).
Hao et al., "Expression of a Recombinant Bifunctional Protein from a Chimera of Human Lutropin Receptor and Human Chorionic Gonadotropin Beta-subunit," Journal of Reproductive Immunology 63:123-135 (2004).
Heikoop et al., "Structure-based Design and Protein Engineering of Intersubunit Disulfide Bonds in Gonadotropins," 15:658-662 (1997).

* cited by examiner

RECOMBINANT BIFUNCTIONAL PROTEIN OF HUMAN LUTROPIN RECEPTOR AND HUMAN CHORIONIC GONADOTROPIN B-SUBUNIT AND USES THEREOF

This application claims the benefit of U.S. Provisional Patent Application Ser. No. 60/613,246, filed Sep. 27, 2004.

The subject matter of this application was made with support from the United States Government under The National Institutes of Health, Grant No. 1 R01 HD37109-01A1. The U.S. Government may have certain rights.

FIELD OF THE INVENTION

The present invention relates to a chimeric nucleic acid molecule encoding a human lutropin hormone receptor/human chorionic gonadotropin-β fusion protein, an expressed recombinant human lutropin hormone receptor/human chorionic gonadotropin-β fusion protein, antibodies to the protein, and uses thereof.

BACKGROUND OF THE INVENTION

Pituitary lutropin hormone (LH) is suppressed during the luteal phase of the menstrual cycle by negative feedback from ovarian steroids (Leung et al., "Interactions of Steroids and Gonadotropins in the Control of Steroidogenesis in the Ovarian Follicle," *Annu Rev Physiol* 42:71-82 (1980); Christenson et al., "Maturation of Ovarian Follicles in the Prepubertal Gilt," *J Reprod Fertil Suppl* 33:21-36 (1985) and Abraham et al., "Simultaneous Radioimmunoassay of Plasma FSH, LH, Progesterone, 17-Hydroxyprogesterone, and Estradiol-17beta During the Menstrual Cycle," *J Clin Endocrinol* 34:312-318 (1972)). Human chorionic gonadotropin (hCG), a placental hormone produced in the female at the time of implantation, provides a backup for pituitary LH to rescue the corpus luteum of pregnancy. hCG is a heterodimeric glycoprotein hormone consisting of an α and a β subunit that stimulates intracellular levels of cAMP via a G-protein-coupled receptor. A distinct feature of the hCG-β subunit is the presence of a C-terminal extension (CTP) of 24 amino acids, which produce specific antibodies to hCG-β with little cross-reaction with LH. In a gonadal cell, hCG binds to its cell surface receptor (LH/CG-R), resulting in an increase in the concentration of intracellular cAMP (Wu et al., "Protein Engineering of Novel Constitutively Active Hormone-Receptor Complex," *J Biol Chem* 271:31638-31642 (1996). hCG and hLH (human LH) are identical in structure except for the CTP of the β-subunit of hCG, which is highly glycosylated and has three serine-linked carbohydrate moieties (Cole et al., "The Structures of the Serine-Linked Sugar Chains on Human Chorionic Gonadotropin," *Biochem Biophys Res Commun* 126 (1):333-339 (1985)). hLH and hCG, by virtue of their structural similarity, bind to the same lutropin receptor (LH-R) in the gonads. The LH-R is also a member of the G protein-coupled receptor (GPCR) family and contains a relatively large, highly glycosylated, N-terminal extracellular domain (ECD) known for high affinity ligand binding (Xie et al., "Extracellular Domain of Lutropin/Choriogonadotropin Receptor Expressed in Transfected Cells Binds Choriogonadotropin with High Affinity," *J Biol Chem* 265(35):21411-21414 (1990) and Ji et al., "Exons 1-10 of the Rat LH Receptor Encode a High Affinity Hormone Binding Site and Exon 11 Encodes G-Protein Modulation and a Potential Second Hormone Binding Site," *Endocrinology* 128:2648-2650 (1991)), a seven-transmembrane domain, and a short intracellular cytoplasmic tail (McFarland et al., "Lutropin-Choriogonadotropin Receptor: An Unusual Member of the G Protein-Coupled Receptor Family," *Science* 245 (4917):494-499 (1989)). The extracellular domain is characterized by a motif of imperfect leucine-rich repeats, which contributes largely to the high affinity hormone binding of the receptor (Xie et al., "Extracellular Domain of Lutropin/Choriogonadotropin Receptor Expressed in Transfected Cells Binds Choriogonadotropin with High Affinity," *J Biol Chem* 265(35):21411-21414 (1990)). cDNAs of LH receptor have considerable interspecies homology among vertebrates (Ascoli et al., The Lutropin/Choriogonadotropin Receptor, A 2002 Perspective," *Endocr Rev* 23(2):141-174 (2002)). hLH-R and hCG-β are also antigenic at the interspecies level (Ascoli et al., The Lutropin/Choriogonadotropin Receptor, A 2002 Perspective," *Endocr Rev* 23(2):141-174 (2002); Pal et al., "Active Immunization of Baboons (*Papio anubis*) with the Bovine LH Receptor," *J Reprod Immunol* 21(2):163-174 (1992); Pal et al., "Biological Actions of Monoclonal Antibodies to Bovine Lutropin Receptor," *J Reprod Immunol* 22(1):103 (1992); Remy et al., "Immunization Against Exon 1 Decapeptides From the Lutropin/Choriogonadotropin Receptor or the Follitropin Receptor as Potential Male Contraceptive," *J Reprod Immunol* 32(1):37-54 (1996); Singh et al., "Effect of Immunization with Lutropin-Receptor on the Ovarian Function of Rabbits," *J Immunoassay* 16(1):1-16 (1995), Vaitukaitis et al., "A Radioimmunoassay Which Specifically Measures Human Chorionic Gonadotropin in the Presence of Human Luteinizing Hormone," *Am J Obstet Gynecol* 113(6):751-758 (1972)). Hence, hLH-R and hCG, and their functional epitopes, provide vital targets to be manipulated by genetic engineering to produce unique anti-fertility antigens.

Efficacies of antibodies to the hLH-R and hCG-β individually have been amply demonstrated in the regulation of gonadal function. There are a number of reports that qualify LH-R as a potential anti-fertility antigen (Remy et al., "Immunization Against Exon 1 Decapeptides From the Lutropin/Choriogonadotropin Receptor or the Follitropin Receptor as Potential Male Contraceptive," *J Reprod Immunol* 32(1):37-54 (1996); Saxena et al., "Modulation of Ovarian Function in Female Dogs Immunized With Bovine Luteinizing Hormone Receptor," *Reprod Domest Anim* 37(1): 9-17 (2002), and Saxena et al., "Effect of Immunization with Bovine Luteinizing Hormone Receptor on Ovarian Function in Cats," *Am J Vet Res* 64(3):292-298 (2003)). The injection of the recombinant mouse LH-R with hormone binding region to male mice induced immunity against the receptor. The data indicated that the specific anti-gonadotropin receptor vaccination could potentially be used as a fertility control procedure in males (Remy et al., "Immunization Against Exon 1 Decapeptides From the Lutropin/Choriogonadotropin Receptor or the Follitropin Receptor as Potential Male Contraceptive," *J Reprod Immunol* 32(l):37-54 (1996)). Previous studies showed that actively immunizing female dogs and cats with highly purified bovine LH-R can produce antibodies to the LH-R, which suppresses progesterone synthesis due to the blockade of the gonadal receptor (Saxena et al., "Modulation of Ovarian Function in Female Dogs Immunized With Bovine Luteinizing Hormone Receptor," *Reprod Domest Anim* 37(1):9-17 (2002) and Saxena et al., "Effect of Immunization with Bovine Luteinizing Hormone Receptor on Ovarian Function in Cats," *Am J Vet Res* 64(3):292-298 (2003)).

Elucidation of the human genome has provided an impetus for genetic engineering, gene therapy, and stem cell research. Recently, gene based expression of functional recombinant proteins and their epitopes as well as antibodies against them have permitted the topographical mapping of receptors to identify active sites and understand the mechanism of ligand receptor binding. Synthesis of chimeric genes composed of desired functional epitopes of more than one gene to produce recombinant proteins has become possible (Sugahara et al., "Biosynthesis of a Biologically Active Single Chain Containing the Human Common a and Chorionic Gonadotropin β Subunits in Tandem," *Proc Natl Acad Sci USA* 92:2041-2045 (1995); Sugahara et al., "Expression of Biologically Active Fusion Genes Encoding the Common a Subunit and Either the CGβ of FSHβ Subunits: Role of a Linker Sequence," *Mol Cell Endocrinol* 125:71-77 (1996); and Heikoop et al., "Structure-Based Design and Protein Engineering of Intersubunit Disulfide Bonds in Gonadotropins," *Nat Biotechnol* 15(7):658-662 (1997); Heikoop et al., "Evaluation of Subunit Truncation and the Nature of the Spacer for Single Chain Human Gonadotropins," *Eur J Biochem* 245(3):656-662 (1997)). A single peptide chain containing α and β subunits of human chorionic gonadotropin (hCG) in tandem has been shown to exhibit biological activity (Sugahara et al., "Biosynthesis of a Biologically Active Single Chain Containing the Human Common α and Chorionic Gonadotropin β Subunits in Tandem," *Proc Natl Acad Sci USA* 92:2041-2045 (1995)). Fusion genes encoding the common α-subunit of hCG and FSH-β subunit also expressed a biologically active protein (Sugahara et al., "Expression of Biologically Active Fusion Genes Encoding the Common α Subunit and Either the CGβ of FSH-β Subunits: Role of a Linker Sequence," *Mol Cell Endocrinol* 125:71-77 (1996)). Narayan et al., "Yoked Complexes of Human Choriogonadotropin and the Lutropin Receptor: Evidence that Monomeric Individual Subunits are Inactive," *Mol Endocrinol* 16(12):2733-2745 (2002), constructed two (hCG)-LHR complexes where the two hormone subunits and the receptor were engineered to form single polypeptide chains.

Chemical conjugates to create functional chimeric proteins have been made to enhance their immunogenicity and/or to modulate metabolic clearance rates and biological activity (Klein et al., "Pharmacokinetics and Pharmacodynamics of Single-Chain Recombinant Human Follicle-Stimulating Hormone Containing the Human Chorionic Gonadotropin Carboxyterminal Peptide in the Rhesus Monkey," *Fertil Steril* 77(6):1248-1255 (2002)). Chimeric proteins have also been produced where the common human α-subunit of human glycoprotein hormone has been non-covalently linked to the hormone specific β-subunits of hCG and hFSH to express respective intact hormones, and their ability to interact with LH-hCG and FSH receptors has been examined (Campbell et al., "Conversion of Human Choriogonadotropin Into a Follitropin by Protein Engineering," *Proc Natl Acad Sci USA* 88(3):760-764 (1991)). The active sites of human FSH have been chemically modified to alter their activity by using an azidobenzoyl derivative of a glycopeptide isolated from the fetuin digest by photoactivation (Rathnam et al., "Conjugation of a Fetuin Glycopeptide to Human Follicle-Stimulating Hormone and its Subunits by Photoactivation," *Biochim Biophys Acta* 624(2):436-442 (1980)). Chemical reactions used for the addition, deletion, or replacement of functional epitopes have been fraught with non-specific side reactions and changes in the conformation and function of the proteins. However, the availability of nucleic acid sequences of expressed proteins has opened new avenues to synthesize nucleic acid constructs to express hybrids of two different proteins. This is achieved by the use of site-specific restriction enzymes and ligases to produce chimeric genes, which, in turn, can express the corresponding hybrid proteins. A single-chain construct containing hCG α and β subunits in tandem was fused with the N-terminus of receptor LH-R to investigate their structure-function relationship (Wu et al., "Protein Engineering of Novel Constitutively Active Hormone-Receptor Complex," *J Biol Chem* 271:31638-31642 (1996)).

What is needed now is a chimeric nucleic acid molecule that encodes a fusion protein having both a lutropin hormone receptor protein, or a fragment thereof, and a human chorionic gonadotropin protein or a fragment thereof, where the lutropin hormone receptor protein or fragment, and the human chorionic gonadotropin protein or fragment thereof, are immunogenic. Such a bifunctional, immunogenic protein would provide a unique antigen for immunocontraception and gonadal regulation in vertebrates, including humans. The present invention is directed to overcoming these and other deficiencies in the art.

SUMMARY OF THE INVENTION

The present invention relates to a chimeric nucleic acid molecule encoding a fusion protein having a human lutropin hormone receptor domain and a human chorionic gonadotropin-β domain. The chimeric nucleic acid molecule of the present invention encodes a fusion protein that includes a full length human lutropin hormone receptor or an antigenic fragment thereof, and a full length human chorionic gonadotropin-β or an antigenic fragment thereof.

The present invention also relates to an isolated human lutropin hormone receptor/human chorionic gonadotropin-β fusion protein having a human lutropin hormone receptor domain and a human chorionic gonadotropin-β domain.

Another aspect of the present invention is an isolated antibody, or binding portion thereof, which recognizes the human lutropin hormone receptor domain and the human chorionic gonadotropin-β domain of the human lutropin hormone receptor/human chorionic gonadotropin-β fusion protein of the present invention.

Another aspect of the present invention is an isolated antibody, or binding portion thereof, which recognizes only the human lutropin hormone receptor domain of the human lutropin hormone receptor/human chorionic gonadotropin-β fusion protein of the present invention.

Another aspect of the present invention is an isolated antibody, or binding portion thereof, which recognizes only the human chorionic gonadotropin-β domain of the human lutropin hormone receptor/human chorionic gonadotropin-β fusion protein of the present invention.

The present invention also relates to an isolated antibody, or binding portion thereof, which recognizes a human lutropin hormone receptor protein or a fragment thereof.

The present invention also relates to a composition having an antibody, or binding portion thereof, that recognizes the human lutropin hormone receptor domain and the human chorionic gonadotropin-β domain of the human lutropin hormone receptor/human chorionic gonadotropin-β fusion protein of the present invention, and a pharmaceutical carrier.

The present invention also relates to a composition having an antibody, or binding portion thereof, that recognizes only the human lutropin hormone receptor domain of the human lutropin hormone receptor/human chorionic gonadotropin-β fusion protein of the present invention, and a pharmaceutical carrier.

The present invention also relates to a composition having an antibody, or binding portion thereof, that recognizes only the human chorionic gonadotropin-β domain of the human lutropin hormone receptor/human chorionic gonadotropin-β fusion protein of the present invention, and a pharmaceutical carrier.

Another aspect of the present invention is a method of immunocontraception. This method involves administering an antibody that recognizes the human lutropin hormone receptor domain and the human chorionic gonadotropin-β domain of the human lutropin hormone receptor/human chorionic gonadotropin-β fusion protein of the present invention to a subject under conditions effective to provide immunocontraception to the subject.

Another method of immunocontraception is provided in the present invention. This method involves administering an antibody recognizing a human lutropin hormone receptor protein, or a fragment thereof, to a subject under conditions effective to provide immunocontraception to the subject.

Yet another method of immunocontraception provided by the present invention involves administering the human lutropin receptor/human chorionic gonadotropin-β fusion protein of the present invention to a subject under conditions effective to provide immunocontraception to the subject.

The present invention relates to yet another method of immunocontraception. This method involves administering the chimeric nucleic acid molecule of the present invention that encodes a human lutropin hormone receptor/human chorionic gonadotropin-β fusion protein to a subject under conditions effective to provide immunocontraception to the subject.

Another aspect of the present invention is a method of treating an androgen-excess-mediated disease condition in a subject. This method involves administering an antibody, or a binding portion thereof, that recognizes the human lutropin hormone receptor domain and the human chorionic gonadotropin-β domain of the human lutropin hormone receptor/human chorionic gonadotropin-β fusion protein of the present invention, to a subject under conditions effective to treat the androgen-excess-mediated disease condition.

The present invention also relates to another method of treating an androgen-excess-mediated disease condition in a subject. This method involves administering an antibody, or a binding portion thereof, that recognizes the human lutropin hormone receptor domain, but not the human chorionic gonadotropin-β domain of the human lutropin hormone receptor/human chorionic gonadotropin-β fusion protein of the present invention, to a subject under conditions effective to treat the androgen-excess-mediated disease condition.

The present invention also relates to nucleic acid constructs, expression vectors, and hosts that include a chimeric nucleic acid molecule encoding a fusion protein having a human lutropin hormone receptor domain and a human chorionic gonadotropin-β domain.

The lutropin hormone receptor protein (hLH-R) and chorionic gonadotropin-β hormone (CG-β) are structurally and functionally similar and play an important role in reproduction via a common gonadal receptor (LH-R). A chimeric protein of LH-R conjugated with hCG-β could presumably become more antigenic since it will present to the immune system as a heterologous antigen to facilitate antibody response in a subject. Thus, in females, the antibody to a bifunctional protein containing LH-R and hCG-β moieties would block the binding of LH to the receptor, whereas antibodies to hCG-β would neutralize hCG produced by the blastocyst and inhibit implantation. In males, antibodies to such a bifunctional protein could be useful in blocking the LH receptor, leading to infertility. Thus, the present invention, which relates to a chimeric nucleic acid molecule encoding a hLH-R and hCG-β fusion protein, provides a unique antigen for immunocontraception and gonadal regulation in vertebrates, including humans.

BRIEF DESCRIPTION OF THE DRAWINGS

FIG. 3A shows blot probed with antibodies to LH-R. FIG. 3B shows blot probed with antibodies to hCG-β. Lane 1: Membrane proteins from transfected Sf9 cells probed with antibodies. Lane 2: Membrane proteins from mock-transfected Sf9 cells probed with antibodies. M: Protein markers.

FIG. 4A shows the percent specific binding of biotinylated-hCG to recombinant chimeric protein hLH-R-hCG-β, expressed in $2\times10^6$ Sf9 insect cells. FIG. 4B shows the percent specific binding of biotinylated-hCG to hLH-R alone, expressed in $2\times10^6$ Sf9 insect cells. Total binding of biotinylated-hCG in the absence of unlabeled hCG was adjusted to 100%. Specific binding of biotinylated-hCG was determined from the displacement of bound biotinylated-hCG at increasing concentrations of unlabeled hCG. The data are shown as Mean±SD of three independent experiments.

FIG. 5A shows results of stimulation by the recombinant chimeric hLH-R-hCG-β protein. FIG. 5B shows results of stimulation by LH-R protein alone. Dose-response curve of hCG-mediated increase in intracellular cAMP in Sf9 insect cells transfected with chimeric DNA construct as well as cAMP levels in the intercellular incubation medium. The data are shown as Means±SD of three independent experiments.

ECD DNA construct. Lane 3: solubilized proteins from transfected Sf9 cells with chimeric DNA construct. M: Protein size markers (36 kDa, 48 kDa, 62 kDa and 79 kDa).

Figure 9:
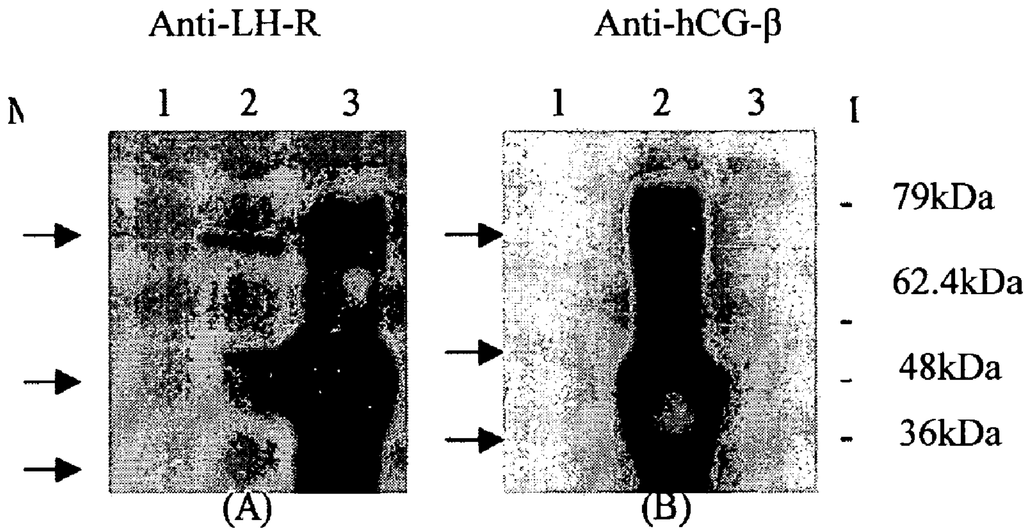

FIGS. 9A-B are western blots of solubilized membrane proteins from Sf9 cells transfected with hLH-R-ECD-hCG-β CTP chimeric construct. Sf9 cells transfected by recombinant baculovirus were collected after 72 hrs of transfection. Sixty μg of solubilized membrane proteins were separated on a 7.5% SDS-PAGE under reducing conditions. FIG. 9A shows blot probed with antibodies to LH-R. Lane 1: solubilized proteins from mock-transfected Sf9 cells. Lane 2: solubilized proteins from Sf9 cells transfected with the hLH-R-ECD construct. Lane 3: solubilized protein from Sf9 cells transfected with the hLH-R-ECD/hCG-CTP chimeric DNA construct. FIG. 9B shows blot probed with antibodies to hCG-β. Lane 1: solubilized proteins from Sf9 cells transfected with the hLH-R-ECD construct. Lane 2: solubilized protein from Sf9 cells transfected with the hLH-R-ECD/hCG-CTP chimeric DNA construct. Lane 3: Solubilized proteins from mock-transfected Sf9 cells. M: Protein size markers.

Figure 10:
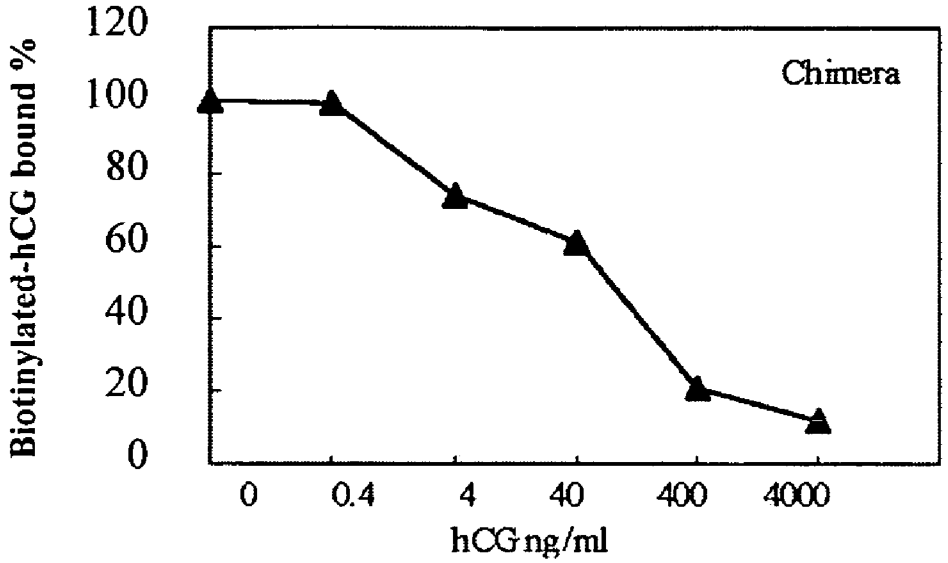

FIG. 10 is a graph showing the percent binding of biotinylated-hCG to recombinant chimeric protein hLH-R-ECD-hCG-β expressed in $2\times10^6$ Sf9 insect cells. Total binding of biotinylated hCG in the absence of unlabeled hCG was adjusted to 100%. Binding of biotinylated-hCG was determined from the displacement of bound biotinylated-hCG at increasing concentrations of unlabeled hCG. Data are presented as Mean±SD of three independent experiments.

Figure 11A:
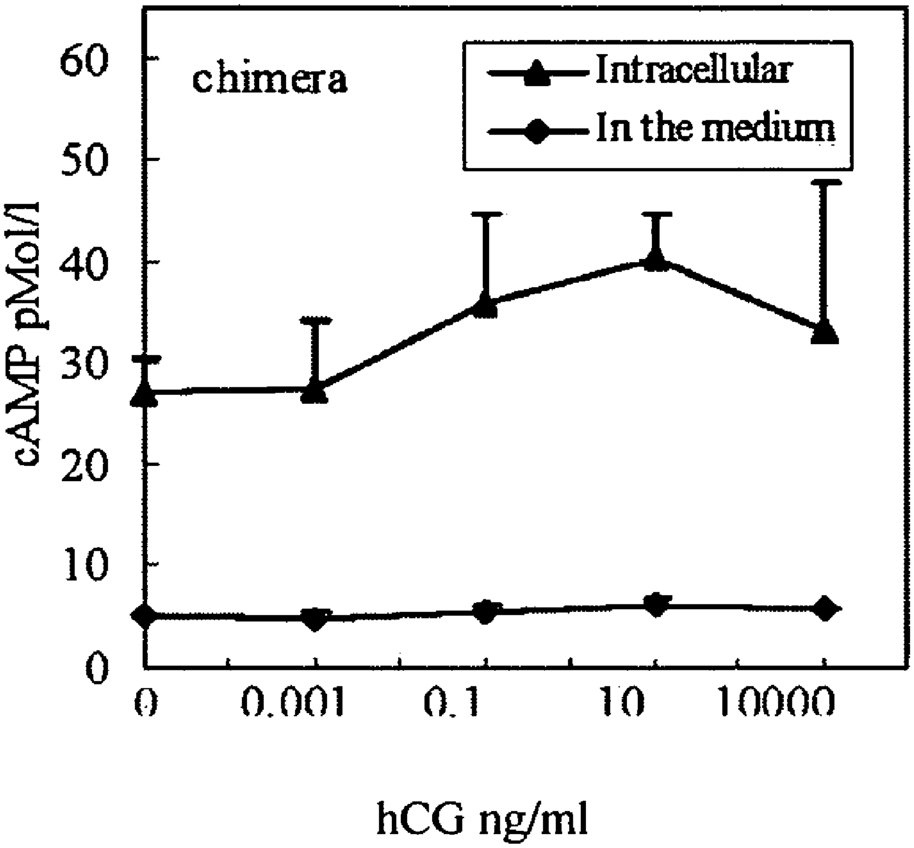
Figure 11B:
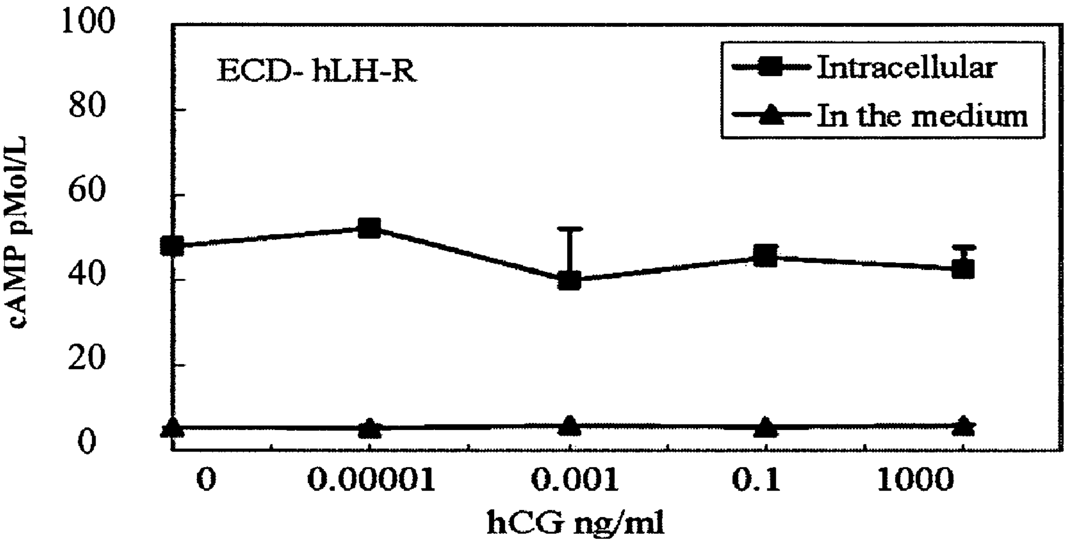
Figure 11C:
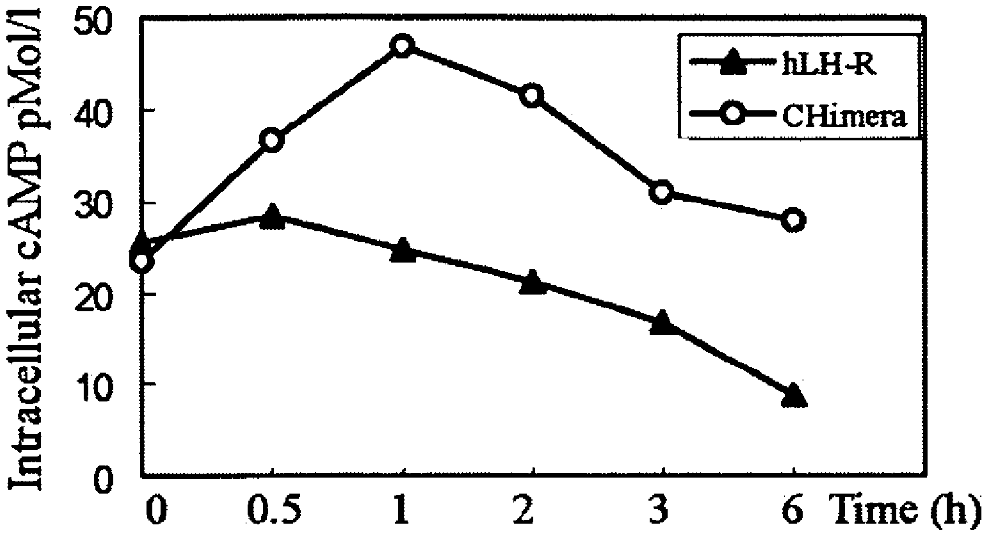

FIGS. 11A-C are graphs showing the ability of the hLH-R-ECD-hCG-β-CTP recombinant chimeric protein to stimulate intracellular cyclic AMP, expressed in $2\times10^6$ Sf9 insect cells as compared with cAMP in the culture medium. FIG. 11A shows the stimulation of cAMP production by the chimeric protein in the transfected Sf9 cells as well as in the incubation medium in the absence and presence of increasing quantities of hCG. FIG. 11B shows the stimulation of cAMP production by the LH-R-ECD protein alone in the transfected Sf9 cells as well as in the incubation medium in the absence and presence of increasing quantities of hCG. FIG. 11C shows the intracellular cAMP concentrations at different time intervals measured after Sf9 cells transfected with chimeric construct (o) and ECD-hLH-R alone (▲) incubating with 0.1 ng/ml hCG (C). The data are presented as Mean±SD of three independent experiments.

DETAILED DESCRIPTION OF THE INVENTION

The present invention relates to a chimeric nucleic acid molecule encoding a fusion protein having a human lutropin hormone receptor domain and a human chorionic gonadotropin-β domain. The fusion protein of the present invention includes a full length human lutropin hormone receptor or an antigenic fragment thereof, and a full length human chorionic gonadotropin-β or an antigenic fragment thereof, and includes additional amino acids suitable for linking together the human lutropin hormone receptor domain and the human chorionic gonadotropin-β domain.

An exemplary full length human lutropin hormone receptor suitable for use in the human lutropin hormone receptor/human chorionic gonadotropin-β fusion protein of the present invention has the amino acid of SEQ ID NO: 1, as follows:

```
Met Lys Gln Arg Phe Ser Ala Leu Gln Leu Leu Lys Leu Leu Leu Leu
 1               5                  10                  15

Leu Gln Leu Gln Pro Pro Leu Pro Arg Ala Leu Arg Glu Ala Leu Cys
            20                  25                  30

Pro Glu Pro Cys Asn Cys Val Pro Asp Gly Ala Leu Arg Cys Pro Gly
        35                  40                  45

Pro Thr Ala Gly Leu Thr Arg Leu Ser Leu Ala Tyr Leu Pro Val Lys
    50                  55                  60

Val Ile Pro Ser Gln Ala Phe Arg Gly Leu Asn Glu Val Ile Lys Ile
65                  70                  75                  80

Glu Ile Ser Gln Ile Asp Ser Leu Glu Arg Ile Glu Ala Asn Ala Phe
                85                  90                  95

Asp Asn Leu Leu Asn Leu Ser Glu Ile Leu Ile Gln Asn Thr Lys Asn
            100                 105                 110

Leu Arg Tyr Ile Glu Pro Gly Ala Phe Ile Asn Leu Pro Arg Leu Lys
        115                 120                 125

Tyr Leu Ser Ile Cys Asn Thr Gly Ile Arg Lys Phe Pro Asp Val Thr
    130                 135                 140

Lys Val Phe Ser Ser Glu Ser Asn Phe Ile Leu Glu Ile Cys Asp Asn
145                 150                 155                 160

Leu His Ile Thr Thr Ile Pro Gly Asn Ala Phe Gln Gly Met Asn Asn
                165                 170                 175

Glu Ser Val Thr Leu Lys Leu Tyr Gly Asn Gly Phe Glu Glu Val Gln
            180                 185                 190

Ser His Ala Phe Asn Gly Thr Thr Leu Thr Ser Leu Glu Leu Lys Glu
        195                 200                 205

Asn Val His Leu Glu Lys Met His Asn Gly Ala Phe Arg Gly Ala Thr
```

-continued

```
    210                 215                 220

Gly Pro Lys Thr Leu Asp Ile Ser Ser Thr Lys Leu Gln Ala Leu Pro
225                 230                 235                 240

Ser Tyr Gly Leu Glu Ser Ile Gln Arg Leu Ile Ala Thr Ser Ser Tyr
                245                 250                 255

Ser Leu Lys Lys Leu Pro Ser Arg Glu Thr Phe Val Asn Leu Leu Glu
            260                 265                 270

Ala Thr Leu Thr Tyr Pro Ser His Cys Cys Ala Phe Arg Asn Leu Pro
        275                 280                 285

Thr Lys Glu Gln Asn Phe Ser His Ser Ile Ser Glu Asn Phe Ser Lys
    290                 295                 300

Gln Cys Glu Ser Thr Val Arg Lys Val Ser Asn Lys Thr Leu Tyr Ser
305                 310                 315                 320

Ser Met Leu Ala Glu Ser Glu Leu Ser Gly Trp Asp Tyr Glu Tyr Gly
                325                 330                 335

Phe Cys Leu Pro Lys Thr Pro Arg Cys Ala Pro Glu Pro Asp Ala Phe
            340                 345                 350

Asn Pro Cys Glu Asp Ile Met Gly Tyr Asp Phe Leu Arg Val Leu Ile
        355                 360                 365

Trp Leu Ile Asn Ile Leu Ala Ile Met Gly Asn Met Thr Val Leu Phe
    370                 375                 380

Val Leu Leu Thr Ser Arg Tyr Lys Leu Thr Val Pro Arg Phe Leu Met
385                 390                 395                 400

Cys Asn Leu Ser Phe Ala Asp Phe Cys Met Gly Leu Tyr Leu Leu Leu
                405                 410                 415

Ile Ala Ser Val Asp Ser Gln Thr Lys Gly Gln Tyr Tyr Asn His Ala
            420                 425                 430

Ile Asp Trp Gln Thr Gly Ser Gly Cys Ser Thr Ala Gly Phe Phe Thr
        435                 440                 445

Val Phe Ala Ser Glu Leu Ser Val Tyr Thr Leu Thr Val Ile Thr Leu
    450                 455                 460

Glu Arg Trp His Thr Ile Thr Tyr Ala Ile His Leu Asp Gln Lys Leu
465                 470                 475                 480

Arg Leu Arg His Ala Ile Leu Ile Met Leu Gly Gly Trp Leu Phe Ser
                485                 490                 495

Ser Leu Ile Ala Met Leu Pro Leu Val Gly Val Ser Asn Tyr Met Lys
            500                 505                 510

Val Ser Ile Cys Phe Pro Met Asp Val Glu Thr Thr Leu Ser Gln Val
        515                 520                 525

Tyr Ile Leu Thr Ile Leu Ile Leu Asn Val Val Ala Phe Phe Ile Ile
    530                 535                 540

Cys Ala Cys Tyr Ile Lys Ile Tyr Phe Ala Val Arg Asn Pro Glu Leu
545                 550                 555                 560

Met Ala Thr Asn Lys Asp Thr Lys Ile Ala Lys Lys Met Ala Ile Leu
                565                 570                 575

Ile Phe Thr Asp Phe Thr Cys Met Ala Pro Ile Ser Phe Phe Ala Ile
            580                 585                 590

Ser Ala Ala Phe Lys Val Pro Leu Ile Thr Val Thr Asn Ser Lys Val
        595                 600                 605

Leu Leu Val Leu The Tyr Pro Ile Asn Ser Cys Ala Asn Pro Phe Leu
    610                 615                 620

Tyr Ala Ile Phe Thr Lys Thr Phe Gln Arg Asp Phe The Leu Leu Leu
625                 630                 635                 640
```

-continued

```
Ser Lys Phe Gly Cys Cys Lys Arg Arg Ala Glu Leu Tyr Arg Arg Lys
                645                 650                 655

Asp Phe Ser Ala Tyr Thr Ser Asn Cys Lys Asn Gly Phe Thr Gly Ser
            660                 665                 670

Asn Lys Pro Ser Gln Ser Thr Leu Lys Leu Ser Thr Leu His Cys Gln
        675                 680                 685

Gly Thr Ala Leu Leu Asp Lys Thr Arg Tyr Thr Glu Cys
    690                 695                 700
```

This full length human lutropin hormone receptor protein is encoded by a nucleic acid molecule having a nucleotide sequence of SEQ ID NO:2, as follows:

```
atgaagcagc ggttctcggc gctgcagctg ctgaagctgc tgctgctgct gcagctgcag    60
ccgccgctgc cacgagcgct gcgcgaggcg ctctgccctg agccctgcaa ctgcgtgccc   120
gacggcgccc tgcgctgccc cggccccacg gccggtctca ctcgactatc acttgcctac   180
ctccctgtca aagtgatccc atctcaagct ttcagaggac ttaatgaggt cataaaaatt   240
gaaatctctc agattgattc cctggaaagg atagaagcta atgcctttga caacctcctc   300
aatttgtctg aaatactgat ccagaacacc aaaaatctga gatacattga gcccggagca   360
tttataaatc ttcccggatt aaaatacttg agcatctgta acacaggcat cagaaagttt   420
ccagatgtta cgaaggtctt ctcctctgaa tcaaatttca ttctggaaat ttgtgataac   480
ttacacataa ccaccatacc aggaaatgct tttcaaggga tgaataatga atctgtaaca   540
ctcaaactat atggaaatgg atttgaagaa gtacaaagtc atgcattcaa tgggacgaca   600
ctgacttcac tggagctaaa ggaaaacgta catctggaga agatgcacaa tggagccttc   660
cgtggggcca cagggccgaa aaccttggat atttcttcca ccaaattgca ggccctgccg   720
agctatggcc tagagtccat tcagaggcta attgccacgt catcctattc tctaaaaaaa   780
ttgccatcaa gagaaacatt tgtcaatctc ctggaggcca cgttgactta ccccagccac   840
tgctgtgctt ttagaaactt gccaacaaaa gaacagaatt tttcacattc catttctgaa   900
aacttttcca aacaatgtga aagcacagta aggaaagtga gtaacaaaac actttattct   960
tccatgcttg ctgagagtga actgagtggc tgggactatg aatatggttt ctgcttaccc  1020
aagacacccc gatgtgctcc tgaaccagat gcttttaatc cctgtgaaga cattatgggc  1080
tatgacttcc ttagggtcct gatttggctg attaatattc tagccatcat gggaaacatg  1140
actgttcttt ttgttctcct gacaagtcgt tacaaactta cagtgcctcg ttttctcatg  1200
tgcaatctct cctttgcaga cttttgcatg gggctctatc tgctgctcat agcctcagtt  1260
gattcccaaa ccaagggcca gtactataac catgccatag actggcagac agggagtggg  1320
tgcagcactg ctggcttttt cactgtattc gcaagtgaac tttctgtcta caccctcacc  1380
gtcatcactc tagaaagatg gcacaccatc acctatgcta ttcacctgga ccaaaagctg  1440
cgattaagac atgccattct gattatgctt ggaggatggc tcttttcttc tctaattgct  1500
atgttgcccc ttgtcggtgt cagcaattac atgaaggtca gtatttgctt ccccatggat  1560
gtggaaacca ctctctcaca agtctatata ttaaccatcc tgattctcaa tgtggtggcc  1620
ttcttcataa tttgtgcttg ctacattaaa atttattttg cagttcgaaa cccagaatta  1680
atggctacca ataaagatac aaagattgct aagaaaatgg caatcctcat cttcaccgat  1740
ttcacctgca tggcacctat ctcttttttt gccatctcag ctgccttcaa agtacctctt  1800
```

-continued

```
atcacagtaa ccaactctaa agttttactg gttctttttt atcccatcaa ttcttgtgcc  1860

aatccatttc tgtatgcaat attcactaag acattccaaa gagatttctt tcttttgctg  1920

agcaaatttg gctgctgtaa acgtcgggct gaactttata gaaggaaaga tttttcagct  1980

tacacctcca actgcaaaaa tggcttcact ggatcaaata agccttctca atccaccttg  2040

aagttgtcca cattgcactg tcaaggtaca gctctcctag acaagactcg ctacacagag  2100

tgt                                                                2103
```

An exemplary full length human chorionic gonadotropin-β subunit suitable for use in a human lutropin hormone receptor/human chorionic gonadotropin-β fusion protein of the present invention has the amino acid of SEQ ID NO:3, as follows:

```
Met Glu Met Phe Gln Gly Leu Leu Leu Leu Leu Leu Leu Ser Met Gly
  1               5                  10                  15

Gly Thr Trp Ala Ser Lys Glu Pro Leu Arg Pro Arg Cys Arg Pro Ile
             20                  25                  30

Asn Ala Thr Leu Ala Val Glu Lys Glu Gly Cys Pro Val Cys Ile Thr
         35                  40                  45

Val Asn Thr Thr Ile Cys Ala Gly Tyr Cys Pro Thr Met Thr Arg Val
     50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165
```

This full length human chorionic gonadotropin-β subunit is encoded by a nucleic acid molecule having a nucleotide sequence of SEQ ID NO:4, as follows:

```
atggagatgt tccaggggct gctgctgttg ctgctgctga gcatgggcgg gacatgggca   60

tccaaggagc cgcttcggcc acggtgccgc cccatcaatg ccaccctggc tgtggagaag  120

gagggctgcc ccgtgtgcat caccgtcaac accaccatct gtgccggcta ctgccccacc  180

atgacccgcg tgctgcaggg ggtcctgccg gccctgcctc aggtggtgtg caactaccgc  240

gatgtgcgct tcgagtccat ccggctccct ggctgcccgc gcggcgtgaa ccccgtggtc  300

tcctacgccg tggctctcag ctgtcaatgt gcactctgcc gccgcagcac cactgactgc  360

gggggtccca aggaccaccc cttgacctgt gatgaccccc gcttccagga ctcctcttcc  420

tcaaaggccc ctcccccag ccttccaagt ccatcccgac tcccggggcc ctcggacacc  480

ccgatcctcc cacaa                                                   495
```

An exemplary fragment of the human lutropin hormone receptor domain suitable for use in a human lutropin hormone receptor/human chorionic gonadotropin-β fusion protein is N-terminal extracellular domain (ECD) of the hLH-R, known for high affinity ligand binding. The ECD of hLH-R has the amino acid sequence of SEQ ID NO:5, as follows:

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro
            340                 345
```

The hLH-R-is encoded by a nucleic acid molecule having a nucleotide sequence of SEQ ID NO:6, as follows:

```
atgaagcagc ggttctcggc gctgcagctg ctgaagctgc tgctgctgct gcagccgccg    60
ctgccacgag cgctgcgcga ggcgctctgc cctgagccct gcaactgcgt gcccgacggc   120
gccctgcgct gccccggccc cacggccggt ctcactcgac tatcacttgc ctacctccct   180
gtcaaagtga tcccatctca agctttcaga ggacttaatg aggtcataaa aattgaaatc   240
tctcagattg attccctgga aaggatagaa gctaatgcct ttgacaacct cctcaatttg   300
tctgaaatac tgatccagaa caccaaaaat ctgagataca ttgagcccgg agcatttata   360
aatcttcccg gattaaaata cttgagcatc tgtaacacag gcatcagaaa gtttccagat   420
gttacgaagg tcttctcctc tgaatcaaat ttcattctgg aaatttgtga taacttacac   480
ataaccacca taccaggaaa tgcttttcaa gggatgaata atgaatctgt aacactcaaa   540
ctatatggaa atggatttga agaagtacaa agtcatgcat tcaatgggac gacactgact   600
tcactggagc taaaggaaaa cgtacatctg gagaagatgc acaatggagc cttccgtggg   660
gccacagggc cgaaaacctt ggatatttct tccaccaaat tgcaggccct gccgagctat   720
ggcctagagt ccattcagag gctaattgcc acgtcatcct attctctaaa aaaattgcca   780
tcaagagaaa catttgtcaa tctcctggag gccacgttga cttaccccag ccactgctgt   840
gcttttagaa acttgccaac aaaagaacag aatttttcac attccatttc tgaaaacttt   900
tccaaacaat gtgaaagcac agtaaggaaa gtgagtaaca aaacacttta ttcttccatg   960
cttgctgaga gtgaactgag tggctgggac tatgaatatg gtttctgctt acccaagaca  1020
ccccgatgtg ctcctgaacc a                                            1041
```

An exemplary fragment of the human chorionic gonadotropin-β subunit suitable for the human lutropin hormone receptor/human chorionic gonadotropin-β fusion protein of the present invention has the amino acid sequence of SEQ ID NO:7, as follows:

```
Leu Thr Cys Asp Asp Pro Arg Phe Gln Asp Ser Ser Ser Ser Lys Ala
  1               5                  10                  15

Pro Pro Pro Ser Leu Pro Ser Pro Ser Arg Leu Pro Gly Pro Ser Asp
             20                  25                  30

Thr Pro Ile Leu Pro Gln
         35
```

This fragment of the human chorionic gonadotropin-β subunit, which includes the carboxyl terminal peptide (CTP) of the human chorionic gonadotropin-β domain, is encoded by a nucleic acid molecule having the nucleotide sequence of SEQ ID NO:8 as follows:

```
ttgacctgtg atgacccccg cttccaggac tcctcttcct caaaggcccc tccccccagc   60
cttccaagtc catcccgact cccggggccc tcggacaccc cgatcctccc acaa        114
```

Another exemplary full length human lutropin hormone receptor suitable for use in the hLH-R/hCG fusion protein of the present invention is a protein that is a variant of SEQ ID NO:1. This protein has an amino acid sequence of SEQ ID NO:9, as follows:

```
Met Lys Gln Arg Phe Ser Ala Leu Gln Leu Leu Lys Leu Leu Leu Leu
 1               5                  10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430
```

-continued

```
Trp Gln Thr Gly Ser Gly Cys Ser Thr Ala Gly Phe Phe Thr Val Phe
        435                 440                 445

Ala Ser Glu Leu Ser Val Tyr Thr Leu Thr Val Ile Thr Leu Glu Arg
    450                 455                 460

Trp His Thr Ile Thr Tyr Ala Ile Hls Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
    690                 695
```

This variant full-length hLH-R protein is encoded by a nucleic acid molecule having the nucleotide sequence of SEQ ID NO:10, as follows:

```
atgaagcagc ggttctcggc gctgcagctg ctgaagctgc tgctgctgct gcagccgccg    60

ctgccacgag cgctgcgcga ggcgctctgc cctgagccct gcaactgcgt gcccgacggc   120

gccctgcgct gccccggccc cacggccggt ctcactcgac tatcacttgc ctacctccct   180

gtcaaagtga tcccatctca agctttcaga ggacttaatg aggtcataaa aattgaaatc   240

tctcagattg attccctgga aaggatagaa gctaatgcct ttgacaacct cctcaatttg   300

tctgaaatac tgatccagaa caccaaaaat ctgagataca ttgagcccgg agcatttata   360

aatcttcccg gattaaaata cttgagcatc tgtaacacag gcatcagaaa gtttccagat   420

gttacgaagg tcttctcctc tgaatcaaat ttcattctgg aaatttgtga taacttacac   480

ataaccacca taccaggaaa tgcttttcaa gggatgaata atgaatctgt aacactcaaa   540

ctatatggaa atggatttga agaagtacaa agtcatgcat tcaatgggac gacactgact   600
```

-continued

```
tcactggagc taaaggaaaa cgtacatctg gagaagatgc acaatggagc cttccgtggg   660
gccacagggc cgaaaacctt ggatatttct tccaccaaat tgcaggccct gccgagctat   720
ggcctagagt ccattcagag gctaattgcc acgtcatcct attctctaaa aaaattgcca   780
tcaagagaaa catttgtcaa tctcctggag gccacgttga cttaccccag ccactgctgt   840
gcttttagaa acttgccaac aaaagaacag aatttttcac attccatttc tgaaaacttt   900
tccaaacaat gtgaaagcac agtaaggaaa gtgagtaaca aaacacttta ttcttccatg   960
cttgctgaga gtgaactgag tggctgggac tatgaatatg gtttctgctt acccaagaca  1020
ccccgatgtg ctcctgaacc agatgctttt aatccctgtg aagacattat gggctatgac  1080
ttccttaggg tcctgatttg gctgattaat attctagcca tcatgggaaa catgactgtt  1140
ctttttgttc tcctgacaag tcgttacaaa cttacagtgc ctcgttttct catgtgcaat  1200
ctctcctttg cagactttttg catggggctc tatctgctgc tcatagcctc agttgattcc  1260
caaaccaagg gccagtacta taaccatgcc atagactggc agacagggag tgggtgcagc  1320
actgctggct tttcactgt attcgcaagt gaactttctg tctacaccct caccgtcatc  1380
actctagaaa gatggcacac catcacctat gctattcacc tggaccaaaa gctgcgatta  1440
agacatgcca ttctgattat gcttggagga tggctctttt cttctctaat tgctatgttg  1500
ccccttgtcg gtgtcagcaa ttacatgaag gtcagtattt gcttccccat ggatgtggaa  1560
accactctct cacaagtcta tatattaacc atcctgattc tcaatgtggt ggccttcttc  1620
ataatttgtg cttgctacat taaaatttat tttgcagttc gaaacccaga attaatggct  1680
accaataaag atacaaagat tgctaagaaa atggcaatcc tcatcttcac cgatttcacc  1740
tgcatggcac ctatctcttt ttttgccatc tcagctgcct tcaaagtacc tcttatcaca  1800
gtaaccaact ctaaagtttt actggttctt ttttatccca tcaattcttg tgccaatcca  1860
tttctgtatg caatattcac taagacattc caaagagatt tctttctttt gctgagcaaa  1920
tttggctgct gtaaacgtcg ggctgaactt tatagaagga aagatttttc agcttacacc  1980
tccaactgca aaaatggctt cactggatca aataagcctt ctcaatccac cttgaagttg  2040
tccacattgc actgtcaagg tacagctctc ctagacaaga ctcgctacac agagtgt     2097
```

This variant human lutropin hormone receptor (SEQ ID NO:10) differs from the human lutropin hormone receptor protein of SEQ ID NO:1 in lacking two amino acids, a leucine and a glycine, that are present in SEQ ID NO:1 at positions 19 and 20, respectively. SEQ ID NO:10 is missing the corresponding encoding nucleotides that are present in SEQ ID NO:2 at positions 55-60. However, the variant protein shows no functional difference as compared with the receptor protein having SEQ ID NO:1 (Atger et al., "Structure of the Human Luteinizing Hormone-Choriogonadotropin Receptor Gene: Unusual Promoter and 5' Non-Coding Regions," *Mol Cell Endocrinol* 111(2):113-123 (1995), which is hereby incorporated by reference in its entirety).

Also suitable for making the human lutropin hormone receptor/human chorionic gonadotropin-β fusion protein of the present invention are proteins encoded by a nucleic acid molecule having at least 96% similarity, preferably 97%, most preferably 98% similarity to a nucleic acid molecule having SEQ ID Nos. 2, 4, 6, 8, or 10. The extent of similarity between two sequences can be based on percent sequence identity. "Identity" as used herein means the extent to which two (nucleotide or amino acid) sequences are invariant. Sequence "similarity" or "identity" in the context of two nucleic acid or polypeptide sequences includes reference to the residues in the two sequences that are the same when aligned for maximum correspondence over a specified comparison window. The similarity of two proteins (or nucleic acids) can be determined using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes," *Proc. Natl. Acad. Sci. USA* 87(6):2264-2268 (1990), modified as in Karlin et al., "Applications and Statistics for Multiple High-Scoring Segments in Molecular Sequences," *Proc. Natl. Acad. Sci. USA* 90(12):5873-5877 (1993), which are hereby incorporated by reference in their entirety. Such an algorithm is incorporated into the NBLAST and XBLAST programs of Altschul et al., *J. Mol. Biol.* 215:403-410 91990), which is hereby incorporated by reference in its entirety. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., "Gapped BLAST and PSI-BLAST: A New Generation of Protein Database Search Programs,"]*Nucleic Acids Res.* 25:3389-3402 (1997), which is hereby incorporated by reference in its entirety. Alternatively, PSI-Blast can be used to perform an iterated search which detects distant relationships between molecules (Altschul et al., "Gapped BLAST and PSI-BLAST: A New Generation of Protein Database Search Programs," *Nucleic Acids Res.* 25:3389-3402 (1997), which is hereby incorporated by reference in its entirety). When utilizing BLAST, Gapped BLAST, and PSI-Blast programs, the default parameters of the respective programs (e.g., XBLAST and NBLAST) can be used. (See the NCBI website for more information.) Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, *Comput. Appl. Biosci.* 10:3-5 (1994), which is hereby incorporated by reference in its entirety; and FASTA described in Pearson et al., "Improved tools for biological sequence comparison," *Proc Natl Acad Sci USA* 85:2444-8 (1988), which is hereby incorporated by reference in its entirety. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

Also suitable for the preparation of the chimeras of the present invention is any nucleic acid molecule capable of hybridizing to a nucleic acid molecule having SEQ ID Nos. 2, 4, 6, 8, or 10 under highly stringent conditions. The term "stringent conditions" as used herein refers to parameters which are familiar in the art. Nucleic acid hybridization parameters may be found in references which compile such methods, e.g. Sambrook et al., *Molecular Cloning: A Laboratory Manual*, eds., Second Edition, Cold Spring Harbor Laboratory Press, Cold Spring Harbor, New York (1989) or *Current Protocols in Molecular Biology*, Ausubel, et al., Eds., Greene Publishing and Wiley-Interscience, New York (1995). Methods as taught by a manufacturer of hybridization supplies and reagents are also highly suitable for use in the present invention (e.g., Invitrogen, Carlsbad, Calif.). More specifically, stringent conditions, as used herein, refers, for example, to hybridization at 56°-65° C. in hybridization buffer having 4-5×SSC, 0.02% ficoll, 0.02% polyvinyl pyrrolidone, 0.02% bovine serum albumin, 0.5% SDS, 2 mM EDTA, where SSC is 0.1 5M sodium chloride/0.015M sodium citrate, pH 7; SDS is sodium dodecyl sulfate; and EDTA is ethylenediaminetetraacetic acid. After hybridization, the membrane upon which the DNA is immobilized is washed in 2×SSC at room (ambient) temperature and then washed one or more times at 0.1X SSC/0.1% SDS, at temperatures from ambient temperature up to 68° C. There are other conditions, reagents, and so forth, which can be used, and would result in a similar degree of stringency. The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure. The skilled artisan will be familiar with such conditions, and thus they are not given here. It will be understood, however, that the skilled artisan will be able to manipulate the conditions in a manner to permit the clear identification of homologs and alleles of the hLH-R and hCG nucleic acids of the invention.

Suitable variant nucleic acid molecules having at least 98% similarity to SEQ ID Nos. 2, 4, 6, 8, and 10, or which are capable of hybridizing under stringent conditions as characterized herein, will encode a protein having a high amino acid identity to the native protein. Such nucleotide variants can be expected to encode a protein variant that is functionally equivalent to the human lutropin hormone receptor and human chorionic gonadotropin-β proteins of the present invention having SEQ ID Nos. 1, 3, 5, 7 and 9. By "functionally equivalent" it is meant that the variant protein has substantially the same biological effect as the native protein of interest, in particular with regard to the antigenic properties of the protein.

An indication that two protein sequences are substantially identical is that one protein is immunologically reactive with antibodies raised against the second protein. A protein is substantially identical to a second protein, for example, where the two proteins differ only by a conservative substitution. Generally, sequence identity of an amino acid of the invention is at least 80%, 85% or 87%, alternatively at least 92%, 94%, or 96%, and preferably 98% sequence identity to the native proteins of the present invention (and their naturally occurring alleles).

In one aspect of the present invention, the fusion protein of the present invention includes the full length human lutropin hormone receptor (SEQ ID NO:1) and the full length human chorionic gonadotropin-β subunit (SEQ ID NO: 3) joined to form a bifunctional chimeric fusion protein (chimera 1). A small peptide linker consisting of two amino acids, Arg-Ser, is located between the C-terminus of the hLH-R domain and the N-terminus of the hCG-β domain to form a contiguous hLH-R-hCG-β fusion protein. This fusion protein has the amino acid sequence of SEQ ID NO:11, as follows:

```
Met Lys Gln Arg Phe Ser Ala Leu Gln Leu Leu Lys Leu Leu Leu Leu
 1               5                  10                  15

Leu Gln Leu Gln Pro Pro Leu Pro Arg Ala Leu Arg Glu Ala Leu Cys
            20                  25                  30

Pro Glu Pro Cys Asn Cys Val Pro Asp Gly Ala Leu Arg Cys Pro Gly
        35                  40                  45
```

-continued

```
Pro Thr Ala Gly Leu Thr Arg Leu Ser Leu Ala Tyr Leu Pro Val Lys
     50                  55                  60

Val Ile Pro Ser Gln Ala Phe Arg Gly Leu Asn Glu Val Ile Lys Ile
 65                  70                  75                  80

Glu Ile Ser Gln Ile Asp Ser Leu Glu Arg Ile Glu Ala Asn Ala Phe
                 85                  90                  95

Asp Asn Leu Leu Asn Leu Ser Glu Ile Leu Ile Gln Asn Thr Lys Asn
            100                 105                 110

Leu Arg Tyr Ile Glu Pro Gly Ala Phe Ile Asn Leu Pro Arg Leu Lys
        115                 120                 125

Tyr Leu Ser Ile Cys Asn Thr Gly Ile Arg Lys Phe Pro Asp Val Thr
    130                 135                 140

Lys Val Phe Ser Ser Glu Ser Asn Phe Ile Leu Glu Ile Cys Asp Asn
145                 150                 155                 160

Leu His Ile Thr Thr Ile Pro Gly Asn Ala Phe Gln Gly Met Asn Asn
                165                 170                 175

Glu Ser Val Thr Leu Lys Leu Tyr Gly Asn Gly Phe Glu Glu Val Gln
            180                 185                 190

Ser His Ala Phe Asn Gly Thr Thr Leu Thr Ser Leu Glu Leu Lys Glu
        195                 200                 205

Asn Val His Leu Glu Lys Met His Asn Gly Ala Phe Arg Gly Ala Thr
    210                 215                 220

Gly Pro Lys Thr Leu Asp Ile Ser Ser Thr Lys Leu Gln Ala Leu Pro
225                 230                 235                 240

Ser Tyr Gly Leu Glu Ser Ile Gln Arg Leu Ile Ala Thr Ser Ser Tyr
                245                 250                 255

Ser Leu Lys Lys Leu Pro Ser Arg Glu Thr Phe Val Asn Leu Leu Glu
            260                 265                 270

Ala Thr Leu Thr Tyr Pro Ser His Cys Cys Ala Phe Arg Asn Leu Pro
        275                 280                 285

Thr Lys Glu Gln Asn Phe Ser His Ser Ile Ser Glu Asn Phe Ser Lys
    290                 295                 300

Gln Cys Glu Ser Thr Val Arg Lys Val Ser Asn Lys Thr Leu Tyr Ser
305                 310                 315                 320

Ser Met Leu Ala Glu Ser Glu Leu Ser Gly Trp Asp Tyr Glu Tyr Gly
                325                 330                 335

Phe Cys Leu Pro Lys Thr Pro Arg Cys Ala Pro Glu Pro Asp Ala Phe
            340                 345                 350

Asn Pro Cys Glu Asp Ile Met Gly Tyr Asp Phe Leu Arg Val Leu Ile
        355                 360                 365

Trp Leu Ile Asn Ile Leu Ala Ile Met Gly Asn Met Thr Val Leu Phe
    370                 375                 380

Val Leu Leu Thr Ser Arg Tyr Lys Leu Thr Val Pro Arg Phe Leu Met
385                 390                 395                 400

Cys Asn Leu Ser Phe Ala Asp Phe Cys Met Gly Leu Tyr Leu Leu Leu
                405                 410                 415

Ile Ala Ser Val Asp Ser Gln Thr Lys Gly Gln Tyr Tyr Asn His Ala
            420                 425                 430

Ile Asp Trp Gln Thr Gly Ser Gly Cys Ser Thr Ala Gly Phe Phe Thr
        435                 440                 445

Val Phe Ala Ser Glu Leu Ser Val Tyr Thr Leu Thr Val Ile Thr Leu
    450                 455                 460

Glu Arg Trp His Thr Ile Thr Tyr Ala Ile His Leu Asp Gln Lys Leu
```

-continued

```
465                 470                 475                 480

Arg Leu Arg His Ala Ile Leu Ile Met Leu Gly Gly Trp Leu Phe Ser
                485                 490                 495

Ser Leu Ile Ala Met Leu Pro Leu Val Gly Val Ser Asn Tyr Met Lys
            500                 505                 510

Val Ser Ile Cys Phe Pro Met Asp Val Glu Thr Thr Leu Ser Gln Val
        515                 520                 525

Tyr Ile Leu Thr Ile Leu Ile Leu Asn Val Val Ala Phe Phe Ile Ile
    530                 535                 540

Cys Ala Cys Tyr Ile Lys Ile Tyr Phe Ala Val Arg Asn Pro Glu Leu
545                 550                 555                 560

Met Ala Thr Asn Lys Asp Thr Lys Ile Ala Lys Lys Met Ala Ile Leu
                565                 570                 575

Ile Phe Thr Asp Phe Thr Cys Met Ala Pro Ile Ser Phe Phe Ala Ile
            580                 585                 590

Ser Ala Ala Phe Lys Val Pro Leu Ile Thr Val Thr Asn Ser Lys Val
        595                 600                 605

Leu Leu Val Leu Phe Tyr Pro Ile Asn Ser Cys Ala Asn Pro Phe Leu
    610                 615                 620

Tyr Ala Ile Phe Thr Lys Thr Phe Gln Arg Asp Phe Phe Leu Leu Leu
625                 630                 635                 640

Ser Lys Phe Gly Cys Cys Lys Arg Arg Ala Glu Leu Tyr Arg Arg Lys
                645                 650                 655

Asp Phe Ser Ala Tyr Thr Ser Asn Cys Lys Asn Gly Phe Thr Gly Ser
            660                 665                 670

Asn Lys Pro Ser Gln Ser Thr Leu Lys Leu Ser Thr Leu His Cys Gln
        675                 680                 685

Gly Thr Ala Leu Leu Asp Lys Thr Arg Tyr Thr Glu Cys Arg Ser Met
    690                 695                 700

Glu Met Phe Gln Gly Leu Leu Leu Leu Leu Leu Leu Ser Met Gly Gly
705                 710                 715                 720

Thr Trp Ala Ser Lys Glu Pro Leu Arg Pro Arg Cys Arg Pro Ile Asn
                725                 730                 735

Ala Thr Leu Ala Val Glu Lys Glu Gly Cys Pro Val Cys Ile Thr Val
            740                 745                 750

Asn Thr Thr Ile Cys Ala Gly Tyr Cys Pro Thr Met Thr Arg Val Leu
        755                 760                 765

Gln Gly Val Leu Pro Ala Leu Pro Gln Val Val Cys Asn Tyr Arg Asp
    770                 775                 780

Val Arg Phe Glu Ser Ile Arg Leu Pro Gly Cys Pro Arg Gly Val Asn
785                 790                 795                 800

Pro Val Val Ser Tyr Ala Val Ala Leu Ser Cys Gln Cys Ala Leu Cys
                805                 810                 815

Arg Arg Ser Thr Thr Asp Cys Gly Gly Pro Lys Asp His Pro Leu Thr
            820                 825                 830

Cys Asp Asp Pro Arg Phe Gln Asp Ser Ser Ser Ser Lys Ala Pro Pro
        835                 840                 845

Pro Ser Leu Pro Ser Pro Ser Arg Leu Pro Gly Pro Ser Asp Thr Pro
    850                 855                 860

Ile Leu Pro Gln
865
```

This human lutropin hormone receptor/human chorionic gonadotropin-β fusion protein of the present invention is encoded by a nucleic acid molecule having the nucleotide sequence of SEQ ID NO:12, as follows:

```
atgaagcagc ggttctcggc gctgcagctg ctgaagctgc tgctgctgct gcagctgcag    60
ccgccgctgc cacgagcgct gcgcgaggcg ctctgccctg agccctgcaa ctgcgtgccc   120
gacggcgccc tgcgctgccc cggccccacg gccggtctca ctcgactatc acttgcctac   180
ctccctgtca aagtgatccc atctcaagct ttcagaggac ttaatgaggt cataaaaatt   240
gaaatctctc agattgattc cctggaaagg atagaagcta atgcctttga caacctcctc   300
aatttgtctg aaatactgat ccagaacacc aaaaatctga gatacattga gcccggagca   360
tttataaatc ttcccggatt aaaatacttg agcatctgta acacaggcat cagaaagttt   420
ccagatgtta cgaaggtctt ctcctctgaa tcaaatttca ttctggaaat ttgtgataac   480
ttacacataa ccaccatacc aggaaatgct tttcaaggga tgaataatga atctgtaaca   540
ctcaaactat atggaaatgg atttgaagaa gtacaaagtc atgcattcaa tgggacgaca   600
ctgacttcac tggagctaaa ggaaaacgta catctggaga agatgcacaa tggagccttc   660
cgtggggcca cagggccgaa aaccttggat atttcttcca ccaaattgca ggccctgccg   720
agctatggcc tagagtccat tcagaggcta attgccacgt catcctattc tctaaaaaaa   780
ttgccatcaa gagaaacatt tgtcaatctc ctggaggcca cgttgactta ccccagccac   840
tgctgtgctt ttagaaactt gccaacaaaa gaacagaatt tttcacattc catttctgaa   900
aacttttcca aacaatgtga aagcacagta aggaaagtga gtaacaaaac actttattct   960
tccatgcttg ctgagagtga actgagtggc tgggactatg aatatggttt ctgcttaccc  1020
aagacacccc gatgtgctcc tgaaccagat gcttttaatc cctgtgaaga cattatgggc  1080
tatgacttcc ttagggtcct gatttggctg attaatattc tagccatcat gggaaacatg  1140
actgttcttt ttgttctcct gacaagtcgt tacaaactta cagtgcctcg ttttctcatg  1200
tgcaatctct cctttgcaga cttttgcatg gggctctatc tgctgctcat agcctcagtt  1260
gattcccaaa ccaagggcca gtactataac catgccatag actggcagac agggagtggg  1320
tgcagcactg ctggcttttt cactgtattc gcaagtgaac tttctgtcta caccctcacc  1380
gtcatcactc tagaaagatg gcacaccatc acctatgcta ttcacctgga ccaaaagctg  1440
cgattaagac atgccattct gattatgctt ggaggatggc tcttttcttc tctaattgct  1500
atgttgcccc ttgtcggtgt cagcaattac atgaaggtca gtatttgctt ccccatggat  1560
gtggaaacca ctctctcaca agtctatata ttaaccatcc tgattctcaa tgtggtggcc  1620
ttcttcataa tttgtgcttg ctacattaaa atttattttg cagttcgaaa cccagaatta  1680
atggctacca ataaagatac aaagattgct aagaaaatgg caatcctcat cttcaccgat  1740
ttcacctgca tggcacctat ctcttttttt gccatctcag ctgccttcaa agtacctctt  1800
atcacagtaa ccaactctaa agttttactg gttctttttt atcccatcaa ttcttgtgcc  1860
aatccatttc tgtatgcaat attcactaag acattccaaa gagatttctt tcttttgctg  1920
agcaaatttg gctgctgtaa acgtcgggct gaactttata gaaggaaaga tttttcagct  1980
tacacctcca actgcaaaaa tggcttcact ggatcaaata agccttctca atccaccttg  2040
aagttgtcca cattgcactg tcaaggtaca gctctcctag acaagactcg ctacacagag  2100
tgtagatcta tggagatgtt ccaggggctg ctgctgttgc tgctgctgag catgggcggg  2160
acatgggcat ccaaggagcc gcttcggcca cggtgccgcc ccatcaatgc caccctggct  2220
```

-continued

```
gtggagaagg agggctgccc cgtgtgcatc accgtcaaca ccaccatctg tgccggctac  2280

tgccccacca tgacccgcgt gctgcagggg gtcctgccgg ccctgcctca ggtggtgtgc  2340

aactaccgcg atgtgcgctt cgagtccatc cggctccctg gctgcccgcg cggcgtgaac  2400

cccgtggtct cctacgccgt ggctctcagc tgtcaatgtg cactctgccg ccgcagcacc  2460

actgactgcg gggtcccaa ggaccacccc ttgacctgtg atgacccccg cttccaggac  2520

tcctcttcct caaaggcccc tccccccagc cttccaagtc catcccgact cccggggccc  2580

tcggacaccc cgatcctccc acaa                                         2604
```

In another aspect of the present invention, the fusion protein of the present invention includes a full length human lutropin hormone receptor (SEQ ID NO: 1) and a suitable fragment of the full length human chorionic gonadotropin-β subunit (SEQ ID NO: 7). A small peptide linker consisting of two amino acids, Gly-Thr, is located between the C-terminus of the hLH-R domain and the N-terminus of the hCG-β domain to form a contiguous hLH-R-hCG-β fusion protein. This fusion protein (chimera 2) has the amino acid sequence of SEQ ID NO:13, as follows:

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Gys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
```

-continued

```
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445

Ala Ser Glu Leu Ser Val Tyr Thr Leu Thr Val Ile Thr Leu Glu Arg
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685
```

-continued

```
Ala Leu Leu Asp Lys Thr Arg Tyr Thr Glu Gys Gly Thr Leu Thr Cys
    690                 695                 700

Asp Asp Pro Arg Phe Gln Asp Ser Ser Ser Ser Lys Ala Pro Pro Pro
705                 710                 715                 720

Ser Leu Pro Ser Pro Ser Arg Leu Pro Gly Pro Ser Asp Thr Pro Ile
                725                 730                 735

Leu Pro Gln
```

This human lutropin hormone receptor/human chorionic gonadotropin-β fusion protein of the present invention is encoded by the nucleic acid molecule having the nucleotide sequence of SEQ ID NO:14, as follows:

```
atgaagcagc ggttctcggc gctgcagctg ctgaagctgc tgctgctgct gcagccgccg     60
ctgccacgag cgctgcgcga ggcgctctgc cctgagccct gcaactgcgt gcccgacggc    120
gccctgcgct gccccggccc cacggccggt ctcactcgac tatcacttgc ctacctccct    180
gtcaaagtga tcccatctca agctttcaga ggacttaatg aggtcataaa aattgaaatc    240
tctcagattg attccctgga aaggatagaa gctaatgcct ttgacaacct cctcaatttg    300
tctgaaatac tgatccagaa caccaaaaat ctgagataca ttgagcccgg agcatttata    360
aatcttcccg gattaaaata cttgagcatc tgtaacacag gcatcagaaa gtttccagat    420
gttacgaagg tcttctcctc tgaatcaaat ttcattctgg aaatttgtga taacttacac    480
ataaccacca taccaggaaa tgcttttcaa gggatgaata atgaatctgt aacactcaaa    540
ctatatggaa atggatttga agaagtacaa agtcatgcat tcaatgggac gacactgact    600
tcactggagc taaaggaaaa cgtacatctg gagaagatgc acaatggagc cttccgtggg    660
gccacagggc cgaaaacctt ggatatttct tccaccaaat tgcaggccct gccgagctat    720
ggcctagagt ccattcagag gctaattgcc acgtcatcct attctctaaa aaaattgcca    780
tcaagagaaa catttgtcaa tctcctggag gccacgttga cttaccccag ccactgctgt    840
gcttttagaa acttgccaac aaaagaacag aatttttcac attccatttc tgaaaacttt    900
tccaaacaat gtgaaagcac agtaaggaaa gtgagtaaca aaacacttta ttcttccatg    960
cttgctgaga gtgaactgag tggctgggac tatgaatatg gtttctgctt acccaagaca   1020
ccccgatgtg ctcctgaacc agatgctttt aatccctgtg aagacattat gggctatgac   1080
ttccttaggg tcctgatttg gctgattaat attctagcca tcatgggaaa catgactgtt   1140
ctttttgttc tcctgacaag tcgttacaaa cttacagtgc ctcgttttct catgtgcaat   1200
ctctcctttg cagacttttg catggggctc tatctgctgc tcatagcctc agttgattcc   1260
caaaccaagg gccagtacta taaccatgcc atagactggc agacagggag tgggtgcagc   1320
actgctggct tttcactgt attcgcaagt gaactttctg tctacaccct caccgtcatc   1380
actctagaaa gatggcacac catcacctat gctattcacc tggaccaaaa gctgcgatta   1440
agacatgcca ttctgattat gcttggagga tggctctttt cttctctaat tgctatgttg   1500
ccccttgtcg gtgtcagcaa ttacatgaag gtcagtattt gcttccccat ggatgtggaa   1560
accactctct cacaagtcta tatattaacc atcctgattc tcaatgtggt ggccttcttc   1620
ataatttgtg cttgctacat taaaatttat tttgcagttc gaaacccaga attaatggct   1680
accaataaag atacaaagat tgctaagaaa atggcaatcc tcatcttcac cgatttcacc   1740
tgcatggcac ctatctcttt ttttgccatc tcagctgcct tcaaagtacc tcttatcaca   1800
```

-continued

```
gtaaccaact ctaaagtttt actggttctt ttttatccca tcaattcttg tgccaatcca  1860

tttctgtatg caatattcac taagacattc caaagagatt tctttctttt gctgagcaaa  1920

tttggctgct gtaaacgtcg ggctgaactt tatagaagga aagatttttc agcttacacc  1980

tccaactgca aaaatggctt cactggatca aataagcctt ctcaatccac cttgaagttg  2040

tccacattgc actgtcaagg tacagctctc ctagacaaga ctcgctacac agagtgtggt  2100

accttgacct gtgatgaccc ccgcttccag gactcctctt cctcaaaggc ccctcccccc  2160

agccttccaa gtccatcccg actcccgggg ccctcggaca ccccgatcct cccacaa     2217
```

The present invention also includes another chimeric human lutropin hormone receptor/human chorionic gonadotropin-β fusion protein. This chimera has a fragment of the human lutropin hormone receptor (SEQ ID NO: 5) and a fragment of the human chorionic gonadotropin-β unit (SEQ ID NO: 7). A small peptide linker consisting of two amino acids, Gly-Thr, is located between the C-terminus of the hLH-R domain and the N-terminus of the hCG-β domain to form a contiguous hLH-R-hCG-β fusion protein (chimera 3). This fusion protein has the amino acid sequence of SEQ ID NO: 15, as follows:

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255
```

-continued

```
Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Gly Thr Leu Thr Cys
            340                 345                 350

Asp Asp Pro Arg Phe Gln Asp Ser Ser Ser Ser Lys Ala Pro Pro Pro
        355                 360                 365

Ser Leu Pro Ser Pro Ser Arg Leu Pro Gly Pro Ser Asp Thr Pro Ile
    370                 375                 380

Leu Pro Gln
385
```

This hLH-R/hCG-β fusion protein of the present invention is encoded by the nucleic acid molecule having the nucleotide sequence of SEQ ID NO: 16, as follows:

```
atgaagcagc ggttctcggc gctgcagctg ctgaagctgc tgctgctgct gcagccgccg     60

ctgccacgag cgctgcgcga ggcgctctgc cctgagccct gcaactgcgt gcccgacggc    120

gccctgcgct gccccggccc cacggccggt ctcactcgac tatcacttgc ctacctccct    180

gtcaaagtga tcccatctca agctttcaga ggacttaatg aggtcataaa aattgaaatc    240

tctcagattg attccctgga aaggatagaa gctaatgcct ttgacaacct cctcaatttg    300

tctgaaatac tgatccagaa caccaaaaat ctgagataca ttgagcccgg agcatttata    360

aatcttcccg gattaaaata cttgagcatc tgtaacacag gcatcagaaa gtttccagat    420

gttacgaagg tcttctcctc tgaatcaaat ttcattctgg aaatttgtga taacttacac    480

ataaccacca taccaggaaa tgcttttcaa gggatgaata atgaatctgt aacactcaaa    540

ctatatggaa atggatttga agaagtacaa agtcatgcat tcaatgggac gacactgact    600

tcactggagc taaaggaaaa cgtacatctg gagaagatgc acaatggagc cttccgtggg    660

gccacagggc cgaaaacctt ggatatttct tccaccaaat tgcaggccct gccgagctat    720

ggcctagagt ccattcagag gctaattgcc acgtcatcct attctctaaa aaaattgcca    780

tcaagagaaa catttgtcaa tctcctggag gccacgttga cttaccccag ccactgctgt    840

gcttttagaa acttgccaac aaaagaacag aatttttcac attccatttc tgaaaacttt    900

tccaaacaat gtgaaagcac agtaagg~aa gtgagtaaca aaacacttta ttcttccatg    960

cttgctgaga gtgaactgag tggctgggac tatgaatatg gtttctgctt acccaagaca   1020

ccccgatgtg ctcctgaacc aggtaccttg acctgtgatg acccccgctt ccaggactcc   1080

tcttcctcaa aggcccctcc ccccagcctt ccaagtccat cccgactccc ggggccctcg   1140

gacaccccga tcctcccaca a                                              1161
```

The present invention relates to yet another chimeric hLH-R/hCG-β fusion protein having a fragment of the human lutropin hormone receptor (SEQ ID NO: 5) and the full length human chorionic gonadotropin-β unit (SEQ ID NO: 3). A small peptide linker consisting of two amino acids, Gly-Thr, is located between the C-terminus of the hLH-R domain and the N-terminus of the hCG-β domain to form a contiguous hLH-R-hCG-β fusion protein. This fusion protein has the amino acid sequence of SEQ ID NO: 17 (chimera 4), as follows:

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Gly Thr Met Glu Met
            340                 345                 350

Phe Gln Gly Leu Leu Leu Leu Leu Leu Leu Ser Met Gly Gly Thr Trp
        355                 360                 365

Ala Ser Lys Glu Pro Leu Arg Pro Arg Cys Arg Pro Ile Asn Ala Thr
    370                 375                 380
```

-continued

```
Leu Ala Val Glu Lys Glu Gly Cys Pro Val Cys Ile Thr Val Asn Thr
385                 390                 395                 400

Thr Ile Cys Ala Gly Tyr Cys Pro Thr Met Thr Arg Val Leu Gln Gly
                405                 410                 415

Val Leu Pro Ala Leu Pro Gln Val Val Cys Asn Tyr Arg Asp Val Arg
            420                 425                 430

Phe Glu Ser Ile Arg Leu Pro Gly Cys Pro Arg Gly Val Asn Pro Val
        435                 440                 445

Val Ser Tyr Ala Val Ala Leu Ser Cys Gln Cys Ala Leu Cys Arg Arg
    450                 455                 460

Ser Thr Thr Asp Cys Gly Gly Pro Lys Asp His Pro Leu Thr Cys Asp
465                 470                 475                 480

Asp Pro Arg Phe Gln Asp Ser Ser Ser Ser Lys Ala Pro Pro Pro Ser
                485                 490                 495

Leu Pro Ser Pro Ser Arg Leu Pro Gly Pro Ser Asp Thr Pro Ile Leu
            500                 505                 510

Pro Gln
```

This chimeric hLH-R/hCG-β fusion protein of the present invention is encoded by a nucleic acid molecule having the nucleotide sequence of SEQ ID NO: 18, as follows:

```
atgaagcagc ggttctcggc gctgcagctg ctgaagctgc tgctgctgct gcagccgccg    60

ctgccacgag cgctgcgcga ggcgctctgc cctgagccct gcaactgcgt gcccgacggc   120

gccctgcgct gccccggccc cacggccggt ctcactcgac tatcacttgc ctacctccct   180

gtcaaagtga tcccatctca agctttcaga ggacttaatg aggtcataaa aattgaaatc   240

tctcagattg attccctgga aaggatagaa gctaatgcct ttgacaacct cctcaatttg   300

tctgaaatac tgatccagaa caccaaaaat ctgagataca ttgagcccgg agcatttata   360

aatcttcccg gattaaaata cttgagcatc tgtaacacag gcatcagaaa gtttccagat   420

gttacgaagg tcttctcctc tgaatcaaat ttcattctgg aaatttgtga taacttacac   480

ataaccacca taccaggaaa tgcttttcaa gggatgaata atgaatctgt aacactcaaa   540

ctatatggaa atggatttga agaagtacaa agtcatgcat tcaatgggac gacactgact   600

tcactggagc taaaggaaaa cgtacatctg gagaagatgc acaatggagc cttccgtggg   660

gccacagggc cgaaaacctt ggatatttct tccaccaaat tgcaggccct gccgagctat   720

ggcctagagt ccattcagag gctaattgcc acgtcatcct attctctaaa aaaattgcca   780

tcaagagaaa catttgtcaa tctcctggag gccacgttga cttaccccag ccactgctgt   840

gcttttagaa acttgccaac aaaagaacag aatttttcac attccatttc tgaaaacttt   900

tccaaacaat gtgaaagcac agtaaggaaa gtgagtaaca aaacacttta ttcttccatg   960

cttgctgaga gtgaactgag tggctgggac tatgaatatg gtttctgctt acccaagaca  1020

ccccgatgtg ctcctgaacc aggtaccatg gagatgttcc aggggctgct gctgttgctg  1080

ctgctgagca tgggcgggac atgggcatcc aaggagccgc ttcggccacg gtgccgcccc  1140

atcaatgcca ccctggctgt ggagaaggag ggctgccccg tgtgcatcac cgtcaacacc  1200

accatctgtg ccggctactg ccccaccatg acccgcgtgc tgcagggggt cctgccggcc  1260

ctgcctcagg tggtgtgcaa ctaccgcgat gtgcgcttcg agtccatccg gctccctggc  1320

tgcccgcgcg gcgtgaaccc cgtggtctcc tacgccgtgg ctctcagctg tcaatgtgca  1380
```

-continued

```
ctctgccgcc gcagcaccac tgactgcggg ggtcccaagg accacccctt gacctgtgat  1440

gacccccgct tccaggactc ctcttcctca aaggcccctc cccccagcct tccaagtcca  1500

tcccgactcc cggggccctc ggacaccccg atcctcccac aa                      1542
```

In all aspects of the present invention shown above, the two domains of the chimeric hLH-R/hCG-β fusion protein are joined via a peptide linker. The linkers are used to facilitate manipulation of the two proteins in forming the chimera (as described in detail in Example 1), and are not meant to be limiting in either number or identity. Any other linkers, i.e., amino acids, or combinations thereof, may be substituted in the fusion protein of the present invention, provided they do not interfere with the native properties of the two domains of the fusion protein, including the antigenic properties thereof.

The chimeric nucleic acid molecules encoding the fusion proteins of the present invention are prepared using well-known recombinant technology. This involves, briefly, isolating the desired nucleic acid molecule encoding a full-length human lutropin hormone receptor, or a fragment thereof, and the desired nucleic acid molecule encoding a human chorionic gonadotropin-β subunit, or fragment thereof, and cloning the desired nucleic acid molecules into a single vector, and adding additional nucleotides encoding the desired amino acid linker sequence between the 3' end of the hLH-R coding sequence and the 5' end of the hCG-β subunit coding sequence. The preparation of the desired embodiment of the chimeric nucleic acid molecule of present invention is carried out using standard cloning procedures, such as described in Sambrook et al., *Molecular Cloning: A Laboratory Manual* Cold Springs Laboratory, Cold Springs Harbor, N.Y. (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); Plant Molecular Biology: A Laboratory Manual, Clark, Ed., Springer-Verlag, Berlin (1997), which are hereby incorporated by reference in their entirety.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim, Indianapolis, Ind.) can be used to improve yield of long PCR products. PCR-based screening methods have been described. Alphey, L., "PCR-Based Method for Isolation of Full-Length Clones and Splice Variants from cDNA Libraries," *BioTechniques* 22(3):481-484 (1997) (which is hereby incorporated by reference in its entirety), describes a PCR-based method in which the longest cDNA is identified in the first step so that incomplete clones can be eliminated from study. Such methods are particularly effective in combination with a full-length cDNA construction methodology.

The isolated nucleic acids of the present invention can also be prepared by direct chemical synthesis using methods such as the phosphotriester method of Narang et al., "Improved Phosphotriester Method for the Synthesis of Gene Fragments," *Methods Enzymol* 68:90-98 (1979) (which is hereby incorporated by reference in its entirety), the phosphodiester method of Brown et al., "Chemical Synthesis and Cloning of a Tyrosine tRNA Gene," *Methods Enzymol* 68:109-51 (1979) (which is hereby incorporated by reference in its entirety), using an automated synthesizer, e.g., as described in Needham-VanDevanter et al., "Characterization of an Adduct Between CC-1065 and a Defined Oligodeoxynucleotide Duplex," *Nucleic Acids Res* 12(15):6159-6168 (1984) (which is hereby incorporated by reference in their entirety), and the solid support method of U.S. Pat. No. 4,458,066 to Caruthers et al., (which is hereby incorporated by reference in its entirety). Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

In one aspect of the present invention, a chimeric nucleic acid molecule encoding a hLH-R/hCG-β fusion protein is introduced into an expression system or expression vector of choice, creating a nucleic acid construct using conventional recombinant technology. Generally, this involves inserting the chimeric nucleic acid molecule of the present invention into an expression system to which the molecule is heterologous (i.e., not normally present). The heterologous nucleic acid molecule is inserted into the expression system or vector in proper sense (5'→3') orientation and correct reading frame. The vector contains the necessary 5' and 3' region elements for the proper transcription and translation of the inserted protein-coding sequences. In preparing the nucleic acid construct of the present invention, the various nucleic acid molecules of the present invention may be inserted or substituted into a bacterial plasmid-vector. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for transformation. Suitable vectors include, but are not limited to, the following: viral vectors, such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et al., "Use of T7 RNA Polymerase to Direct Expression of Cloned Genes," *Gene Expression Technology vol.* 185 (1990), which is hereby incorporated by reference in its entirety), and any derivatives thereof.

Certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. Common 5' regulatory regions, including, but not limited to promoters, suitable for directing expression in mammalian cells include the SV40, MMTV, metallothionein-1, adenovirus Ela, CMV, immediate early, immunoglobulin heavy chain promoter and enhancer, and RSV-LTR promoters. The selection of a regulatory regions will be influenced by the host species selected so expression in the host is effected.

The nucleic construct of the present invention also includes an operable 3' regulatory region, selected from among those which are capable of providing correct transcription termination and polyadenylation of mRNA for expression in the host of choice. The 5' and 3' regulatory regions are operably linked to a DNA molecule, thereby allowing expression of the protein or polypeptide encoded by the DNA molecule of choice.

The nucleic acid molecule of the present invention, appropriate transcriptional and translational regulatory elements, and any additional desired components, including without limitation, enhancers, leader sequences, markers, reporter genes, etc., are cloned into the vector of choice using standard cloning procedures in the art, such as described in Sambrook et al., *Molecular Cloning: A Laboratory Manual* Cold Springs Laboratory, Cold Springs Harbor, N.Y. (1989), and U.S. Pat. No. 4,237,224 to Cohen and Boyer, which are hereby incorporated by reference in their entirety. The transcriptional and translational elements are operably linked to the nucleic acid molecule of the present invention or a fragment thereof, meaning that the resulting vector expresses the human lutropin hormone receptor/human chorionic gonadotropin-β fusion protein of the present invention when placed in a suitable host.

Once the chimeric nucleic acid molecule encoding the hLH-R/hCG-β fusion protein of the present invention has been cloned into an expression system, it is ready to be incorporated into a host. Accordingly, another aspect of the present invention relates to a method of making a recombinant host. Basically, this method is carried out by transforming a host with a nucleic acid construct of the present invention under conditions effective to yield transcription of the nucleic acid molecule in the host. Such incorporation can be carried out in a variety of ways, depending upon the vector/host system. Recombinant molecules can be introduced into a host via transformation, transduction, conjugation, mobilization, or electroporation. Preferably, the nucleic acid construct of the present invention is stably inserted into the genome of the recombinant host as a result of the transformation. Suitable hosts for the chimeric nucleic acid molecule of the present invention include, but are not limited to, bacteria, virus, yeast, insect cells, and mammalian cells, including canine, feline, and human.

Transient expression in protoplasts allows quantitative studies of gene expression since the population of cells is very high (on the order of $10^6$). To deliver DNA inside protoplasts, several methodologies have been proposed, but the most common are electroporation (Neumann et al., "Gene Transfer into Mouse Lyoma Cells by Electroporation in High Electric Fields," *EMBO J.* 1: 841-45 (1982); Wong et al., "Electric Field Mediated Gene Transfer," *Biochem Biophys Res Commun* 30;107(2):584-7 (1982); Potter et al., "Enhancer-Dependent Expression of Human Kappa Immunoglobulin Genes Introduced into Mouse pre-B Lymphocytes by Electroporation," *Proc. Natl. Acad. Sci. USA* 81: 7161-65 (1984), which are hereby incorporated by reference in their entirety) and polyethylene glycol (PEG) mediated DNA uptake, Sambrook et al., *Molecular Cloning: A Laboratory Manual* Chap. 16, 2d Edition, Cold Springs Laboratory, Cold Springs Harbor, N.Y. (1989), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., "Liposome-Mediated Delivery of Tobacco Mosaic Virus RNA Into Tobacco Protoplasts: A Sensitive Assay for Monitoring Liposome-Protoplast Interactions," *Proc Natl Acad Sci USA* 79:1859-63 (1982); Horsch et al., "A Simple and General Method for Transferring Genes into Plants," *Science* 227:1229-1231 (1985), which are hereby incorporated by reference in their entirety).

Stable transformants are preferable for the methods of the present invention, which can be achieved by using variations of the methods above as described in Sambrook et al., *Molecular Cloning: A Laboratory Manual* Chap. 16, Second Edition, Cold Springs Laboratory, Cold Springs Harbor, N.Y. (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); which are hereby incorporated by reference in their entirety.

Typically, when a recombinant host is grown for the purpose producing/expressing the desired recombinant protein, an antibiotic or other compound useful for selective growth of the transgenic cells only is added as a supplement to the media. The compound to be used will be dictated by the selectable marker element present in the plasmid with which the host cell was transformed. Suitable genes are those which confer resistance to gentamycin, G418, hygromycin, streptomycin, spectinomycin, tetracycline, chloramphenicol, and the like. When the host is to be a mammalian cell, in particular a human cell, kanamycin is highly suitable. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from Aequorea victoria (Prasher et al., "Primary Structure of the Aequorea Victoria Green-Fluorescent Protein," *Gene* 111(2):229-233 (1992); U.S. Pat. No. 5,491,084 to Chalfie et al., which are hereby incorporated by reference in their entirety). A plasmid encoding the GFP of Aequorea victoria is available from the ATCC as Accession No. 75547. Mutated forms of GFP that emit more strongly than the native protein, as well as forms of GFP amenable to stable translation in higher vertebrates, are commercially available from Clontech Laboratories, Inc. (Palo Alto, Calif.) and can be used for the same purpose. The plasmid designated pTα1-GFPh (ATCC Accession No. 98299, which is hereby incorporated by reference in its entirety) includes a humanized form of GFP. Indeed, any nucleic acid molecule encoding a fluorescent form of GFP can be used in accordance with the subject invention. Standard techniques are then used to place the nucleic acid molecule encoding GFP under the control of the chosen cell specific promoter.

The selection marker employed will depend on the target species and/or host or packaging cell lines compatible with a chosen vector.

Following introduction into a host, the host is grown under conditions appropriate for the selection of hosts harboring the chimeric transgene. The expression of the hLH-R/hCG-β fusion protein of the present invention by apparently transgenic hosts can be determined by carrying out screening techniques described herein below, and those hosts expressing the chimeric fusion protein are propagated and expanded under suitable culture conditions.

The present invention also relates to an isolated recombinant hLH-R/hCG-β fusion protein. Recombinant human lutropin hormone receptor/human chorionic gonadotropin-β fusion proteins of the present invention include, without limitation, the proteins having amino acid sequences of SEQ ID NO:11, 13, 15, and 17, shown herein above. The recombinant fusion protein of the present invention is secreted into the growth medium of transgenic host, for example, *E. coli*, harboring a nucleic acid molecule encoding a human lutropin hormone receptor/human chorionic gonadotropin-β fusion protein. To isolate the desired protein, host carrying a chimeric transgene is propagated, collected, homogenized, and the homogenate is centrifuged to remove bacterial debris. The supernatant is then subjected to sequential ammonium sulfate precipitation. The fraction containing the desired protein of the present invention is subjected to gel filtration in an appropriately sized dextran or polyacrylamide column to separate the proteins. If necessary, the protein fraction may be further purified by HPLC or other chromatography techniques, for example, metal affinity chromatography. Alternative protein isolation methods known in the art may be used as suitable.

The present invention also encompasses chimeric hLH-R/hCG-β fusion proteins that are functionally equivalent variants of the proteins having SEQ ID NO:11, 13, 15, and 17. By "variant protein" is intended a protein derived from the native protein by deletion (so-called truncation) or addition of one or more amino acids to the N-terminal and/or C-terminal end of the native protein deletion or addition of one or more amino acids at one or more sites in the native protein, or substitution of one or more amino acids at one or more sites in the native protein. Variant proteins encompassed by the present invention are biologically active, that is, they continue to possess the desired biological activity of the native protein. In particular, the variant protein will have the antigenic properties of the native proteins as described herein. Such variants may result from, for example, genetic polymorphism or from human manipulation. Biologically active variants of any hLH-R/hCG-β fusion protein of the invention described herein will have at least about 90%, 91%, 92%, 93%, 94%, 95%, 96%, 97% and preferably about 98% sequence similarity to the amino acid sequence for a fusion protein described herein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the proteins pf the invention can be prepared by mutations in the DNA. Methods for mutagenesis and nucleotide sequence alterations are well known in the art (Kunkel, T. A., "Rapid and Efficient Site-Specific Mutagenesis Without Phenotypic Selection, *Proc Natl Acad Sci USA* 82(2):488-492 (1985); Kunkel et al., "Rapid and Efficient Site-Specific Mutagenesis Without Phenotypic Selection," *Methods Enzymol* 154:367-382 (1987); U.S. Pat. No. 4,873,192 to Kunkel; Walker and Gaastra, eds., *Techniques in Molecular Biology*, New York: MacMillan Publishing Company (1983) and the references cited therein. Guidance as to appropriate amino acid substitutions that do not affect biological activity of the protein of interest may be found in the model of Dayhoff et al. (1978) *Atlas of protein Sequence and Structure* (*Natl. Biomed. Res. Found.*, Washington, D.C.), herein incorporated by reference in its entirety. Conservative substitutions, such as exchanging one amino acid with another having similar properties, may be preferable. Variant nucleotide sequences and proteins also encompass sequences and proteins derived from a mutagenic and recombinogenic procedure such as DNA shuffling. With such a procedure, one or more different coding sequences of the invention can be manipulated to create a new sequence possessing the desired properties. In this manner, libraries of recombinant polynucleotides are generated from a population of related sequence polynucleotides comprising sequence regions that have substantial sequence identity and can be homologously recombined in vitro or in vivo.

Thus, the chimeric nucleic acid molecules and amino acids of the invention include both the naturally occurring sequences as well as mutant forms. Likewise, the proteins of the invention encompass both naturally occurring proteins as well as variations and modified forms thereof. Obviously, the mutations that will be made in the DNA encoding the variant must not place the sequence out of reading frame and preferably will not create complementary regions that could produce secondary mRNA structure (EP Patent Application Publication No. 75,444 to De Boer, which is hereby incorporated by reference in its entirety). The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. More details regarding routine assays to measure such activity are described in the Examples herein.

A common characteristic of any hLH-R/hCG-β fusion protein of the present invention will be the ability of the protein, when presented as an immunogen, to elicit production of an antibody specifically reactive to one or both protein domains of the hLH-R/hCG-β fusion protein of the present invention. The term "immunogen" is used herein for a substance which elicits the formation of antibodies as described herein above. The term "antigen" denotes a substance which couples with a matching antibody, thereby being bound and "neutralized" by the latter. In practice "antigens" and "immunogens" in a given context are often the same substances, thus, two terms are frequently used, including in the present specification, as synonyms. Likewise, "immunogenic" and "antigenic" are used interchangeably herein.

Furthermore, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay, such as described below in the Examples. Thus, the proteins of the present invention can be employed as immunogens for constructing antibodies immunoreactive to one or both domains of the fusion protein of the present invention, or for such exemplary utilities as immunoassays or protein purification techniques.

Studies in animals have demonstrated that antibodies against LH-R suppress the production of progesterone in the female (Saxena et al., "Modulation of Ovarian Function in Female Dogs Immunized With Bovine Luteinizing Hormone Receptor," *Reprod Domest Anim* 37(1):9-17 (2002) and Saxena et al., "Effect of Immunization with Bovine Luteinizing Hormone Receptor on Ovarian Function in Cats," *Am J Vet Res* 64(3):292-298 (2003), which are hereby incorporated by reference in their entirety), and of testosterone in the male (Remy et al., "Immunization Against Exon 1 Decapeptides From the Lutropin/Choriogonadotropin Receptor or the Follitropin Receptor as Potential Male Contraceptive," *J Reprod Immunol* 32(1):37-54 (1996), which is hereby incorporated by reference in its entirety), leading to infertility. Chimeras of hLH-R combined with hCG and their fragments have the advantage of presenting themselves as heterologous antigens and are likely to mount an enhanced host immune response. Therefore, the present invention also relates to an isolated antibody, or binding portions thereof, raised to the fusion protein(s) of the present invention or proteins having a high sequence identity (as described herein above) or encoded by a nucleic acid molecule having a high sequence identity to the nucleic acid molecules herein. Because the fusion protein of the present invention contains more than one antigen, the fusion protein will likely produce a variety of antibodies when used as an immunogen for antibody formation. In particular, antibodies may be raised that recognize the hLH-R domain, while not recognizing the hCG-β subunit domain; that recognize the hCG-β subunit domain, while not recognizing the hLH-R domain; and that recognize both the hLH-R domain and the hCG-β subunit domain. Each of these antibodies is useful in one or more aspects of the present invention.

Antibodies of the present invention include those which are capable of binding to the fusion protein of the present invention and inhibiting the activity of such a polypeptide or protein, either in vitro (in an assay) or in vivo (i.e., if injected into a subject as an immunogen). In addition, antibodies of the present invention may also bind to a native hHL-R and a hCG-β subunit in vitro and in vivo.

The antibodies of the present invention may be monoclonal or polyclonal. Monoclonal antibody production may be effected by techniques which are well-known in the art (*Monoclonal Antibodies—Production, Engineering and Clinical Applications*, Ritter et al., Eds. Cambridge University Press, Cambridge, UK (1995), which is hereby incorporated by reference in its entirety). Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kunkel et al., "Rapid and Efficient Site-Specific Mutagenesis Without Phenotypic Selection," *Methods Enzymol* 154:367-382 (1987), which is hereby incorporated by reference in its entirety.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Kohler et al., "Derivation of Specific Antibody-Producing Tissue Culture and Tumor Lines by Cell Fusion," *Eur J Immunol* 6(7):511-519 (1976), which is hereby incorporated by reference in its entirety). This immortal cell line, which is preferably murine, but may also be derived from cells of other mammalian species, including without limitation, rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled approximately every two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow, et. al., Eds., *Antibodies: A Laboratory Manual*, Cold Springs Harbor Laboratory, New York (1988), which is hereby incorporated by reference in its entirety. A polyclonal antibody preparation may include antibodies of various specificity, i.e., antibodies that are reactive with the fusion protein per se, with the hLH-R domain, or fragment thereof, or with the hCG-β domain, or fragment thereof, or with the proteins of both domains of the fusion protein.

It is also possible to use the anti-idiotype technology to produce monoclonal antibodies that mimic an epitope. As used in this invention, "epitope" means any antigenic determinant on an antigen to which the paratope of an antibody binds. Epitopic determinants usually consist of chemically active surface groupings of molecules, such as amino acids or sugar side chains and usually have specific three dimensional structural characteristics, as well as specific charge characteristics. For example, an anti-idiotype monoclonal antibody made to a first monoclonal antibody will have a binding domain in the hypervariable region that is the image of the epitope bound by the first monoclonal antibody.

In addition to whole antibodies, the present invention encompasses binding portions of such antibodies. Such binding portions include Fab fragments, $F(ab')_2$ fragments, and Fv fragments. These antibody fragments can be made by conventional procedures, such as proteolytic fragmentation procedures, as described in J. Goding, *Monoclonal Antibodies: Principles and Practice*, pp. 98-118 N.Y. Academic Press (1983), and Harlow et al., *Antibodies: A Laboratory Manual* Cold Springs Harbor Laboratory, New York (1988), which are hereby incorporated by reference in their entirety, or other methods known in the art.

The present invention also relates to antibodies raised as described above, against the full length hHL-R proteins having SEQ ID NO:1 and SEQ ID NO:9, and antibodies raised against any fragments of the hLH-R domain, including, but not limited to the ECD (SEQ ID NO:5). This is meant to include any antibodies raised against variants of these proteins having an amino acid sequence that is at least 80%, 85% or 87%, alternatively at least 92%, 94%, or 96%, and preferably 98% sequence identity to the proteins having SEQ ID NO:1, 5, or 9 of the present invention.

The present invention also relates to a composition including the isolated fusion protein of the present invention having a human lutropin hormone receptor domain and a human chorionic gonadotropin-β domain, and a pharmaceutical carrier. This fusion protein includes a full length human lutropin hormone receptor domain or a fragment thereof, including, but not limited to those describe herein above, and a full length human chorionic gonadotropin-β domain or a fragment thereof, including, but not limited to, those describe herein above. A common characteristic of the fusion protein suitable for such a composition is the immunogenic capability of the protein. Thus, a suitable a hLH-R/hCG-β fusion protein is an isolated hLH-R and/or hCG-β fusion protein as described herein above that is capable of eliciting the formation of antibodies of the present invention as described herein above.

The immunogenic characteristic of the hLH-R/hCG-β fusion protein of the present invention is useful in stimulation of a host's immune response. By "immune response" is meant that antibodies are formed by the immune system in response to an immunogenic stimulus elicited by the immunogen. The antibodies will include antibodies more or less specific to the immunogenic determinants (or combination thereof) of the immunogen. When the immune system of an animal is challenged with an immunogen (e.g., by injection) to produce endogenous antibodies against an antigen having antigenic determinants corresponding to the immunogenic determinants of the immunogen, that is known as active immunization. Thus, the isolated or synthesized fusion protein of the present invention combined with a carrier may be used for the active immunization of a subject. Fusion proteins suitable for this aspect of the present invention include, without limitation, any of the hLH-R/hCG-β fusion proteins described herein above or a suitable variant thereof. The carrier in this aspect of the present invention includes any of a variety of known immunologic adjuvants or pharmaceutical additives that enable or enhance delivery of the fusion protein of the present invention to a subject.

Alternatively, the administration to a subject by injection of antibodies extraneously produced, for example, polyclonal or monoclonal antibodies prepared in a different animal (as described hereinabove) to produce resistance against antigens for which the antibodies are specific, is known as passive immunization. Thus, another aspect of the present invention is a composition having a pharmaceutical carrier and an antibody to any of the hLH-R/hCG-β fusion proteins as described herein, or a suitable variant thereof. A suitable antibody of this aspect of the present invention may be a monoclonal or polyclonal antibody or a binding portion thereof, prepared as described herein, and where the administration of the composition is as described herein below.

In addition, immunological preparations comprising antibodies to the hLH-R/hCG-β fusion protein of the present invention can be put to a variety of uses, including, without limitation, as immunoreagents for immunosorbtive processes and for quantitative and qualitative analytical tests, in particular, assays for diagnostic, pathological, forensic, and pharmacokinetic investigations involving hLH-R and hCG-β proteins and reproduction.

The present invention also relates to a method of treating an androgen-excess-mediated disease condition in a subject. This involves administering an antibody to the hLH-R/hCG-β fusion protein of the present invention to the subject under conditions effective to treat the androgen-excess-mediated disease condition. For females, an antibody recognizing both the h-LH-R and the hCG domains, i.e., antibody raised to chimera 1, 2, 3, and 4, as well as a mix of antibodies, where some of the antibodies recognize the h-LH-R domain and some recognize the hCG-β domain, are suitable for treatment of an androgen-excess-mediated condition. However, males do not produce hCG. Therefore, an antibody that recognizes the LH-R in males is sufficient for treatment of an androgen-excess mediated disease condition. However, if a male is immunized with an antibody that recognizes both the hLH-R and the hCG domains, the presence of the antibody to the hCG domain may act as a "mock domain," or a hapten, thereby enhancing the effect of the anti-hLH-R treatment. If an antibody is administered to males that includes a recognition site for hCG, it is preferable that it be only the CTP fragment of the hCG-β-subunit. This includes, for example, antibodies to proteins having amino acid sequences of SEQ ID NO: 11 and SEQ ID NO:13 of the present invention. Alternatively, antibodies that recognize only the hLH-R domain of the hLH-R/h hCG-β fusion protein of the present invention and antibodies raised to an hLH-R protein alone are also suitable for administration to males in this aspect of the present invention.

Administration in this and all aspects of the present invention may be carried out orally, parenterally, subcutaneously, intravenously, intramuscularly, intraperitoneally, intravaginally, by intranasal instillation, by intracavitary or intravesical instillation, intraocularly, intraarterially, intralesionally, or by application to mucous membranes, such as, that of the nose, throat, and bronchial tubes. The antibody to the hLH-R/hCG-β fusion protein may be administered alone or with pharmaceutically or physiologically acceptable carriers, excipients, or stabilizers, and can be in solid or liquid form including tablets, capsules, powders, solutions, suspensions, or emulsions.

The solid unit dosage forms can be of the conventional type. The solid form can be a capsule, such as an ordinary gelatin type containing the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The antibodies to the hLH-R/hCG-β fusion protein of the present invention may also be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the antibodies of the present invention in solution or suspension may be packaged in a pressurized aerosol container together with suitable propellants, for example, hydrocarbon propellants like propane, butane, or isobutane with conventional adjuvants. The antibodies of the present invention also may be administered in a non-pressurized form such as in a nebulizer or atomizer.

In this aspect of the present invention the antibodies may be administered for treatment of various conditions known as androgen-excess syndromes, including, without limitation, polycystic ovarian syndrome, Klinefelter's Syndrome, and prostatic hyperplasia. Suitable subjects in this aspect of the present invention are any mammals, including canine, feline, and human, and may be either the male or the female of the species.

Another aspect of the present invention is a method of immunocontraception in a subject that involves administering an antibody to hLH-R/hCG-β fusion protein of the present invention to a subject under conditions effective to provide immunocontraception to the subject. Suitable for this aspect of the present invention are a mix of antibodies, where some of the antibodies recognize the hLH-R domain, and others recognize the hCG domains. When the subject is female, the preferable antibody of this aspect is an antibody capable of recognizing both the hLH-R domain and the/ hCG-β domain of the fusion protein of the present invention. When the subject is a male, the antibody or antibodies administered are preferably those that recognize the hLH-R only, either the full-length domain (e.g., SEQ ID NO: 1 and 9) or a fragment thereof (e.g., SEQ ID NO:5), or an hLH-R/hCG hCG-β fusion protein, where the hLH-R is either full-length or a fragment thereof, and the hCG-β domain is the CTP fragment (e.g., SEQ ID NO:13, 15. Because males do not produce the chorionic gonadotropin hormone, immunocontraception can be conferred to males using an hLH-R antibody alone When the antibody used in males also recognizes the CTP fragment of the hCG-β subunit, the CTP antibody serves as a hapten to enhance the immunocontraceptive affect of the hLH-R antibody. Administration of an antibodies in this aspect of the present invention is carried out as described above. Suitable subjects for this aspect of the present invention include those described above.

The present invention also relates to a method of immunocontraception that involves administering the human lutropin hormone receptor/human chorionic gonadotropin-β fusion protein of the present invention to a subject under conditions effective to provide immunocontraception to the subject. Any of the hLH-R/hCG-β fusion proteins described herein that are immunogenic as described above are suitable in this aspect of the present invention. Administration of the fusion protein of the present invention is carried out as described above. Suitable subjects for this aspect of the present invention include those described above.

Yet another method of immunocontraception is provided in the present invention. This method involves administering the chimeric nucleic acid molecule of the present invention that encodes a human lutropin hormone receptor/human chorionic gonadotropin-β fusion protein to a subject under conditions effective to provide immunocontraception to the subject. This is a type of active immunization known as a "DNA vaccine." DNA vaccines, an alternative approach to standard immunization methods, induce both cellular and humoral immune responses in a subject. Due to advances in molecular biology techniques, DNA vaccines have become a reliable and major means to elicit immune responses in the past decade (Sasaki et al., "Adjuvant Formulations and Delivery Systems for DNA Vaccines," *Methods* 31 (3):243-254 (2003); Amon et al., "Old and New Vaccine Approaches," *Int Immunopharmacol* 3(8):1195-1204 (2003); Garmony et al., "DNA Vaccines: Improving Expression of Antigens," *Genetic Vaccines and Therapy* 1(1):2 (2003); which are hereby incorporated by reference in their entirety). A DNA vaccine is used to induce an immune response to an antigen protein expressed in vivo. It is based on the introduction of a purified DNA plasmid encoding for a chosen immunogenic protein or polypeptide sequence into subject. This involves, generally, the development of recombinant, or genetically engineered, live vector (virus or bacterium), capable of expressing the antigen and presenting the relevant protective antigen in vivo (Sasaki et al., "Adjuvant Formulations and Delivery Systems for DNA Vaccines," *Methods* 31 (3):243-254 (2003), which is hereby incorporated by reference in its entirety).

DNA vaccines generally consist of plasmid vectors (derived from bacteria) or viral vectors, that contain heterologous genes (transgenes) inserted under the control of a eukaryotic promoter, allowing expression of the gene product in mammalian cells (Garmony et al., "DNA Vaccines: Improving Expression of Antigens," *Genetic Vaccines and Therapy* 1(1):2 (2003), which is hereby incorporated by reference in its entirety). The basic requirements of a plasmid DNA vector are a eukaryotic promoter, a cloning site, a polyadenylation sequence, a selectable marker, and a bacterial origin of replication. A strong promoter may be required for expression in mammalian cells. Suitable strong promoters for this aspect of the present invention include, without limitation, the cytomegalovirus (CMV) or simian virus 40 (SV40) promoters. Tissue-specific promoters are also suitable. A cloning site downstream of the promoter is provided for the insertion of the desired heterologous nucleic acid molecule. Also included in the DNA vaccine plasmid of the present invention are a 3' polyadenylation sequence such as the bovine growth hormone (BGH) or SV40 polyadenylation sequence provides stabilization of mRNA transcripts, and is a selectable marker, usually a bacterial resistance gene. For use in mammals, especially humans, kanamycin is highly suitable. Suitable nucleic acid molecules for this aspect of the present invention includes all of the chimeric nucleic acid molecules described herein above. The making of this plasmid vector is as described in greater detail herein above, or as described in Garmony et al., "DNA Vaccines: Improving Expression of Antigens," Genetic Vaccines and Therapy 1(1):2 (2003); Sambrook et al., *Molecular Cloning: A Laboratory Manual Cold* Springs Laboratory, Cold Springs Harbor, N.Y. (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); which are hereby incorporated by reference in their entirety.

Due to advances in recombinant technology, it is now possible to undertake a rational approach to DNA vaccine design (Garmony et al., "DNA Vaccines: Improving Expression of Antigens," *Genetic Vaccines and Therapy* 1(1):2

(2003), which is hereby incorporated by reference in its entirety). In addition to the basic vector preparation described hereinabove, strategies may include the incorporation of immunostimulatory sequences in the backbone of the plasmid, co-expression of stimulatory molecules, utilization of localization/secretory signals, and utilization of the appropriate delivery system (Garmony et al., "DNA Vaccines: Improving Expression of Antigens," *Genetic Vaccines and Therapy* 1(1):2 (2003), which is hereby incorporated by reference in its entirety).

The majority of DNA vaccines are administered parenterally (Hobson et al., "Mucosal Immunization with DNA Vaccines," *Methods* 31(3):217-224 (2003), which is hereby incorporated by reference in its entirety), however, all other methods of administration as described herein above are also suitable. In particular, the DNA vaccine may be administered in a formulation including microparticles, which allows the co-delivery of the antigen-producing plasmid and an appropriate immunostimulant combined with the microparticle (O'Hagan et al., "Microparticles as Vaccine Adjuvants and Delivery Systems," *Expert Rev Vaccines* 2(2):269-283 (2003), which is hereby incorporated by reference in its entirety); using a particle-mediated ("gene gun") or other epidermal delivery systems (Chen et al., "Needle-Free Epidermal Powder Immunization," *Expert Rev Vaccines* 1(3): 265-276 (2002); Haynes, J. R., "Particle-Mediated DNA Vaccine Delivery to the Skin," *Expert Opin Biol Ther* 4(6):889-900 (2004), which are hereby incorporated by reference in their entirety); topical administration (Choi et al., "Topical Vaccination of DNA Antigens: Topical Delivery of DNA Antigens," *Skin Pharmacol Appl Skin Physiol* 16(5):271-282 (2003), which is hereby incorporated by reference in its entirety); delivery to mucosal membranes (O'Hagan et al., "Microparticles as Vaccine Adjuvants and Delivery Systems," *Expert Rev Vaccines* 2(2):269-283 (2003); Hobson et al., "Mucosal Immunization with DNA Vaccines," *Methods* 31(3):217-224 (2003), which are hereby incorporated by reference in their entirety); and any of the oral delivery systems now being designed and perfected particularly for the delivery of DNA vaccines (e.g., Sheu et al., "The Gene Pill and its Therapeutic Applications," *Curr Opin Mol Ther* 5(4):420-427 (2003) which is hereby incorporated by reference in its entirety). The DNA vaccines having the nucleic acid molecules of the present invention may also include an adjuvant, either as a carrier for delivery or for immunostimulatory purposes, including, but not limited to those described above, as well as any others known in the art (Sasaki et al., "Adjuvant Formulations and Delivery Systems for DNA Vaccines," *Methods* 31(3):243-254 (2003), which is hereby incorporated by reference in its entirety). Suitable subjects, and suitable disease targets for this aspect of the present invention include those described herein above.

EXAMPLES

Example 1

Figure 1:
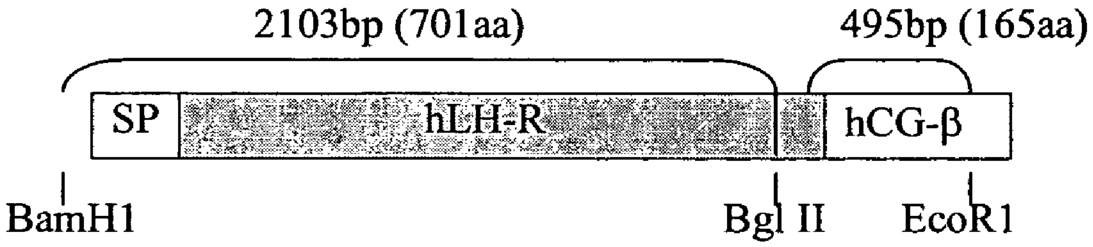
FIG. 1 is a schematic diagram of the chimeric hLH-R-hCG-β nucleic acid molecule of the present invention. Full-length hCG-β with signal peptide is linked via two amino acids at the C-terminal of hLH-R. The N-terminus of hLH-R contains the signal peptide (SP) of hLH-R.

Synthesis of Chimeric hLH-R/hCG-β Full-Length/Full-Length Nucleic Acid Construct Since hLH-R and hCG-β have extensive structural and functional interspecies relationships, DNA sequence from human genome of hLH-R and hCG-β was used to prepare the chimeric nucleic acid molecule(s) of the present invention. To prepare chimera 1 of the present invention, a full-length hLH-R nucleic acid fragment containing 2103 bp (SEQ ID NO: 2) with signal peptide in the vector pSG5-hLH-R, as the template, was amplified by PCR (Atger et al., "Structure of the Human Luteinizing Hormone-Choriogonadotropin Receptor Gene: Unusual Promoter and 5' Non-Coding Regions," *Mol Cell Endocrinol* 111(2):113-123 (1995), which is hereby incorporated by reference in its entirety). The PCR product was cloned into the transfer vector pBlueBac4.5/V5-His (Invitrogen, Carlsbad, Calif.) using BamHI and Bgl II restriction sites, which were inserted by PCR at 5' primer and 3' primer, respectively. Full-length hCG-β DNA with signal peptide containing 495 bp (SEQ ID NO:4) (Lobel et al., "Expression and Characterization of Recombinant Beta-Subunit hCG Homodimer," *Endocrin* 10(3):261-270 (1999), which is hereby incorporated by reference in its entirety) was also amplified by PCR, and two restriction enzyme sites, Bgl II and EcoRI, were introduced at 5' primer and 3' primer. The hCG-β was directly cloned into the pBlueBac4.5/V5-His vector, and then fused to hLH-R by subcloning into the pBlueBac4.5/V5-His+hLHR vector. Two amino acids (Arg and Ser) were inserted between the C-terminus of the hLH-R nucleotide sequence and the N-terminus of the hCG-β nucleotide sequence to form a contiguous BamHI-hLH-R-BglII-hCG-β-EcoRI fusion. The chimeric gene thus consisted of a total of 2604 bp ((SEQ ID NO: 12). The construct is shown schematically in FIG. 1.

Figure 2:
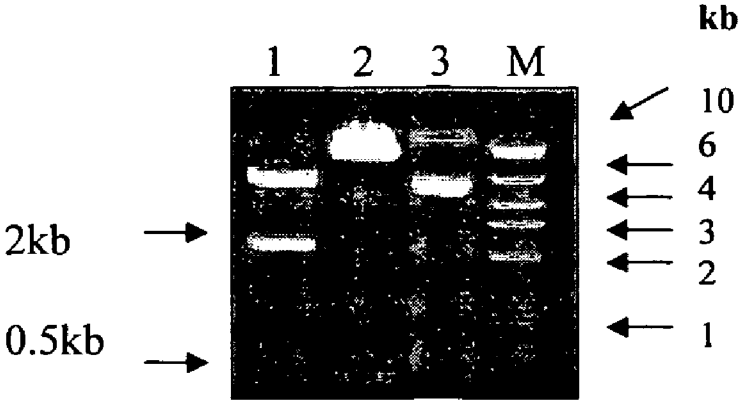
FIG. 2 shows an agarose gel electrophoresis of nucleic acid constructs before and after enzyme digestion of vector containing chimeric construct of full length cDNA of hLH-R and hCG-β. Lane 1: vector pBlueBac+hLH-R+hCG-β digested with BamHI, Bgl II, and EcoRI. Lane 2: vector pBlueBac+hLH-R+hCG-β digested with Bgl II and EcoRI. Lane 3: vector pBlueBac+hLH-R+hCG-β without enzyme digestion. M: DNA size markers.

The recombinant clones were identified by restriction enzyme digestion of the nucleic acid molecule and sequenced from both 5' and 3' ends to ensure that no mutation occurred during the PCR amplification. After the clone was digested with BamHI, BglII and EcoRI, the agarose gel electrophoresis showed three bands of molecular size 5 kb, 2 kb and 0.5 kb, shown in FIG. 2, lane 1, corresponding to the vector pBlueBac4.5/V5-His, hLH-R and hCG-β respectively. In contrast, in FIG. 2, lane 2, two bands of 7 kb and 0.5 kb were visible after the clone was digested with Bgl II and EcoRI corresponding to the hLH-R with vector and hCG-β. These results confirmed the DNA integrity of hLH-R, hCG-β and the full-length/full length hLH-R/hCG-β chimera.

Example 2

Expression of hLH-R/hCG-β Chimeric Nucleic Acid Molecule in Baculovirus System and Detection of Fusion Protein by Western Blots The chimeric gene containing both full-length hLH-R and full-length hCG-β (SEQ ID NO:12) formed a single polypeptide chain consisting of 868 amino acids (SEQ ID NO:11) including two amino acids, Arg and Ser, as a linker between the C-terminus of the hLH-R and the N-terminus of hCG-β. The recombinant fusion protein was identified by western blots using polyclonal antibody raised in the rabbit to LH receptor and antibody to hCG-β (Pal et al., "Active Immunization of Baboons (*Papio anubis*) with the Bovine LH Receptor," *J Reprod Immunol* 21(2):163-174 (1992); Pal et al., "Biological Actions of Monoclonal Antibodies to Bovine Lutropin Receptor," *J Reprod Immunol* 22(1):103 (1992) which are hereby incorporated by reference in their entirety). Sf9 insect cells were grown in monolayers at 27° C. in Complete Grace's medium supplemented with 10% fetal calf serum and 10 mg/ml Gentamycin (Invitrogen, Carlsbad, Calif.). Individual recombinant pBlueBac4.5 transfer vectors were co-transfected with linearized Bac-N-Blue™ viral DNA (Invitrogen, Carlsbad, Calif.) into Sf9 insect cells in the presence of Cellfectin (Invitrogen, Carlsbad, Calif.). The recombinant baculovirus was purified by plaque assay. Blue putative recombinant plaques were transferred to 12-well microtiter plates and amplified in Sf9 cells. Approximately $2.5\times10^6$ cells were seeded in 60 mm dishes, and the virus was added with a multiplicity of infection (MOI) of 5.0 and incubated at 27° C. for 72 hrs. Cell pellets and culture medium were collected after 72 hrs by centrifugation. The cell pellets were washed twice in PBS buffer (Bio-Rad, Hercules, Calif.) to remove the serum proteins. The cells were then solubilized by boiling in lysis buffer ($1\times10^6$ cells per 100 μl) as previously described (Dattatreyamurty et al., "Isolation of the Luteinizing Hormone-Chorionic Gonadotropin Receptor in High Yield from Bovine Corpora Lutea Molecular Assembly and Oligomeric Nature," *J Biol Chem* 258(5):3140-3158 (1983) and Khan et al., "Purification and Properties of Human Chorionic Gonadotropin/Lutropin Receptor from Plasma-Membrane and Soluble Fractions of Bovine Corpora Lutea," *Biochem J* 197(1):7-22 (1981), which are hereby incorporated by reference in their entirety). The supernatant was boiled for 5 min. in electrophoresis sample buffer containing 62.5 mM Tris-HCl, pH 6.8, 25% glycerol, 2% SDS and 5% β-mercaptoethanol. The solubilized membrane proteins were analyzed by gel-electrophoresis in 7.5% SDS-polyacrylamide under reducing conditions for western blot analyses. Protein bands were transferred electrophoretically from the gel to the polyvinylidene difluoride (PVDF) membrane (Bio-Rad, Hercules, Calif.). The membrane was probed for the presence of both hLH-R and hCG-β using polyclonal antibodies. All blots were visualized by chemiluminescence via a secondary horseradish peroxidase-labeled anti-rabbit/anti-mouse antibody according to the manufacturer's instructions (Bio-Rad, Hercules, Calif.).

Figure 3:
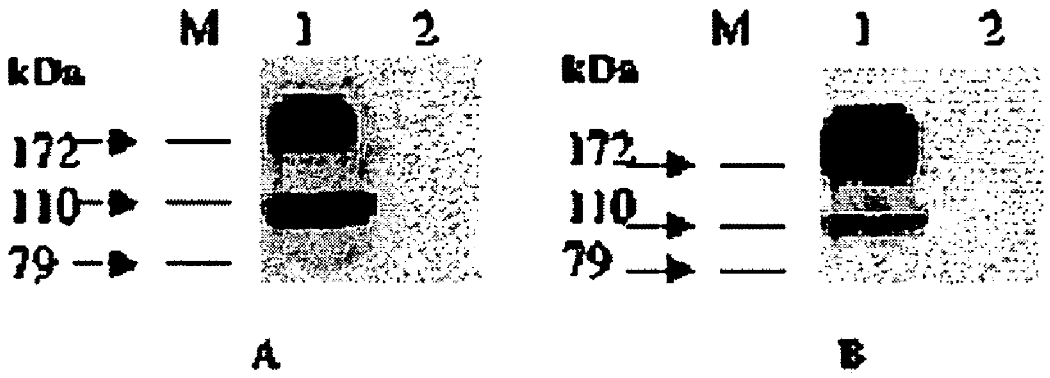
FIGS. 3A-B are western blots of solubilized membrane proteins from Sf9 cells transfected with the hLH-R-hCG-β chimeric construct. Sf9 cells transfected by recombinant baculovirus were collected after 72 hrs of transfection. Sixty μg of solubilized membrane proteins were separated on a 7.5% SDS-PAGE under reducing conditions.

As shown in FIG. 3A, two bands with molecular weights of greater than 172 kD and 110 kD were detected using rabbit polyclonal antibody to LH-R (Pal et al., "Active immunization of Baboons (*Papio anubis*) with the Bovine LH Receptor," *J Reprod Immunol* 21(2):163-174 (1992); Pal et al., "Biological Actions of Monoclonal Antibodies to Bovine Lutropin Receptor," *J Reprod Immunol* 22(l):103 (1992), which are hereby incorporated by reference in their entirety). Polyclonal antibody to hCG-β also detected the same chimeric protein by western blot, as shown in FIG. 3B. As expected, exactly the same size bands were also shown when compared to the bands in FIG. 3A, whereas these bands were absent in mock-transfected cells, indicating that the chimera protein was expressed in Sf9 cells and detected by antibodies against LH-R as well as hCG. In FIGS. 3A-B, the 110 kDa protein would represent the mature chimera with post-translation modification, and the other band with molecular weight greater than 172 kDa could be the aggregate of 110 kDa.

Example 3

Functional Activity Assay for Ligand Binding Using Biotinylated-hCG

A competitive binding assay was performed to determine whether the chimeric protein containing both full-length hLH-R and full-length hCG-β domains (SEQ ID NO:11) would bind to its ligand hCG. Highly purified 2.5 mg/ml hCG (CR-125, containing 11,500-12,000 IU/mg; NICHD, National Institutes of Health, Bethesda, Md.) was biotinylated by incubating 10 mg/ml of animohexanoyl-biotin-N-hydroxysuccinimide ester (AH-BNHS) for 1 hr in 0.1 M bicarbonate buffer (pH 8.4) at room temperature (Paukku et al., "Persistence of Biological Activity of Biotinylated Human Chorionic Gonadotropin and its Use for Visualization of Rat Luteinizing Hormone Receptors in Tissue Sections," *J Histochem Cytochem* 46(9):993-998 (1998), which is hereby incorporated by reference in its entirety). The ratio of AH-BNHS to hCG was adjusted to, 1:10 (w/w). The biotinylated-hCG was purified and identified by using anti-hCG and HRP-streptavidin conjugate according to the manufacturer's instructions (Zymed Labs, Inc., So. San Francisco, Calif.). After 24 hrs of transfection with recombinant baculovirus harboring the chimeric hLH-R/hCG-β gene (SEQ ID NO: 12), Sf9 insect cells were incubated with 20 ng/μl of biotinylated-hCG, with increasing concentrations of unlabeled hCG as the competitor, for 24 hrs at 27° C. The Sf9 cells infected with the recombinant baculovirus containing LH-R alone was set up as the control. After incubation the medium was aspirated and the cell pellets were washed with PBS buffer containing 0.5 g/L BSA. Cells were then incubated for 24 hrs at 27° C. with 0.8 μg/ml of biotinylated-hCG per well with or without an excess of unlabeled hCG in a total volume of 2.5 ml of PBS buffer containing 0.5 g/L BSA. Cell surface binding of hCG was determined as the biotin activity. For the determinations of the displacement of bound hCG, incubation conditions were identical except that increasing concentrations of purified hCG were used as the competitor. Specific binding of biotinylated-hCG was determined in triplicate for each independent transfection.

Figure 4A:
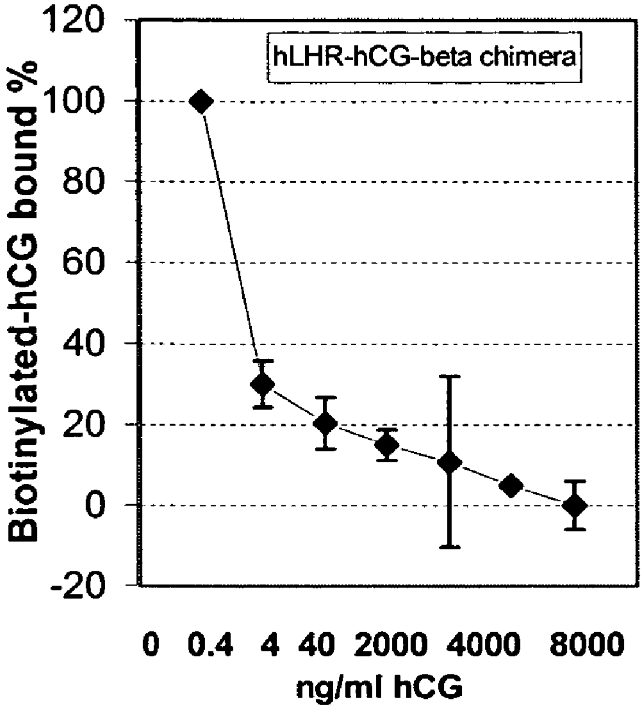
FIGS. 4A-B are graphs showing results of competitive binding assays determining the ability of the hLH-R-hCG-β fusion protein to bind to hCG ligand.
Figure 4B:
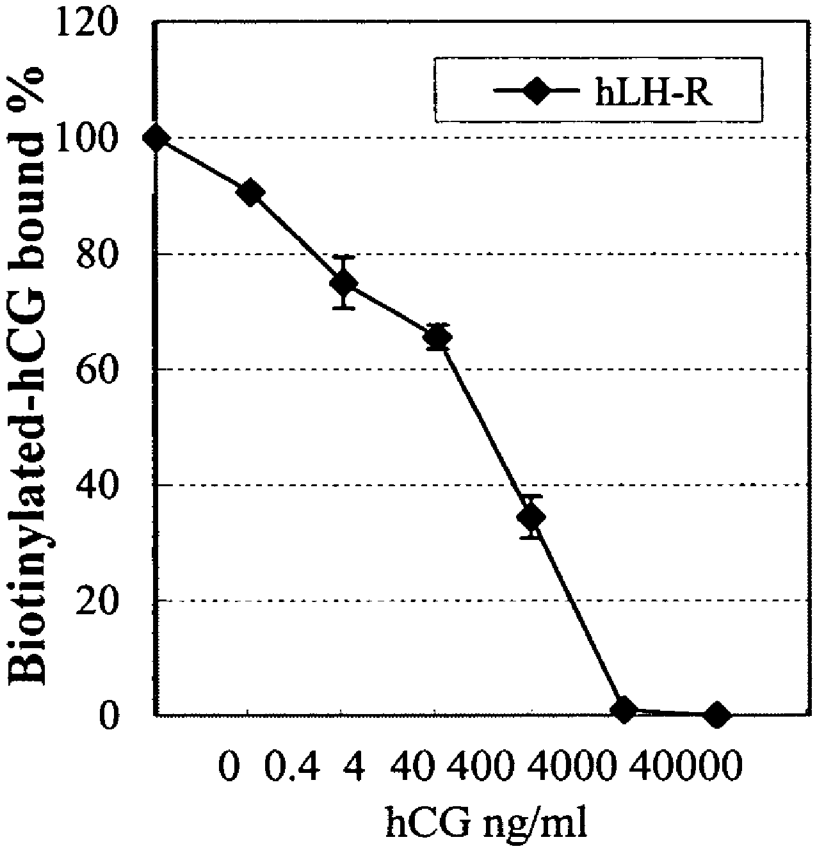

The biotinylated-hCG binding on the surface of Sf9 insect cells was examined by ELISA using horseradish peroxidase (HRP)-streptavidin conjugate (Zymed Labs, Inc., So. San Francisco, Calif.). As shown in FIG. 4A, biotinylated-hCG binding to the Sf9 cells was displaced with increasing amounts of unlabeled hCG, indicating that hCG bound specifically to the hLH-R-hCG-β chimeric fusion protein and biotinylated-hCG preserved its ability to bind specifically to LH-R. As shown in FIG. 4B, the control with hLH-R alone also specifically bound to biotinylated-hCG as demonstrated by the displacement of binding in the presence of increasing concentration of unlabeled hCG.

Example 4

Intracellular cAMP Stimulation by hLH-R-hCG-β Recombinant Fusion Protein

The chimeric hLH-R.hCG-β-CTP protein was further examined for its ability to stimulate the cAMP production in the transfected Sf9 cells as well as in the incubation medium in the absence and presence of increasing quantities of hCG. The Sf9 cells were plated in a 12-well plate and washed twice by serum-free medium containing 0.8 mM isobutylmethylxanthine and 0.1% BSA. Sixteen to 18 hrs after transfection with the chimeric hLH-R/hCG-β nucleic acid molecule (SEQ ID NO:12), the cells were incubated in the same medium for 15 min at 27° C. Increasing concentrations of hCG were added, and incubation was continued for 4 hrs at 27° C. The incubation medium and cell pellets were collected by centrifugation. Cells were lysed in 0.1N HCl. The supernatants and the incubation medium were collected for cAMP assay using cAMP kit according to the manufacturer's instructions (BioMol Research Inc., Plymouth Meeting, Pa.).

Figure 5A:
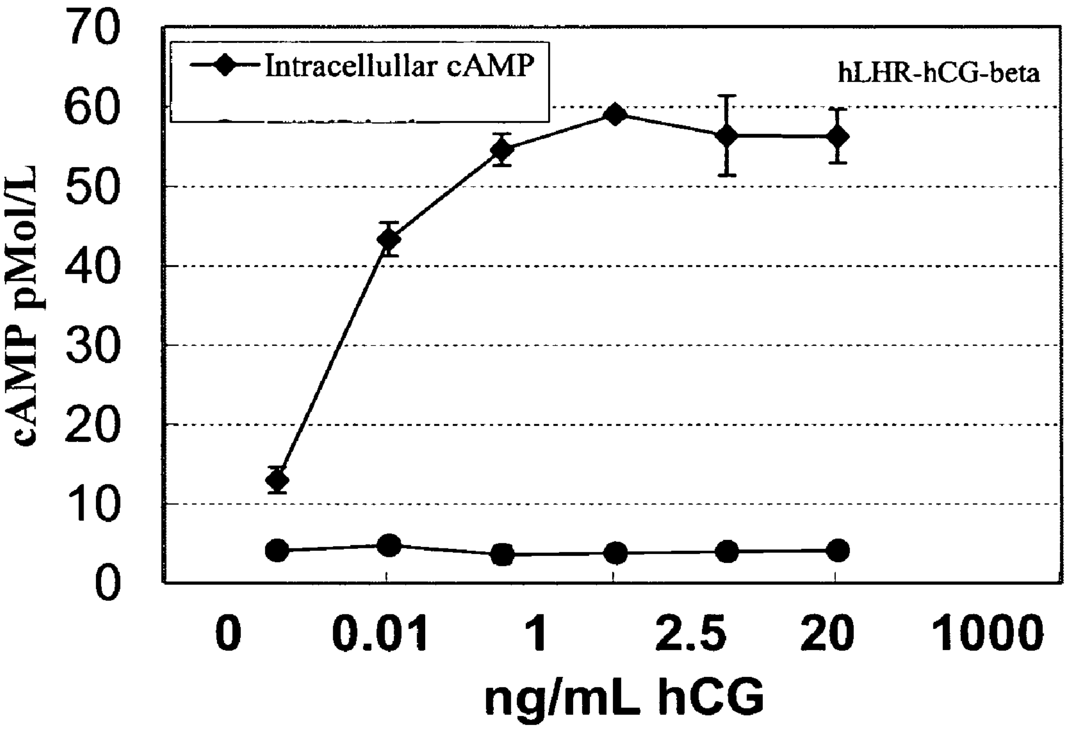
FIGS. 5A-B are graphs showing intracellular cyclic AMP stimulation expressed in $2\times10^6$ Sf9 insect cells as compared with cAMP in the culture medium.
Figure 5B:
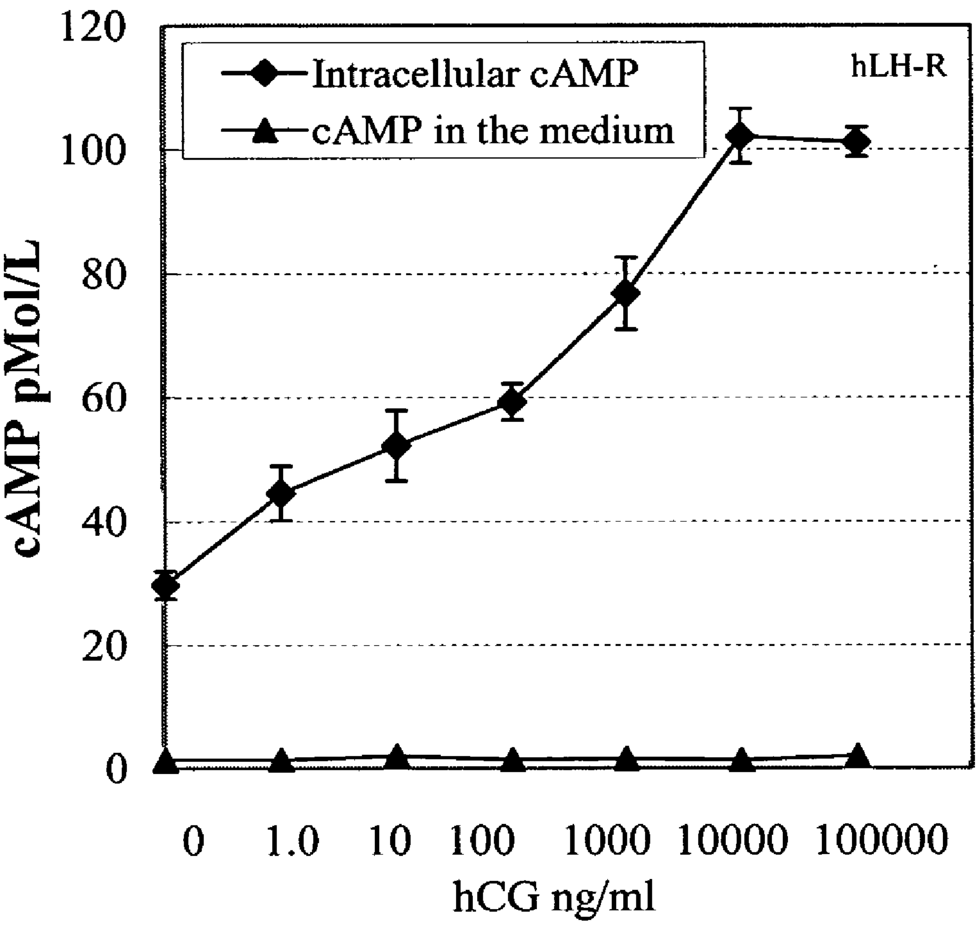

FIG. 5A shows the ability of the chimeric protein hLH-R-hCG-β to stimulate the cAMP produced in the transfected Sf9 cells as well as in the incubation medium in the absence and presence of increasing quantities of hCG. In addition, the Sf9 cells infected with the recombinant baculovirus containing LH-R alone was set up as a control, shown in FIG. 5B. The Sf9 cells expressing chimeric hLH-R-hCG-β exhibited an increase in cAMP levels in a dose-dependent pattern and reached up to 59.1 pmol/L, which was approximately a 6-fold increase over the baseline level in the absence of hCG. In the absence of hCG, the intracellular cAMP level was also compared in the transfected and mock-transfected Sf9 cells to determine whether hCG-β at the C-terminal end of the chimeric protein would have bound to the N-terminus of the hLH-R in the chimeric protein. The cAMP concentration in transfected Sf9 cells was 13.2±1.61 pmol/L, compared to 10.09±2.38 pmol/L in mock-transfected cells, indicating no significant difference ($p>0.05$), and suggesting that the production of cAMP was not stimulated by hCG-β component of the chimeric protein. The level of cAMP in mock-transfected cells also did not change in the presence of increasing quantities of hCG. Furthermore, the cAMP in the incubation medium from infected cells showed no difference compared to mock-infected cells. Compared to the hLH-R, the chimera showed significant increase in intracellular cAMP when the concentration of hCG was only 0.01 ng/ml.

Example 5

Determination of hCG-β in Recombinant Protein by hLH-R/hCG-β Chimeric Nucleic Acid Molecule Expression of hCG-β protein by the chimera 1 gene was determined in the solubilized membrane fractions of transfected Sf9 cells. Approximately $2.5\times10^6$ cells were seeded in 60 mm dishes. The recombinant baculovirus containing chimeric nucleic acid molecule was added with a multiplicity of infection (MOI) of 5.0 and incubated at 27° C. After 72 hrs, cell pellets were collected by centrifugation. Solubilized membrane proteins were analyzed for total protein by using DC Protein Assay kit (Bio-Rad, Hercules, Calif.). hCG-β was determined in the soluble membrane fraction by using the ADVIA Centaur Total hCG and hCG-β assay by Automated Chemiluminescence System (ACS) 180-SE. As shown in Table 1, below, all the samples contained a similar amount of protein, including the mock-transfected cells. hCG was not detectable in the mock-transfected Sf9 cells (see Table 1), whereas in the infected Sf9 cells, the concentration of the expressed hCG-β was 267.76±7.6 IU hCG/L. These results attest to the expression of a bifunctional protein containing both hLH-R and hCG-β activities by the hLH-R-hCG-β chimera.

TABLE 1

Total protein and hCG concentration in solubilized membrane fractions of Sf9 insect cells transfected with hLH-R-hCG-β chimeric construct.

| Solubilized Membrane protein | Total protein mg/ml | Total hCG & hCG-β* IU/L |
|---|---|---|
| Normal Sf9 cells | 5.16 ± 0.82 | ND |
| Infected Sf9 cells | 6.10 ± 3.87 | 267.76 ± 7.6 (3) |

In the present invention, a unique chimeric nucleic acid construct of full-length hLH-R and full-length hCG-β (chimera 1) was designed and synthesized. This construct was expressed in Sf9 insect cells to produce a bifunctional protein displaying both LH-R and hCG-β activities, and functional properties such as ligand binding ability and intracellular cAMP stimulation. Western blot analyses of membrane solubilized fractions revealed that the protein expressed in Sf9 cells was detected by the antibody to LH-R as well as the antibody to hCG-β, indicating that the recombinant protein contained antigenic sites of both LH-R and hCG-β.

The recombinant chimeric hLH-R-hCG-β protein recognized its ligand, as shown by the specific binding of hCG to the chimeric protein. This also suggests that the hCG-β component of the chimeric protein did not interfere with the binding of exogenous hCG to LH-R. The hCG-β alone does not bind to the LH-R. In the yoked fusion protein expressed in COS-7 cells as described by Wu et al (Wu et al., "Protein Engineering of Novel Constitutively Active Hormone-Receptor Complex," *J Biol Chem* 271:31638-31642 (1996), which is hereby incorporated by reference in its entirety), the α and β subunits of hCG were attached to the N-terminal ligand binding domain of the receptor, and exogenous hCG probably could not bind to the yoked LH-R.

The stimulation of intracellular cAMP by hCG was examined in order to investigate whether the binding of hCG to the chimera resulted in biological function. As shown in FIG. 5A, the intracellular cAMP concentration increased, with increasing concentrations of hCG in a dose-response manner, while cAMP levels in culture medium did not change regardless of the concentration of hCG, which indicated that cAMP was produced inside Sf9 cells. To further confirm the stimulation of cAMP only by exogenous hCG, and not by the intramolecular hCG-β, the cAMP production in both mock-transfected as well as transfected Sf9 cells was determined in the absence of exogenous hCG. Levels of intracellular cAMP in both mock as well as transfected Sf9 cells did not show any significant difference, further indicating that the intracellular hCG-β of the chimeric protein did not have any effect on the stimulation of cAMP indicating that intracellular hCG-β did not bind to the hLH-R component of the chimeric protein. It is well known that hCG-β alone does not bind to the receptor.

Example 6

Synthesis of Chimeric hLH-R Extracellular Domain/hCG-β Carboxy Terminal Peptide Nucleic Acid Construct Restriction enzymes were purchased from New England BioLabs, Inc. (Beverly, Mass.). Oligonucleotides used for PCR amplification and sequencing were synthesized by Invitrogen (Carlsbad, Calif.). FBS was purchased from Gibco (Invitrogen, Carlsbad, Calif.). DNA Polymerase, T4 Ligase, *E. Coli* strain DH5α competent cells, pBlueBac4.5/V5-His, linearized Bac-N-Blue™ viral DNA, Cellfectin, gentamycin, and Grace's insect cell medium were purchased from Invitrogen (Invitrogen, Carlsbad, Calif.). Aminohexanoyl-biotin-N-hydroxysuccinimide ester (AH-BNHS) was obtained from Zymed Labs Inc. (So. San Francisco, Calif.). Polyvinylidene difluoride (PVDF) membrane, chemiluminescence kit, PBS Buffer and TBS buffer were obtained from Bio-Rad (Hercules, Calif.). hCG (CR-125, containing 11,500-12,000 IU/mg) was provided by NICHD, National Institutes of Health (Bethesda, Md.). Isobutylmethylxanthine was obtained from Calbiochem (San Diego, Calif.). cAMP kits were purchased from BioMol Research Inc. (Plymouth Meeting, Pa.). Antibody to LH receptor and antibody to hCG-β were raised in rabbits (Pal et al., "Biological Actions of Monoclonal Antibodies to Bovine Lutropin Receptor," *J Reprod Immunol* 22(1):103 (1992), which is hereby incorporated by reference in its entirety).

Figure 6:
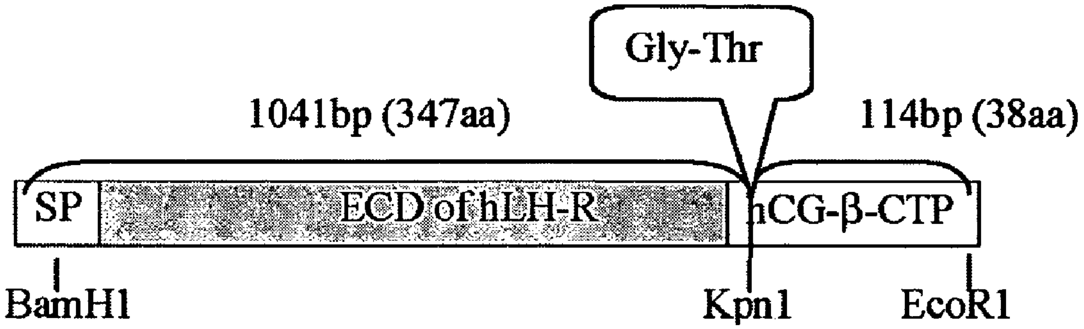
FIG. 6 is a schematic diagram of chimeric gene hLH-R-ECD-hCG-β-CTP. The extracellular domain (ECD) of hLH-R with the signal peptide (SP) at its N-terminus was fused to the N-terminus of hCG-β-CTP using Gly-Thr as the linker dipeptide.
Figure 7:
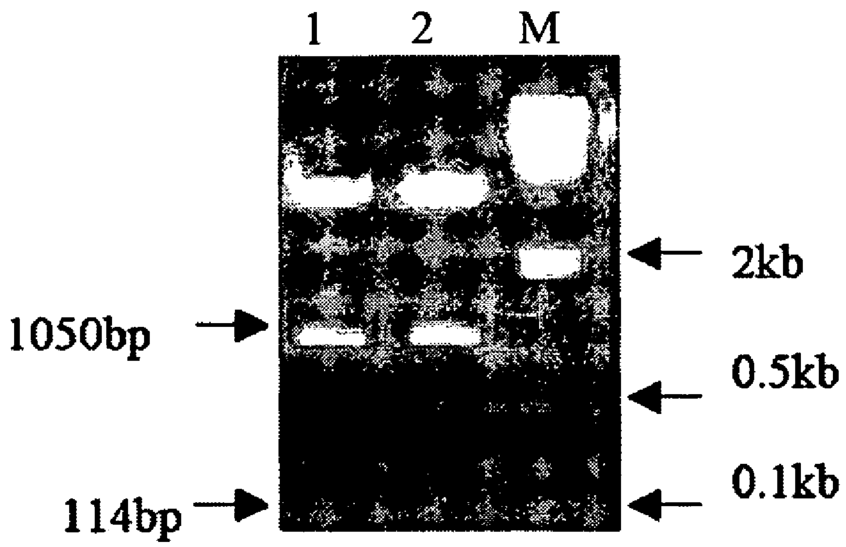
FIG. 7 shows the agarose gel electrophoresis of a chimeric DNA construct containing the extracellular domain of hLH-R and the hCG-β-CTP domain (hLH-R-ECD-hCG-β construct) after enzyme digestion of vector pBlueBac4.5 containing the hLH-R-ECD-hCG-β construct. Lane 1: recombinant DNA digested with BamH I and Kpn I. Lane 2: recombinant DNA digested with BamH I, Kpn I and EcoR I. M: DNA size markers.

The cDNA encoding the hLH-R-ECD containing 1041 bp (SEQ ID NO:6) with signal peptide of 20 amino acids in the vector pBluescript-hLH-R (Minegishi et al., "Cloning and Sequencing of Human LH/hCG Receptor cDNA," *Biochem Biophys Res Commun* 201:1057 (1994), which is hereby incorporated by reference in its entirety) was amplified by PCR. The PCR product was cloned into the transfer vector pBlueBac4.5/V5-His using BamH I and Kpn I restriction sites, which were inserted by PCR at 5' primer and 3' primer, respectively. The cDNA of hCG-β-CTP containing 114 bp (SEQ ID NO:8) was also amplified by PCR (Lobel et al., "Expression and Characterization of Recombinant Beta-Subunit hCG Homodimer," Endocrin 10(3):261-270 (1999), which is hereby incorporated by reference in its entirety), and fused to hLH-R-ECD by subcloning into expression vector pBlueBac4.5/V5-His containing ECD of hLH-R with Kpn I and EcoR I. Two amino acids (Gly and Thr) were inserted between the C-terminus of the hLH-R-ECD and the N-terminus of the hCG-β-CTP to form a contiguous BamH I-hLH-R-ECD-Kpn I-hCG-β-CTP-EcoRI fusion. The chimeric gene thus consisted of a total of 1161 bp (SEQ ID NO:16). This construct is shown schematically in FIG. 6. Ligation reactants were transformed into competent DH5α cells. The recombinant clones were identified by restriction enzyme digestions of the DNA as well as by DNA sequencing, to ensure that no mutations were introduced during the amplification process. The positive clones were identified by restriction enzyme digestion of DNA followed by agarose gel electrophoresis, which showed three bands of molecular size 5 kb, 1 kb, and 0.1 kb corresponding to the vector pBlueBac4.5/V5-His, hLH-R-ECD and hCG-β-CTP, respectively, as shown in FIG. 7. The DNA sequence of the construct showed that no mutation occurred during the PCR amplification. These results confirmed the DNA integrity hLH-R-ECD-hCG-β-CTP chimera.

Example 7

Expression of hLH-R-ECD-hCG-β-CTP Nucleic Acid Molecule in Baculovirus System and Detection of Fusion Protein by Western Blots The chimeric gene containing both the extracellular domain of hLH-R and CTP of hCG-β formed a single polypeptide chain consisting of 387 amino acids (SEQ ID NO:15) with two amino acids, Gly and Thr, as a linker between the C-terminus of the hLH-R-ECD and the N-terminus of hCG-β-CTP. Individual recombinant pBlueBac4.5 transfer vectors containing both the chimeric DNA and hLH-R-ECD alone were co-transfected with linearized Bac N-Blue™ viral DNA into Sf9 insect cells in the presence of Cellfectin. S19 insect cells were grown in monolayers at 27° C. in Complete Grace's medium, supplemented with 10% fetal calf serum and 10 μg/ml gentamycin. The recombinant baculovirus was purified by the plaque assay. Blue putative recombinant plaques were transferred to 12-well microtiter plates and amplified in Sf9 cells to make high titer viral solution. Approximately $2.5\times10^6$ Sf9 cells were seeded in 60 mm dishes, and the virus was added with a multiplicity of infection (MOI) of 5.0 and incubated at 27° C. for 72 hr. Cell pellets and culture medium were collected after 72 hr and separated by centrifugation. Solubilized fractions were analyzed in a 7.5% SDS-PAGE. Samples were resolved in the 7.5% polyacrylamide gels under reducing conditions, and the gel was stained with Coomassie Brilliant Blue R 250.

For western blot analysis, cell pellets were washed twice in PBS buffer to remove the serum proteins. The cells were then solubilized by boiling in the lysis buffer ($1\times10^6$ cells per 100 μl) as previously described (Hao et al., "Expression of A Recombinant Bifunctional Protein from a Chimera of Human Lutropin Receptor and Human Chorionic Gonadotropin β-Subunit," *Journal of Reproductive Immunology* 63:123-135 (2004), which is hereby incorporated by reference in its entirety). The supernatant was then boiled for 5 min. in electrophoresis sample buffer containing 62.5 mM Tris-HCl, pH 6.8, 25% glycerol, 2% SDS and 5% β-1 mercaptoethanol. The solubilized proteins were analyzed by gel-electrophoresis in a 7.5% SDS-polyacrylamide under reducing conditions. Proteins were then transferred electrophoretically from the gel to the polyvinylidene difluoride (PVDF) membrane after blocking with 5% milk proteins dissolved in TBS buffer. The membranes were probed for the presence of both hLH-R and hCG-β by incubating separately with antibody to LH-R and with antibody to hCG-β (Pal et al., "Biological Actions of Monoclonal Antibodies to Bovine Lutropin Receptor," *J Reprod Immunol* 22(1):87-103 (1992), which is hereby incorporated by reference in its entirety). The antibody-bound protein bands in the membrane were detected using chemiluminescence via a secondary horseradish peroxidase-labeled anti-rabbit/anti-mouse antibody according to the manufacturer's instructions. Protein bands on the membrane were visualized by exposure to X-ray film.

Figure 8:
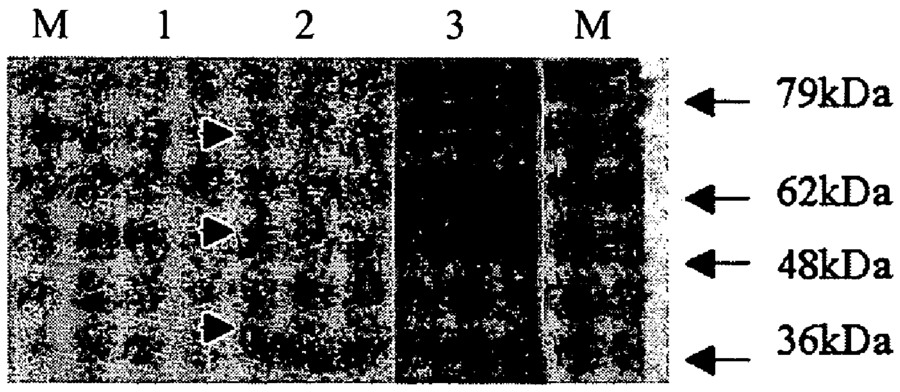
FIG. 8 shows the agarose electrophoresis separation of approximately 60 μg of solubilized membrane proteins of Sf9 cells on 7.5% SDS-PAGE under reducing conditions. Lane 1: solubilized proteins from mock-transfected Sf9 cells. Lane 2: solubilized proteins from transfected Sf9 cells with hLH-R-

As shown in FIG. 8, the SDS-PAGE showed three bands of molecular weights of about 36 kDa, 50 kDa and 75 kDa. As shown in FIG. 9A, three bands with molecular weights of about 36 kDa, 50 kDa and 75 kDa were detected using antibody to LH-R. Antibody to hCG-β also detected the same molecular weight chimeric proteins by western blots, shown in FIG. 9B, similar to the bands in FIG. 9A, whereas these bands were absent in mock-transfected cells, indicating that the chimeric protein was expressed in Sf9 cells and was detected by antibody against LH-R as well as by the antibody against hCG-β. The 50 kDa protein would probably represent the mature chimera with post translation modification. The protein bands of molecular weight of approximately, 35 kDa and 75 kDa probably represent the oligomeric forms of the chimera. The culture medium showed no protein bands in western blots, indicating that the recombinant proteins were not secreted.

Example 8

Functional Activity Assay for Ligand Binding Using Biotinylated hCG

Highly purified, 2.5 mg/ml, hCG (CR-125, containing 11,500-12,000 IU/mg was incubated with 10 mg/ml of aminohexanoyl-biotin-N-hydroxysuccinimide ester (AH BNHS) for 1 hr in 0.1 M bicarbonate buffer (pH 8.4) at room temperature (Paukku et al., "Persistence of Biological Activity of Biotinylated Human Chorionic Gonadotropin and its Use for Visualization of Rat Luteinizing Hormone Receptors in Tissue Sections," *J Histochem Cytochem* 46(9):993-998 (1998), which is hereby incorporated by reference in its entirety). The ratio of AH-BNHS to hCG was adjusted to 1:10 (w/w). The biotinylated-hCG was purified and identified by using anti-hCG and HRP-streptavidin conjugate according to the manufacturer's instructions.

Twenty four hours after transfection in 12-well plates, competitive ligand binding assays were carried out on intact transfected Sf9 cells expressing chimera, as well as hLH-R-ECD alone as the control. The Sf9 cells were rinsed with PBS buffer containing 0.5 g/L BSA. The cells were then incubated for 24 hr at 27° C. with 0.8 μg/ml of biotinylated-hCG per well with or without an excess of unlabeled hCG, in a total volume of 2.5 ml of PBS buffer containing 0.5 g/L BSA. The cell surface binding of hCG was determined as the biotin activity according to the manufacturer's instructions. For the determinations of the displacement of bound hCG, incubation conditions were identical except that increasing concentrations of purified hCG were used as the competitor. Binding of biotinylated-hCG was determined in triplicate for each independent transfection.

Example 9

Determination of Ligand-Induced Intracellular cAMP Production by hLH-R-ECD/hCG-β-CTP Recombinant Fusion Protein The chimeric protein hLH-R-ECD-hCG-β-CTP was further examined for its ability to stimulate the cAMP production in the transfected Sf9 cells as well as in the incubation medium in the absence and presence of increasing quantities of hCG. The Sf9 cells were seeded in a 12-well plate. Sixteen to 18 hr after transfection with the hLH-R-ECD-hCG-β-CTP chimeric construct, the cells were washed twice by serum-free medium containing 0.8 mM isobutylmethylxanthine and 0.1% BSA and incubated in the same medium for 15 min at 27° C. Increasing concentrations of hCG were added, and incubation was continued for 4 hr. at 27° C. The incubation medium and cell pellets were collected by centrifugation. The production of cAMP was also measured at different time intervals. Cells were lysed in 0.1 N HCl. The lysis supernatants and the incubation medium were collected for cAMP assay using cAMP kit according to the manufacturer's instructions.

The Sf9 cells expressing chimeric hLH-R-ECD-hCG-β-CTP exhibited an increase in cAMP levels in a dose-dependent pattern, as shown in FIG. 11A, while hLH-R-ECD did not stimulate the production of intracellular cAMP, as shown in FIG. 11B. In the absence of hCG, the intracellular cAMP level was also compared in the transfected and mock-transfected Sf9 cells to determine whether hCG-β-CTP at the C-terminal end of the chimeric protein would have interacted with the N-terminus of HLH-R-ECD in the chimeric protein. The results showed little difference between transfected and mock-transfected cells in the absence of hCG. cAMP level in mock-transfected cells also did not change in the presence of increasing quantities of hCG. Furthermore, the cAMP in the incubation medium from infected cells showed no difference compared with mock-infected cells. As shown in FIG. 11C, the production of cAMP in Sf9 cells transfected with chimeric DNA construct showed maximum stimulation at one hour of incubation with hCG, which was similar to the pattern of LH-R when incubated with hCG (Igarashi et al., "Functional Expression or Recombinant Human Luteinizing Hormone/Human Choriogonadotropin Receptor," *Biochem Biophys Res Commun* 201:248-256 (1994), which is hereby incorporated by reference in its entirety). There was no stimulation of cAMP production in Sf9 cells transfected with hLH-R-ECD alone.

Example 10

Measurement of hCG-β CTP in Recombinant Protein

Approximately 2.5×10$^6$ cells were seeded in 60 mm dishes. The recombinant baculovirus containing chimeric hLH-R-ECD-hCG-β-CTP nucleic acid molecule was added with a multiplicity of infection (MOI) of 5.0 and incubated at 27° C. After 72 hr, cell pellets were collected by centrifugation. Solubilized proteins were analyzed for total protein by using DC Protein Assay kit. hCG β-CTP was determined in the soluble membrane fraction by using the ADVIA Centaur. Total hCG and hCG-β assay using two a site specific antibody by Automated Chemiluminescence System (ACS) 180-SE.

Example 11

Affinity of hCG Binding to Chimeric hLH-R-ECD-hCG-β-CTP

A competitive binding assay was performed to determine whether hCG would bind to the chimeric protein containing both hLH-R-ECD and hCG-β-CTP. After 24 hr of transfection with recombinant baculovirus, Sf9 insect cells were incubated for 24 hr at 27° C. with 20 ng/μl of biotinylated-hCG and increasing concentrations of unlabeled hCG as the competitor. The Sf9 cells infected with the recombinant baculovirus containing ECD of LH-R alone was set up as the control. The binding of biotinylated-hCG on the surface of the Sf9 insect cells was examined by ELISA using horseradish peroxidase (HRP)-streptavidin conjugate. Unlabeled hCG inhibited the binding of biotinylated-hCG to the chimeric protein, as shown in FIG. 10, but not to the hLH-R-ECD. This suggests that the expressed hLH-R-ECD was trapped inside the cells while chimeric protein was located on the membrane. The results indicated that hCG bound specifically to the hLH-R-ECD-hCG-β-CTP chimeric protein and that the biotinylated-hCG preserved its ability to bind specifically to LH-R.

Example 12

Expression of Chimeric hLH-R Extracellular Domain/hCG-β Carboxy Terminal Peptide Nucleic Acid Construct Expression of hCG-β-CTP protein by the chimeric hLH-R-ECD-hCG-β-CTP nucleic acid molecule was further examined for its ability to stimulate the cAMP production in the solubilized fractions of transfected Sf9 cells, as well as in the incubation medium in the absence and presence of increasing quantities of hCG. As shown in Table 2, below, the chimera protein hLH-R-ECD-hCG-β-CTP contained 355±2.5 mIU hCG/ml, but hCG was not detectable in Sf9 cells transfected with hLH-R-ECD alone as well as in the mock-transfected solubilized Sf9 cells. These results further attested that the hCG-β-CTP, with only 38 amino acid chain, still had the antigenic site, which was recognized by antibodies to hCG, and confirmed the expression of a bifunctional protein containing both hLH-R and hCG-β activities by the hLH-R-ECD-hCG-β-CTP chimera.

TABLE 2

Total protein and hCG concentration in solubilized fractions of Sf9* insect cells transfected with DNA constructs.

| Solubilized Proteins | Total protein mg/ml | Total hCG & hCG-β** mIU/mL | hCG/protein mIU/mg |
|---|---|---|---|
| Mock-transfected Sf9 cells | 5.16 ± 0.82 | ND | N/A |
| hLH-R-ECD | 8.1 ± 0.09 | ND | N/A |
| hLH-R-ECD-hCG-β-CTP | 13.9 ± 0.303 | 355 ± 2.5 | 25.5 |

*Sf9 cells transfected with recombinant baculovirus were collected after 72 hr. of transfection with two DNA chimera constructs. Solubilized proteins were analyzed for total protein and total hCG and hCG-β concentration.

An interspecies usefulness of the present invention is readily visualized because of the structural homology, functional similarity, and immunological cross-reactivity of LH-R of other vertebrates with human LH-R (Ascoli et al., The Lutropin/Choriogonadotropin Receptor, A 2002 Perspective," *Endocr Rev* 23(2):141-174 (2002); Pal et al., "Active Immunization of Baboons (*Papio anubis*) with the Bovine LH Receptor," *J Reprod Immunol* 21(2):163-174 (1992); Pal et al., "Biological Actions of Monoclonal Antibodies to Bovine Lutropin Receptor," *J Reprod Immunol* 22(1):103 (1992); Remy et al., "Immunization Against Exon 1 Decapeptides From the Lutropin/Choriogonadotropin Receptor or the Follitropin Receptor as Potential Male Contraceptive," *J Reprod Immunol* 32(1):37-54 (1996); Singh et al., "Effect of Immunization with Lutropin-Receptor on the Ovarian Function of Rabbits," *J Immunoassay* 16(1):1-16 (1995), which are hereby incorporated by reference in their entirety). Female dogs and cats, actively immunized with highly purified bovine LH-R, produced antibodies to the LH-receptor and suppressed progesterone synthesis, apparently due to the blockade of the gonadal receptor (Saxena et al., "Modulation of Ovarian Function in Female Dogs Immunized With Bovine Luteinizing Hormone Receptor," *Reprod Domest Anim* 37(1): 9-17 (2002) and Saxena et al., "Effect of Immunization with Bovine Luteinizing Hormone Receptor on Ovarian Function in Cats," *Am J Vet Res* 64(3):292-298 (2003), which are hereby incorporated by reference in their entirety). Endogenous antibodies against hCG-β alone have been shown to inhibit conception (Gupta et al., "Contraceptive Vaccines," *Adv Contracept Deliv Syst* 10(3-4):255-65 (1994); Heikoop et al., "Evaluation of Subunit Trunction and the Nature of the Spacer for Single Chain Human Gonadotropins," *Eur J Biochem* 245:656-662 (1997) and Stevens, V. C., "Use of Synthetic Peptides as Immunogens for Developing a Vaccine Against Human Chorionic Gonadotropin," *Ciba Found Symp* 119:200-25 (1986), which are hereby incorporated by reference in their entirety). Moreover, studies in dogs, cats, and baboon (Saxena et al., "Modulation of Ovarian Function in Female Dogs Immunized With Bovine Luteinizing Hormone Receptor," *Reprod Domest Anim* 37(1):9-17 (2002); Saxena et al., "Effect of Immunization with Bovine Luteinizing Hormone Receptor on Ovarian Function in Cats," *Am J Vet Res* 64(3):292-298 (2003); and Pal et al., "Active Immunization of Baboons (Papio anubis) with the Bovine LH Receptor," *J Reprod Immunol* 21(2):163-174 (1992); Pal et al., "Biological Actions of Monoclonal Antibodies to Bovine Lutropin Receptor," *J Reprod Immunol* 22(1):103 (1992), which are hereby incorporated by reference in their entirety) indicate that the infertile ovarian and behavioral profiles during immunization against LH-R alone were reversible, however, it remains to be seen if the effect of immunization against the LHR-hCG-β chimera would also be reversible. Hence, the antibodies to a bifunctional protein containing LH-R and hCG-β moieties, as described here, would be expected to block the binding of LH to the receptor. The antibodies to the hCG-β would specifically neutralize chorionic gonadotropin (CG)-like material produced by the blastocyst at the time of implantation and inhibit conception (Saxena, B. B., "Measurement and Clinical Significance of Preimplantation Blastocyst Gonadotropins," *J Reprod Fertil Suppl* 37:115-119 (1989), which is hereby incorporated by reference in its entirety).

Even though LH-R alone is antigenic at the interspecies level, a chimeric construct of LH-R and hCG-β could presumably become more antigenic since it will present to the immune system as a heterologous antigen and facilitate antibody response (Vaitukaitis et al., "A Radioimmunoassay Which Specifically Measures Human Chorionic Gonadotropin in the Presence of Human Luteinizing Hormone," *Am J Obstet Gynecol* 113(6):751-758 (1972); Ross, G. T., "Clinical Relevance of Research on the Structure of Human Chorionic Gonadotropin," *Am J Obstet Gynecol* 129(7):795-808 (1977); Vaitukaitis et al., "Gonadotropins and Their Subunits: Basic and Clinical Studies," *Recent Prog Horm Res* 32:289-331 (1976); and Vaitukaitis, J. L., "Radioimmunoassay of Human Choriogonadotropin," *Clin Chem* 31(10):1749-1754 (1985), which are hereby incorporated by reference in their entirety). Thus, the recombinant bifunctional LH-R and hCG-β protein provide a potentially new antigen to be used for the immuno-regulation of the gonadal function as postulated earlier (Saxena et al., "New Approaches in Fertility Regulation," *J Obstet Gynaecol* 4(Suppl 1):S 16-22 (1984), which is hereby incorporated by reference in its entirety). The effects of antibodies to the hLH-R-hCG-β chimera on non-gonadal hCG and LH-R function remains to be elucidated. Antibodies to hLH-R or chimeras with hCG-β may also assist in further understanding the mechanism of ligand receptor interaction at the molecular levels (Fralish et al., "Structural Analysis of Yoked Chorionic Gonadotropin-Luteinizing Hormone Receptor Ectodomain Complexes by Circular Dichroic Spectroscopy," *Mol Endocrinol* 17(7):1192-1202 (2003), which is hereby incorporated by reference in its entirety).

The present invention discloses the synthesis of a chimeric DNA construct of full-length of hLH-receptor and hCG-β and its expression in Sf9 cells to produce a bifunctional protein. Recombinant protein was recognized by antibodies to LHR as well as anti-hCG-β in western blots, thus indicating the preservation of immunological epitopes for both hLH-R and hCG-β in the chimera. Specific ligand binding of recombinant hLH-R component was demonstrated by the displacement of bound labeled hCG at increasing concentrations of unlabeled hCG, indicating that the presence of hCG-β component of the chimera did not interfere with the binding of hCG to LH-R. hCG-β was also present in the recombinant chimeric protein as shown by a specific hCG-β chemiluminescence assay. Treatment of transfected Sf9 cells with hCG induced dose-dependent increase in the stimulation of intracellular cAMP production, which showed that the ligand binding had functional activity. These results demonstrate that the chimeric DNA construct of hLH-R-hCG-β expressed a bifunctional protein containing both hLH-R and hCG-β activities, which could provide a unique potential antigen for immunocontraception in vertebrates.

The present invention also describe the synthesis of a DNA construct of hLH-R-ECD fused with hCG-β-CTP, and the expression of a chimeric bifunctional protein, which would produce bifunctional antibodies with dual effects. Antibodies directed to the ECD of LH-R would specifically block the high affinity binding of the ligand to the receptor; whereas the antibodies to hCG-β-CTP moiety would specifically neutralize hCG produced at the time of implantation (Saxena, B. B., "Measurement and Clinical Significance of Preimplantation Blastocyst Gonadotropins," *J Reprod Fertil Suppl* 37:115-119 (1989), which is hereby incorporated by reference in its entirety) and consequently suppress the production of progesterone by the corpus luteum. The bifunctional antibodies would thereby inhibit fertility. Antibodies specific to the C-terminal peptide of hCG-β would have little cross-reaction with pituitary LH. Thus, hLH-R-ECD-hCG-β-CTP chimeric protein provides a unique antigen for immuno-regulation of gonadal function among vertebrates in both female and male.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A chimeric nucleic acid molecule having the nucleotide sequence of SEQ ID NO: 12.

2. A chimeric nucleic acid molecule encoding a protein having the amino acid sequence of SEQ ID NO: 11.

3. A nucleic acid construct comprising:

the chimeric nucleic acid molecule according to claim 2, and transcriptional and translational regulatory nucleotide sequences linked to the nucleic acid molecule to allow expression of the chimeric nucleic acid molecule.

4. An isolated host cell comprising the chimeric nucleic acid molecule according to claim 2.

5. The isolated host cell according to claim 4, wherein the host cell is selected from the group consisting of a bacterial cell, a yeast cell, an insect cell, and a mammalian cell.

6. An isolated virus comprising the chimeric nucleic acid molecule according to claim 2.

7. The isolated host cell according to claim 5, wherein the host cell is an insect cell.

8. The isolated host cell according to claim 5, wherein the host cell is a mammalian cell.

9. The isolated host cell according to claim 8, wherein the mammalian cell is selected from the group consisting of a canine cell, a feline cell, and a human cell.

10. The isolated host cell according to claim 4, wherein the host cell expresses the human lutropin hormone receptor/human chorionic gonadotropin-β fusion protein encoded by the nucleic acid molecule and exhibits bifunctional activity comprising human lutropin hormone receptor activity and human chorionic gonadotropin-β activity.

11. An isolated fusion protein having the amino acid sequence of SEQ ID NO: 11.

12. A composition comprising:

the isolated fission protein according to claim 11 and a pharmaceutical carrier.

* * * * *

SEQUENCE LISTING

<160> NUMBER OF SEQ ID NOS: 18

<210> SEQ ID NO 1
<211> LENGTH: 701
<212> TYPE: PRT
<213> ORGANISM: Human

<400> SEQUENCE: 1

Met Lys Gln Arg Phe Ser Ala Leu Gln Leu Leu Lys Leu Leu Leu Leu
1 5 10 15

Leu Gln Leu Gln Pro Pro Leu Pro Arg Ala Leu Arg Glu Ala Leu Cys
20 25 30

Pro Glu Pro Cys Asn Cys Val Pro Asp Gly Ala Leu Arg Cys Pro Gly
35 40 45

Pro Thr Ala Gly Leu Thr Arg Leu Ser Leu Ala Tyr Leu Pro Val Lys
50 55 60

Val Ile Pro Ser Gln Ala Phe Arg Gly Leu Asn Glu Val Ile Lys Ile
65 70 75 80

Glu Ile Ser Gln Ile Asp Ser Leu Glu Arg Ile Glu Ala Asn Ala Phe
85 90 95

Asp Asn Leu Leu Asn Leu Ser Glu Ile Leu Ile Gln Asn Thr Lys Asn
100 105 110

Leu Arg Tyr Ile Glu Pro Gly Ala Phe Ile Asn Leu Pro Arg Leu Lys
115 120 125

Tyr Leu Ser Ile Cys Asn Thr Gly Ile Arg Lys Phe Pro Asp Val Thr
130 135 140

Lys Val Phe Ser Ser Glu Ser Asn Phe Ile Leu Glu Ile Cys Asp Asn
145 150 155 160

Leu His Ile Thr Thr Ile Pro Gly Asn Ala Phe Gln Gly Met Asn Asn
165 170 175

Glu Ser Val Thr Leu Lys Leu Tyr Gly Asn Gly Phe Glu Glu Val Gln
180 185 190

Ser His Ala Phe Asn Gly Thr Thr Leu Thr Ser Leu Glu Leu Lys Glu
195 200 205

Asn Val His Leu Glu Lys Met His Asn Gly Ala Phe Arg Gly Ala Thr
210 215 220

Gly Pro Lys Thr Leu Asp Ile Ser Ser Thr Lys Leu Gln Ala Leu Pro
225 230 235 240

Ser Tyr Gly Leu Glu Ser Ile Gln Arg Leu Ile Ala Thr Ser Ser Tyr
245 250 255

Ser Leu Lys Lys Leu Pro Ser Arg Glu Thr Phe Val Asn Leu Leu Glu
260 265 270

Ala Thr Leu Thr Tyr Pro Ser His Cys Cys Ala Phe Arg Asn Leu Pro
275 280 285

Thr Lys Glu Gln Asn Phe Ser His Ser Ile Ser Glu Asn Phe Ser Lys
290 295 300

Gln Cys Glu Ser Thr Val Arg Lys Val Ser Asn Lys Thr Leu Tyr Ser
305 310 315 320

Ser Met Leu Ala Glu Ser Glu Leu Ser Gly Trp Asp Tyr Glu Tyr Gly
325 330 335

Phe Cys Leu Pro Lys Thr Pro Arg Cys Ala Pro Glu Pro Asp Ala Phe
340 345 350

Asn Pro Cys Glu Asp Ile Met Gly Tyr Asp Phe Leu Arg Val Leu Ile

-continued

```
        355                 360                 365

Trp Leu Ile Asn Ile Leu Ala Ile Met Gly Asn Met Thr Val Leu Phe
    370                 375                 380

Val Leu Leu Thr Ser Arg Tyr Lys Leu Thr Val Pro Arg Phe Leu Met
385                 390                 395                 400

Cys Asn Leu Ser Phe Ala Asp Phe Cys Met Gly Leu Tyr Leu Leu Leu
                405                 410                 415

Ile Ala Ser Val Asp Ser Gln Thr Lys Gly Gln Tyr Tyr Asn His Ala
            420                 425                 430

Ile Asp Trp Gln Thr Gly Ser Gly Cys Ser Thr Ala Gly Phe Phe Thr
        435                 440                 445

Val Phe Ala Ser Glu Leu Ser Val Tyr Thr Leu Thr Val Ile Thr Leu
    450                 455                 460

Glu Arg Trp His Thr Ile Thr Tyr Ala Ile His Leu Asp Gln Lys Leu
465                 470                 475                 480

Arg Leu Arg His Ala Ile Leu Ile Met Leu Gly Gly Trp Leu Phe Ser
                485                 490                 495

Ser Leu Ile Ala Met Leu Pro Leu Val Gly Val Ser Asn Tyr Met Lys
            500                 505                 510

Val Ser Ile Cys Phe Pro Met Asp Val Glu Thr Thr Leu Ser Gln Val
        515                 520                 525

Tyr Ile Leu Thr Ile Leu Ile Leu Asn Val Val Ala Phe Phe Ile Ile
    530                 535                 540

Cys Ala Cys Tyr Ile Lys Ile Tyr Phe Ala Val Arg Asn Pro Glu Leu
545                 550                 555                 560

Met Ala Thr Asn Lys Asp Thr Lys Ile Ala Lys Lys Met Ala Ile Leu
                565                 570                 575

Ile Phe Thr Asp Phe Thr Cys Met Ala Pro Ile Ser Phe Phe Ala Ile
            580                 585                 590

Ser Ala Ala Phe Lys Val Pro Leu Ile Thr Val Thr Asn Ser Lys Val
        595                 600                 605

Leu Leu Val Leu Phe Tyr Pro Ile Asn Ser Cys Ala Asn Pro Phe Leu
    610                 615                 620

Tyr Ala Ile Phe Thr Lys Thr Phe Gln Arg Asp Phe Phe Leu Leu Leu
625                 630                 635                 640

Ser Lys Phe Gly Cys Cys Lys Arg Arg Ala Glu Leu Tyr Arg Arg Lys
                645                 650                 655

Asp Phe Ser Ala Tyr Thr Ser Asn Cys Lys Asn Gly Phe Thr Gly Ser
            660                 665                 670

Asn Lys Pro Ser Gln Ser Thr Leu Lys Leu Ser Thr Leu His Cys Gln
        675                 680                 685

Gly Thr Ala Leu Leu Asp Lys Thr Arg Tyr Thr Glu Cys
    690                 695                 700


<210> SEQ ID NO 2
<211> LENGTH: 2103
<212> TYPE: DNA
<213> ORGANISM: Human

<400> SEQUENCE: 2

atgaagcagc ggttctcggc gctgcagctg ctgaagctgc tgctgctgct gcagctgcag      60

ccgccgctgc cacgagcgct gcgcgaggcg ctctgccctg agccctgcaa ctgcgtgccc     120

gacggcgccc tgcgctgccc cggccccacg gccggtctca ctcgactatc acttgcctac     180
```

-continued

```
ctccctgtca aagtgatccc atctcaagct ttcagaggac ttaatgaggt cataaaaatt    240

gaaatctctc agattgattc cctggaaagg atagaagcta atgcctttga caacctcctc    300

aatttgtctg aaatactgat ccagaacacc aaaaatctga gatacattga gcccggagca    360

tttataaatc ttcccggatt aaaatacttg agcatctgta acacaggcat cagaaagttt    420

ccagatgtta cgaaggtctt ctcctctgaa tcaaatttca ttctggaaat ttgtgataac    480

ttacacataa ccaccatacc aggaaatgct tttcaaggga tgaataatga atctgtaaca    540

ctcaaactat atggaaatgg atttgaagaa gtacaaagtc atgcattcaa tgggacgaca    600

ctgacttcac tggagctaaa ggaaaacgta catctggaga agatgcacaa tggagccttc    660

cgtggggcca cagggccgaa aaccttggat atttcttcca ccaaattgca ggccctgccg    720

agctatggcc tagagtccat tcagaggcta attgccacgt catcctattc tctaaaaaaa    780

ttgccatcaa gagaaacatt tgtcaatctc ctggaggcca cgttgactta ccccagccac    840

tgctgtgctt ttagaaactt gccaacaaaa gaacagaatt tttcacattc catttctgaa    900

aacttttcca aacaatgtga aagcacagta aggaaagtga gtaacaaaac actttattct    960

tccatgcttg ctgagagtga actgagtggc tgggactatg aatatggttt ctgcttaccc   1020

aagacacccc gatgtgctcc tgaaccagat gcttttaatc cctgtgaaga cattatgggc   1080

tatgacttcc ttagggtcct gatttggctg attaatattc tagccatcat gggaaacatg   1140

actgttcttt ttgttctcct gacaagtcgt tacaaactta cagtgcctcg ttttctcatg   1200

tgcaatctct cctttgcaga cttttgcatg gggctctatc tgctgctcat agcctcagtt   1260

gattcccaaa ccaagggcca gtactataac catgccatag actggcagac agggagtggg   1320

tgcagcactg ctggcttttt cactgtattc gcaagtgaac tttctgtcta caccctcacc   1380

gtcatcactc tagaaagatg gcacaccatc acctatgcta ttcacctgga ccaaaagctg   1440

cgattaagac atgccattct gattatgctt ggaggatggc tcttttcttc tctaattgct   1500

atgttgcccc ttgtcggtgt cagcaattac atgaaggtca gtatttgctt ccccatggat   1560

gtggaaacca ctctctcaca agtctatata ttaaccatcc tgattctcaa tgtggtggcc   1620

ttcttcataa tttgtgcttg ctacattaaa atttattttg cagttcgaaa cccagaatta   1680

atggctacca ataaagatac aaagattgct aagaaaatgg caatcctcat cttcaccgat   1740

ttcacctgca tggcacctat ctcttttttt gccatctcag ctgccttcaa agtacctctt   1800

atcacagtaa ccaactctaa agttttactg gttctttttt atcccatcaa ttcttgtgcc   1860

aatccatttc tgtatgcaat attcactaag acattccaaa gagatttctt tcttttgctg   1920

agcaaatttg gctgctgtaa acgtcgggct gaactttata gaaggaaaga tttttcagct   1980

tacacctcca actgcaaaaa tggcttcact ggatcaaata agccttctca atccaccttg   2040

aagttgtcca cattgcactg tcaaggtaca gctctcctag acaagactcg ctacacagag   2100

tgt                                                                 2103
```

<210> SEQ ID NO 3
<211> LENGTH: 165
<212> TYPE: PRT
<213> ORGANISM: Human

<400> SEQUENCE: 3

```
Met Glu Met Phe Gln Gly Leu Leu Leu Leu Leu Leu Leu Ser Met Gly
  1               5                  10                  15

Gly Thr Trp Ala Ser Lys Glu Pro Leu Arg Pro Arg Cys Arg Pro Ile
             20                  25                  30
```

Asn Ala Thr Leu Ala Val Glu Lys Glu Gly Cys Pro Val Cys Ile Thr
         35                  40                  45

Val Asn Thr Thr Ile Cys Ala Gly Tyr Cys Pro Thr Met Thr Arg Val
     50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
             100                 105                 110

Cys Arg Arg Ser Thr Thr Asp Cys Gly Gly Pro Lys Asp His Pro Leu
         115                 120                 125

Thr Cys Asp Asp Pro Arg Phe Gln Asp Ser Ser Ser Ser Lys Ala Pro
     130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 4
<211> LENGTH: 495
<212> TYPE: DNA
<213> ORGANISM: Human

<400> SEQUENCE: 4
atggagatgt tccaggggct gctgctgttg ctgctgctga gcatgggcgg gacatgggca        60
tccaaggagc cgcttcggcc acggtgccgc cccatcaatg ccaccctggc tgtggagaag       120
gagggctgcc ccgtgtgcat caccgtcaac accaccatct gtgccggcta ctgccccacc       180
atgacccgcg tgctgcaggg ggtcctgccg gccctgcctc aggtggtgtg caactaccgc       240
gatgtgcgct tcgagtccat ccggctccct ggctgcccgc gcggcgtgaa ccccgtggtc       300
tcctacgccg tggctctcag ctgtcaatgt gcactctgcc gccgcagcac cactgactgc       360
gggggtccca aggaccaccc cttgacctgt gatgaccccc gcttccagga ctcctcttcc       420
tcaaaggccc ctccccccag ccttccaagt ccatcccgac tcccggggcc ctcggacacc       480
ccgatcctcc cacaa                                                        495

<210> SEQ ID NO 5
<211> LENGTH: 347
<212> TYPE: PRT
<213> ORGANISM: Human

<400> SEQUENCE: 5

Met Lys Gln Arg Phe Ser Ala Leu Gln Leu Leu Lys Leu Leu Leu Leu
 1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

-continued

```
Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro
            340                 345
```

<210> SEQ ID NO 6
<211> LENGTH: 1041
<212> TYPE: DNA
<213> ORGANISM: Human

<400> SEQUENCE: 6

```
atgaagcagc ggttctcggc gctgcagctg ctgaagctgc tgctgctgct gcagccgccg      60

ctgccacgag cgctgcgcga ggcgctctgc cctgagccct gcaactgcgt gcccgacggc     120

gccctgcgct gccccggccc cacggccggt ctcactcgac tatcacttgc ctacctccct     180

gtcaaagtga tcccatctca agctttcaga ggacttaatg aggtcataaa aattgaaatc     240

tctcagattg attccctgga aaggatagaa gctaatgcct ttgacaacct cctcaatttg     300

tctgaaatac tgatccagaa caccaaaaat ctgagataca ttgagcccgg agcatttata     360

aatcttcccg gattaaaata cttgagcatc tgtaacacag gcatcagaaa gtttccagat     420

gttacgaagg tcttctcctc tgaatcaaat ttcattctgg aaatttgtga taacttacac     480

ataaccacca taccaggaaa tgcttttcaa gggatgaata atgaatctgt aacactcaaa     540

ctatatggaa atggatttga agaagtacaa agtcatgcat tcaatgggac gacactgact     600

tcactggagc taaaggaaaa cgtacatctg gagaagatgc acaatggagc cttccgtggg     660
```

-continued

```
gccacagggc cgaaaacctt ggatatttct tccaccaaat tgcaggccct gccgagctat    720

ggcctagagt ccattcagag gctaattgcc acgtcatcct attctctaaa aaaattgcca    780

tcaagagaaa catttgtcaa tctcctggag gccacgttga cttaccccag ccactgctgt    840

gcttttagaa acttgccaac aaaagaacag aatttttcac attccatttc tgaaaacttt    900

tccaaacaat gtgaaagcac agtaaggaaa gtgagtaaca aaacacttta ttcttccatg    960

cttgctgaga gtgaactgag tggctgggac tatgaatatg gtttctgctt acccaagaca   1020

ccccgatgtg ctcctgaacc a                                              1041
```

```
<210> SEQ ID NO 7
<211> LENGTH: 38
<212> TYPE: PRT
<213> ORGANISM: Human

<400> SEQUENCE: 7

Leu Thr Cys Asp Asp Pro Arg Phe Gln Asp Ser Ser Ser Ser Lys Ala
  1               5                  10                  15

Pro Pro Pro Ser Leu Pro Ser Pro Ser Arg Leu Pro Gly Pro Ser Asp
             20                  25                  30

Thr Pro Ile Leu Pro Gln
         35
```

```
<210> SEQ ID NO 8
<211> LENGTH: 114
<212> TYPE: DNA
<213> ORGANISM: Human

<400> SEQUENCE: 8

ttgacctgtg atgacccccg cttccaggac tcctcttcct caaaggcccc tccccccagc     60

cttccaagtc catcccgact cccggggccc tcggacaccc cgatcctccc acaa          114
```

```
<210> SEQ ID NO 9
<211> LENGTH: 699
<212> TYPE: PRT
<213> ORGANISM: Human

<400> SEQUENCE: 9

Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
```

-continued

```
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445

Ala Ser Glu Leu Ser Val Tyr Thr Leu Thr Val Ile Thr Leu Glu Arg
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575
```

-continued

```
Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
    690                 695


<210> SEQ ID NO 10
<211> LENGTH: 2097
<212> TYPE: DNA
<213> ORGANISM: Human

<400> SEQUENCE: 10

atgaagcagc ggttctcggc gctgcagctg ctgaagctgc tgctgctgct gcagccgccg      60

ctgccacgag cgctgcgcga ggcgctctgc cctgagccct gcaactgcgt gcccgacggc     120

gccctgcgct gccccggccc cacggccggt ctcactcgac tatcacttgc ctacctccct     180

gtcaaagtga tcccatctca agctttcaga ggacttaatg aggtcataaa aattgaaatc     240

tctcagattg attccctgga aaggatagaa gctaatgcct ttgacaacct cctcaatttg     300

tctgaaatac tgatccagaa caccaaaaat ctgagataca ttgagcccgg agcatttata     360

aatcttcccg gattaaaata cttgagcatc tgtaacacag gcatcagaaa gtttccagat     420

gttacgaagg tcttctcctc tgaatcaaat ttcattctgg aaatttgtga taacttacac     480

ataaccacca taccaggaaa tgcttttcaa gggatgaata atgaatctgt aacactcaaa     540

ctatatggaa atggatttga agaagtacaa agtcatgcat tcaatgggac gacactgact     600

tcactggagc taaaggaaaa cgtacatctg gagaagatgc acaatggagc cttccgtggg     660

gccacagggc cgaaaacctt ggatatttct tccaccaaat tgcaggccct gccgagctat     720

ggcctagagt ccattcagag gctaattgcc acgtcatcct attctctaaa aaaattgcca     780

tcaagagaaa catttgtcaa tctcctggag gccacgttga cttaccccag ccactgctgt     840

gcttttagaa acttgccaac aaaagaacag aatttttcac attccatttc tgaaaacttt     900

tccaaacaat gtgaaagcac agtaaggaaa gtgagtaaca aaacacttta ttcttccatg     960

cttgctgaga gtgaactgag tggctgggac tatgaatatg gtttctgctt acccaagaca    1020

ccccgatgtg ctcctgaacc agatgctttt aatccctgtg aagacattat gggctatgac    1080

ttccttaggg tcctgatttg gctgattaat attctagcca tcatgggaaa catgactgtt    1140

ctttttgttc tcctgacaag tcgttacaaa cttacagtgc ctcgttttct catgtgcaat    1200

ctctcctttg cagacttttg catggggctc tatctgctgc tcatagcctc agttgattcc    1260

caaaccaagg gccagtacta taaccatgcc atagactggc agacagggag tgggtgcagc    1320

actgctggct tttcactgt attcgcaagt gaactttctg tctacaccct caccgtcatc    1380
```

-continued

```
actctagaaa gatggcacac catcacctat gctattcacc tggaccaaaa gctgcgatta   1440

agacatgcca ttctgattat gcttggagga tggctctttt cttctctaat tgctatgttg   1500

ccccttgtcg gtgtcagcaa ttacatgaag gtcagtattt gcttccccat ggatgtggaa   1560

accactctct cacaagtcta tatattaacc atcctgattc tcaatgtggt ggccttcttc   1620

ataatttgtg cttgctacat taaaatttat tttgcagttc gaaacccaga attaatggct   1680

accaataaag atacaaagat tgctaagaaa atggcaatcc tcatcttcac cgatttcacc   1740

tgcatggcac ctatctcttt ttttgccatc tcagctgcct tcaaagtacc tcttatcaca   1800

gtaaccaact ctaaagtttt actggttctt ttttatccca tcaattcttg tgccaatcca   1860

tttctgtatg caatattcac taagacattc caaagagatt tctttctttt gctgagcaaa   1920

tttggctgct gtaaacgtcg ggctgaactt tatagaagga aagatttttc agcttacacc   1980

tccaactgca aaaatggctt cactggatca aataagcctt ctcaatccac cttgaagttg   2040

tccacattgc actgtcaagg tacagctctc ctagacaaga ctcgctacac agagtgt      2097
```

```
<210> SEQ ID NO 11
<211> LENGTH: 868
<212> TYPE: PRT
<213> ORGANISM: Artificial Sequence
<220> FEATURE:
<223> OTHER INFORMATION: Description of Artificial Sequence:
      hLH-R-hCG-Beta Chimera 1

<400> SEQUENCE: 11

Met Lys Gln Arg Phe Ser Ala Leu Gln Leu Leu Lys Leu Leu Leu Leu
  1               5                  10                  15

Leu Gln Leu Gln Pro Pro Leu Pro Arg Ala Leu Arg Glu Ala Leu Cys
             20                  25                  30

Pro Glu Pro Cys Asn Cys Val Pro Asp Gly Ala Leu Arg Cys Pro Gly
         35                  40                  45

Pro Thr Ala Gly Leu Thr Arg Leu Ser Leu Ala Tyr Leu Pro Val Lys
     50                  55                  60

Val Ile Pro Ser Gln Ala Phe Arg Gly Leu Asn Glu Val Ile Lys Ile
 65                  70                  75                  80

Glu Ile Ser Gln Ile Asp Ser Leu Glu Arg Ile Glu Ala Asn Ala Phe
                 85                  90                  95

Asp Asn Leu Leu Asn Leu Ser Glu Ile Leu Ile Gln Asn Thr Lys Asn
            100                 105                 110

Leu Arg Tyr Ile Glu Pro Gly Ala Phe Ile Asn Leu Pro Arg Leu Lys
        115                 120                 125

Tyr Leu Ser Ile Cys Asn Thr Gly Ile Arg Lys Phe Pro Asp Val Thr
    130                 135                 140

Lys Val Phe Ser Ser Glu Ser Asn Phe Ile Leu Glu Ile Cys Asp Asn
145                 150                 155                 160

Leu His Ile Thr Thr Ile Pro Gly Asn Ala Phe Gln Gly Met Asn Asn
                165                 170                 175

Glu Ser Val Thr Leu Lys Leu Tyr Gly Asn Gly Phe Glu Glu Val Gln
            180                 185                 190

Ser His Ala Phe Asn Gly Thr Thr Leu Thr Ser Leu Glu Leu Lys Glu
        195                 200                 205

Asn Val His Leu Glu Lys Met His Asn Gly Ala Phe Arg Gly Ala Thr
    210                 215                 220

Gly Pro Lys Thr Leu Asp Ile Ser Ser Thr Lys Leu Gln Ala Leu Pro
225                 230                 235                 240
```

-continued

```
Ser Tyr Gly Leu Glu Ser Ile Gln Arg Leu Ile Ala Thr Ser Ser Tyr
                245                 250                 255

Ser Leu Lys Lys Leu Pro Ser Arg Glu Thr Phe Val Asn Leu Leu Glu
            260                 265                 270

Ala Thr Leu Thr Tyr Pro Ser His Cys Cys Ala Phe Arg Asn Leu Pro
        275                 280                 285

Thr Lys Glu Gln Asn Phe Ser His Ser Ile Ser Glu Asn Phe Ser Lys
    290                 295                 300

Gln Cys Glu Ser Thr Val Arg Lys Val Ser Asn Lys Thr Leu Tyr Ser
305                 310                 315                 320

Ser Met Leu Ala Glu Ser Glu Leu Ser Gly Trp Asp Tyr Glu Tyr Gly
                325                 330                 335

Phe Cys Leu Pro Lys Thr Pro Arg Cys Ala Pro Glu Pro Asp Ala Phe
            340                 345                 350

Asn Pro Cys Glu Asp Ile Met Gly Tyr Asp Phe Leu Arg Val Leu Ile
        355                 360                 365

Trp Leu Ile Asn Ile Leu Ala Ile Met Gly Asn Met Thr Val Leu Phe
    370                 375                 380

Val Leu Leu Thr Ser Arg Tyr Lys Leu Thr Val Pro Arg Phe Leu Met
385                 390                 395                 400

Cys Asn Leu Ser Phe Ala Asp Phe Cys Met Gly Leu Tyr Leu Leu Leu
                405                 410                 415

Ile Ala Ser Val Asp Ser Gln Thr Lys Gly Gln Tyr Tyr Asn His Ala
            420                 425                 430

Ile Asp Trp Gln Thr Gly Ser Gly Cys Ser Thr Ala Gly Phe Phe Thr
        435                 440                 445

Val Phe Ala Ser Glu Leu Ser Val Tyr Thr Leu Thr Val Ile Thr Leu
    450                 455                 460

Glu Arg Trp His Thr Ile Thr Tyr Ala Ile His Leu Asp Gln Lys Leu
465                 470                 475                 480

Arg Leu Arg His Ala Ile Leu Ile Met Leu Gly Gly Trp Leu Phe Ser
                485                 490                 495

Ser Leu Ile Ala Met Leu Pro Leu Val Gly Val Ser Asn Tyr Met Lys
            500                 505                 510

Val Ser Ile Cys Phe Pro Met Asp Val Glu Thr Thr Leu Ser Gln Val
        515                 520                 525

Tyr Ile Leu Thr Ile Leu Ile Leu Asn Val Val Ala Phe Phe Ile Ile
    530                 535                 540

Cys Ala Cys Tyr Ile Lys Ile Tyr Phe Ala Val Arg Asn Pro Glu Leu
545                 550                 555                 560

Met Ala Thr Asn Lys Asp Thr Lys Ile Ala Lys Lys Met Ala Ile Leu
                565                 570                 575

Ile Phe Thr Asp Phe Thr Cys Met Ala Pro Ile Ser Phe Phe Ala Ile
            580                 585                 590

Ser Ala Ala Phe Lys Val Pro Leu Ile Thr Val Thr Asn Ser Lys Val
        595                 600                 605

Leu Leu Val Leu Phe Tyr Pro Ile Asn Ser Cys Ala Asn Pro Phe Leu
    610                 615                 620

Tyr Ala Ile Phe Thr Lys Thr Phe Gln Arg Asp Phe Phe Leu Leu Leu
625                 630                 635                 640

Ser Lys Phe Gly Cys Cys Lys Arg Arg Ala Glu Leu Tyr Arg Arg Lys
                645                 650                 655
```

-continued

```
Asp Phe Ser Ala Tyr Thr Ser Asn Cys Lys Asn Gly Phe Thr Gly Ser
                660                 665                 670

Asn Lys Pro Ser Gln Ser Thr Leu Lys Leu Ser Thr Leu His Cys Gln
        675                 680                 685

Gly Thr Ala Leu Leu Asp Lys Thr Arg Tyr Thr Glu Cys Arg Ser Met
    690                 695                 700

Glu Met Phe Gln Gly Leu Leu Leu Leu Leu Leu Leu Ser Met Gly Gly
705                 710                 715                 720

Thr Trp Ala Ser Lys Glu Pro Leu Arg Pro Arg Cys Arg Pro Ile Asn
                725                 730                 735

Ala Thr Leu Ala Val Glu Lys Glu Gly Cys Pro Val Cys Ile Thr Val
            740                 745                 750

Asn Thr Thr Ile Cys Ala Gly Tyr Cys Pro Thr Met Thr Arg Val Leu
        755                 760                 765

Gln Gly Val Leu Pro Ala Leu Pro Gln Val Val Cys Asn Tyr Arg Asp
    770                 775                 780

Val Arg Phe Glu Ser Ile Arg Leu Pro Gly Cys Pro Arg Gly Val Asn
785                 790                 795                 800

Pro Val Val Ser Tyr Ala Val Ala Leu Ser Cys Gln Cys Ala Leu Cys
                805                 810                 815

Arg Arg Ser Thr Thr Asp Cys Gly Gly Pro Lys Asp His Pro Leu Thr
            820                 825                 830

Cys Asp Asp Pro Arg Phe Gln Asp Ser Ser Ser Ser Lys Ala Pro Pro
        835                 840                 845

Pro Ser Leu Pro Ser Pro Ser Arg Leu Pro Gly Pro Ser Asp Thr Pro
    850                 855                 860

Ile Leu Pro Gln
865
```

<210> SEQ ID NO 12
<211> LENGTH: 2604
<212> TYPE: DNA
<213> ORGANISM: Artificial Sequence
<220> FEATURE:
<223> OTHER INFORMATION: Description of Artificial Sequence:
hLH-R-hCG-Beta Chimera 1

<400> SEQUENCE: 12

```
atgaagcagc ggttctcggc gctgcagctg ctgaagctgc tgctgctgct gcagctgcag     60

ccgccgctgc cacgagcgct gcgcgaggcg ctctgccctg agccctgcaa ctgcgtgccc    120

gacggcgccc tgcgctgccc cggccccacg gccggtctca ctcgactatc acttgcctac    180

ctccctgtca aagtgatccc atctcaagct ttcagaggac ttaatgaggt cataaaaatt    240

gaaatctctc agattgattc cctggaaagg atagaagcta atgcctttga caacctcctc    300

aatttgtctg aaatactgat ccagaacacc aaaaatctga gatacattga gcccggagca    360

tttataaatc ttcccggatt aaaatacttg agcatctgta acacaggcat cagaaagttt    420

ccagatgtta cgaaggtctt ctcctctgaa tcaaatttca ttctggaaat ttgtgataac    480

ttacacataa ccaccatacc aggaaatgct tttcaaggga tgaataatga atctgtaaca    540

ctcaaactat atggaaatgg atttgaagaa gtacaaagtc atgcattcaa tgggacgaca    600

ctgacttcac tggagctaaa ggaaaacgta catctggaga agatgcacaa tggagccttc    660

cgtggggcca cagggccgaa aaccttggat atttcttcca ccaaattgca ggccctgccg    720

agctatggcc tagagtccat tcagaggcta attgccacgt catcctattc tctaaaaaaa    780
```

-continued

```
ttgccatcaa gagaaacatt tgtcaatctc ctggaggcca cgttgactta ccccagccac    840

tgctgtgctt ttagaaactt gccaacaaaa gaacagaatt tttcacattc catttctgaa    900

aacttttcca aacaatgtga aagcacagta aggaaagtga gtaacaaaac actttattct    960

tccatgcttg ctgagagtga actgagtggc tgggactatg aatatggttt ctgcttaccc   1020

aagacacccc gatgtgctcc tgaaccagat gcttttaatc cctgtgaaga cattatgggc   1080

tatgacttcc ttagggtcct gatttggctg attaatattc tagccatcat gggaaacatg   1140

actgttcttt ttgttctcct gacaagtcgt tacaaactta cagtgcctcg ttttctcatg   1200

tgcaatctct cctttgcaga cttttgcatg gggctctatc tgctgctcat agcctcagtt   1260

gattcccaaa ccaagggcca gtactataac catgccatag actggcagac agggagtggg   1320

tgcagcactg ctggcttttt cactgtattc gcaagtgaac tttctgtcta caccctcacc   1380

gtcatcactc tagaaagatg gcacaccatc acctatgcta ttcacctgga ccaaaagctg   1440

cgattaagac atgccattct gattatgctt ggaggatggc tcttttcttc tctaattgct   1500

atgttgcccc ttgtcggtgt cagcaattac atgaaggtca gtatttgctt ccccatggat   1560

gtggaaacca ctctctcaca agtctatata ttaaccatcc tgattctcaa tgtggtggcc   1620

ttcttcataa tttgtgcttg ctacattaaa atttattttg cagttcgaaa cccagaatta   1680

atggctacca ataaagatac aaagattgct aagaaaatgg caatcctcat cttcaccgat   1740

ttcacctgca tggcacctat ctcttttttt gccatctcag ctgccttcaa agtacctctt   1800

atcacagtaa ccaactctaa agttttactg gttctttttt atcccatcaa ttcttgtgcc   1860

aatccatttc tgtatgcaat attcactaag acattccaaa gagatttctt tcttttgctg   1920

agcaaatttg gctgctgtaa acgtcgggct gaactttata gaaggaaaga tttttcagct   1980

tacacctcca actgcaaaaa tggcttcact ggatcaaata agccttctca atccaccttg   2040

aagttgtcca cattgcactg tcaaggtaca gctctcctag acaagactcg ctacacagag   2100

tgtagatcta tggagatgtt ccaggggctg ctgctgttgc tgctgctgag catgggcggg   2160

acatgggcat ccaaggagcc gcttcggcca cggtgccgcc ccatcaatgc caccctggct   2220

gtggagaagg agggctgccc cgtgtgcatc accgtcaaca ccaccatctg tgccggctac   2280

tgccccacca tgacccgcgt gctgcagggg gtcctgccgg ccctgcctca ggtggtgtgc   2340

aactaccgcg atgtgcgctt cgagtccatc cggctccctg gctgcccgcg cggcgtgaac   2400

cccgtggtct cctacgccgt ggctctcagc tgtcaatgtg cactctgccg ccgcagcacc   2460

actgactgcg gggtcccaa ggaccacccc ttgacctgtg atgacccccg cttccaggac   2520

tcctcttcct caaaggcccc tccccccagc cttccaagtc catcccgact cccggggccc   2580

tcggacaccc cgatcctccc acaa                                          2604
```

<210> SEQ ID NO 13
<211> LENGTH: 739
<212> TYPE: PRT
<213> ORGANISM: Artificial Sequence
<220> FEATURE:
<223> OTHER INFORMATION: Description of Artificial Sequence:
hLH-R-hCG-Beta Chimera 2

<400> SEQUENCE: 13

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30
```

-continued

```
Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445

Ala Ser Glu Leu Ser Val Tyr Thr Leu Thr Val Ile Thr Leu Glu Arg
```

-continued

```
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys Gly Thr Leu Thr Cys
    690                 695                 700

Asp Asp Pro Arg Phe Gln Asp Ser Ser Ser Ser Lys Ala Pro Pro Pro
705                 710                 715                 720

Ser Leu Pro Ser Pro Ser Arg Leu Pro Gly Pro Ser Asp Thr Pro Ile
                725                 730                 735

Leu Pro Gln


<210> SEQ ID NO 14
<211> LENGTH: 2217
<212> TYPE: DNA
<213> ORGANISM: Artificial Sequence
<220> FEATURE:
<223> OTHER INFORMATION: Description of Artificial Sequence:
      hLH-R-hCG-Beta Chimera 2

<400> SEQUENCE: 14

atgaagcagc ggttctcggc gctgcagctg ctgaagctgc tgctgctgct gcagccgccg      60

ctgccacgag cgctgcgcga ggcgctctgc cctgagccct gcaactgcgt gcccgacggc     120

gccctgcgct gccccggccc cacggccggt ctcactcgac tatcacttgc ctacctccct     180

gtcaaagtga tcccatctca agctttcaga ggacttaatg aggtcataaa aattgaaatc     240

tctcagattg attccctgga aaggatagaa gctaatgcct ttgacaacct cctcaatttg     300

tctgaaatac tgatccagaa caccaaaaat ctgagataca ttgagcccgg agcatttata     360

aatcttcccg gattaaaata cttgagcatc tgtaacacag gcatcagaaa gtttccagat     420
```

-continued

```
gttacgaagg tcttctcctc tgaatcaaat ttcattctgg aaatttgtga taacttacac    480
ataaccacca taccaggaaa tgcttttcaa gggatgaata atgaatctgt aacactcaaa    540
ctatatggaa atggatttga agaagtacaa agtcatgcat tcaatgggac gacactgact    600
tcactggagc taaaggaaaa cgtacatctg gagaagatgc acaatggagc cttccgtggg    660
gccacagggc cgaaaacctt ggatatttct tccaccaaat tgcaggccct gccgagctat    720
ggcctagagt ccattcagag gctaattgcc acgtcatcct attctctaaa aaaattgcca    780
tcaagagaaa catttgtcaa tctcctggag gccacgttga cttaccccag ccactgctgt    840
gcttttagaa acttgccaac aaaagaacag aatttttcac attccatttc tgaaaacttt    900
tccaaacaat gtgaaagcac agtaaggaaa gtgagtaaca aaacacttta ttcttccatg    960
cttgctgaga gtgaactgag tggctgggac tatgaatatg gtttctgctt acccaagaca   1020
ccccgatgtg ctcctgaacc agatgctttt aatccctgtg aagacattat gggctatgac   1080
ttccttaggg tcctgatttg gctgattaat attctagcca tcatgggaaa catgactgtt   1140
ctttttgttc tcctgacaag tcgttacaaa cttacagtgc ctcgttttct catgtgcaat   1200
ctctcctttg cagacttttg catggggctc tatctgctgc tcatagcctc agttgattcc   1260
caaaccaagg gccagtacta taaccatgcc atagactggc agacagggag tgggtgcagc   1320
actgctggct tttcactgt attcgcaagt gaactttctg tctacaccct caccgtcatc   1380
actctagaaa gatggcacac catcacctat gctattcacc tggaccaaaa gctgcgatta   1440
agacatgcca ttctgattat gcttggagga tggctctttt cttctctaat tgctatgttg   1500
ccccttgtcg gtgtcagcaa ttacatgaag gtcagtattt gcttccccat ggatgtggaa   1560
accactctct cacaagtcta tatattaacc atcctgattc tcaatgtggt ggccttcttc   1620
ataatttgtg cttgctacat taaaatttat tttgcagttc gaaacccaga attaatggct   1680
accaataaag atacaaagat tgctaagaaa atggcaatcc tcatcttcac cgatttcacc   1740
tgcatggcac ctatctcttt ttttgccatc tcagctgcct tcaaagtacc tcttatcaca   1800
gtaaccaact ctaaagtttt actggttctt ttttatccca tcaattcttg tgccaatcca   1860
tttctgtatg caatattcac taagacattc caaagagatt tctttctttt gctgagcaaa   1920
tttggctgct gtaaacgtcg ggctgaactt tatagaagga aagatttttc agcttacacc   1980
tccaactgca aaaatggctt cactggatca aataagcctt ctcaatccac cttgaagttg   2040
tccacattgc actgtcaagg tacagctctc ctagacaaga ctcgctacac agagtgtggt   2100
accttgacct gtgatgaccc ccgcttccag gactcctctt cctcaaaggc ccctcccccc   2160
agccttccaa gtccatcccg actcccgggg ccctcggaca ccccgatcct cccacaa      2217
```

<210> SEQ ID NO 15
<211> LENGTH: 387
<212> TYPE: PRT
<213> ORGANISM: Artificial Sequence
<220> FEATURE:
<223> OTHER INFORMATION: Description of Artificial Sequence:
      hLH-R-hCG-Beta Chimera 3

<400> SEQUENCE: 15

```
Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
```

-continued

```
        35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Gly Thr Leu Thr Cys
            340                 345                 350

Asp Asp Pro Arg Phe Gln Asp Ser Ser Ser Ser Lys Ala Pro Pro Pro
        355                 360                 365

Ser Leu Pro Ser Pro Ser Arg Leu Pro Gly Pro Ser Asp Thr Pro Ile
    370                 375                 380

Leu Pro Gln
385
```

<210> SEQ ID NO 16
<211> LENGTH: 1161
<212> TYPE: DNA
<213> ORGANISM: Artificial Sequence
<220> FEATURE:
<223> OTHER INFORMATION: Description of Artificial Sequence:
      hLH-R-hCG-Beta Chimera 3

<400> SEQUENCE: 16

-continued

```
atgaagcagc ggttctcggc gctgcagctg ctgaagctgc tgctgctgct gcagccgccg      60

ctgccacgag cgctgcgcga ggcgctctgc cctgagccct gcaactgcgt gcccgacggc     120

gccctgcgct gccccggccc cacggccggt ctcactcgac tatcacttgc ctacctccct     180

gtcaaagtga tcccatctca agctttcaga ggacttaatg aggtcataaa aattgaaatc     240

tctcagattg attccctgga aaggatagaa gctaatgcct ttgacaacct cctcaatttg     300

tctgaaatac tgatccagaa caccaaaaat ctgagataca ttgagcccgg agcatttata     360

aatcttcccg gattaaaata cttgagcatc tgtaacacag gcatcagaaa gtttccagat     420

gttacgaagg tcttctcctc tgaatcaaat ttcattctgg aaatttgtga taacttacac     480

ataaccacca taccaggaaa tgcttttcaa gggatgaata atgaatctgt aacactcaaa     540

ctatatggaa atggatttga agaagtacaa agtcatgcat tcaatgggac gacactgact     600

tcactggagc taaaggaaaa cgtacatctg gagaagatgc acaatggagc cttccgtggg     660

gccacagggc cgaaaacctt ggatatttct tccaccaaat tgcaggccct gccgagctat     720

ggcctagagt ccattcagag gctaattgcc acgtcatcct attctctaaa aaaattgcca     780

tcaagagaaa catttgtcaa tctcctggag gccacgttga cttaccccag ccactgctgt     840

gcttttagaa acttgccaac aaaagaacag aatttttcac attccatttc tgaaaacttt     900

tccaaacaat gtgaaagcac agtaaggaaa gtgagtaaca aaacacttta ttcttccatg     960

cttgctgaga gtgaactgag tggctgggac tatgaatatg gtttctgctt acccaagaca    1020

ccccgatgtg ctcctgaacc aggtaccttg acctgtgatg acccccgctt ccaggactcc    1080

tcttcctcaa aggcccctcc ccccagcctt ccaagtccat cccgactccc ggggccctcg    1140

gacaccccga tcctcccaca a                                              1161


<210> SEQ ID NO 17
<211> LENGTH: 514
<212> TYPE: PRT
<213> ORGANISM: Artificial Sequence
<220> FEATURE:
<223> OTHER INFORMATION: Description of Artificial Sequence:
      hLH-R-hCG-Beta Chimera 4

<400> SEQUENCE: 17

Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
```

-continued

```
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Gly Thr Met Glu Met
            340                 345                 350

Phe Gln Gly Leu Leu Leu Leu Leu Leu Leu Ser Met Gly Gly Thr Trp
        355                 360                 365

Ala Ser Lys Glu Pro Leu Arg Pro Arg Cys Arg Pro Ile Asn Ala Thr
    370                 375                 380

Leu Ala Val Glu Lys Glu Gly Cys Pro Val Cys Ile Thr Val Asn Thr
385                 390                 395                 400

Thr Ile Cys Ala Gly Tyr Cys Pro Thr Met Thr Arg Val Leu Gln Gly
                405                 410                 415

Val Leu Pro Ala Leu Pro Gln Val Val Cys Asn Tyr Arg Asp Val Arg
            420                 425                 430

Phe Glu Ser Ile Arg Leu Pro Gly Cys Pro Arg Gly Val Asn Pro Val
        435                 440                 445

Val Ser Tyr Ala Val Ala Leu Ser Cys Gln Cys Ala Leu Cys Arg Arg
    450                 455                 460

Ser Thr Thr Asp Cys Gly Gly Pro Lys Asp His Pro Leu Thr Cys Asp
465                 470                 475                 480

Asp Pro Arg Phe Gln Asp Ser Ser Ser Ser Lys Ala Pro Pro Pro Ser
                485                 490                 495

Leu Pro Ser Pro Ser Arg Leu Pro Gly Pro Ser Asp Thr Pro Ile Leu
            500                 505                 510

Pro Gln


<210> SEQ ID NO 18
<211> LENGTH: 1542
<212> TYPE: DNA
<213> ORGANISM: Artificial Sequence
<220> FEATURE:
<223> OTHER INFORMATION: Description of Artificial Sequence:
      hLH-R-hCG-Beta Chimera 4
```

-continued

<400> SEQUENCE: 18

```
atgaagcagc ggttctcggc gctgcagctg ctgaagctgc tgctgctgct gcagccgccg      60
ctgccacgag cgctgcgcga ggcgctctgc cctgagccct gcaactgcgt gcccgacggc     120
gccctgcgct gccccggccc cacggccggt ctcactcgac tatcacttgc ctacctccct     180
gtcaaagtga tcccatctca agctttcaga ggacttaatg aggtcataaa aattgaaatc     240
tctcagattg attccctgga aaggatagaa gctaatgcct ttgacaacct cctcaatttg     300
tctgaaatac tgatccagaa caccaaaaat ctgagataca ttgagcccgg agcatttata     360
aatcttcccg gattaaaata cttgagcatc tgtaacacag gcatcagaaa gtttccagat     420
gttacgaagg tcttctcctc tgaatcaaat ttcattctgg aaatttgtga taacttacac     480
ataaccacca taccaggaaa tgcttttcaa gggatgaata atgaatctgt aacactcaaa     540
ctatatggaa atggatttga agaagtacaa agtcatgcat tcaatgggac gacactgact     600
tcactggagc taaaggaaaa cgtacatctg gagaagatgc acaatggagc cttccgtggg     660
gccacagggc cgaaaacctt ggatatttct tccaccaaat tgcaggccct gccgagctat     720
ggcctagagt ccattcagag gctaattgcc acgtcatcct attctctaaa aaaattgcca     780
tcaagagaaa catttgtcaa tctcctggag gccacgttga cttaccccag ccactgctgt     840
gcttttagaa acttgccaac aaaagaacag aatttttcac attccatttc tgaaaacttt     900
tccaaacaat gtgaaagcac agtaaggaaa gtgagtaaca aaacacttta ttcttccatg     960
cttgctgaga gtgaactgag tggctgggac tatgaatatg gtttctgctt acccaagaca    1020
ccccgatgtg ctcctgaacc aggtaccatg gagatgttcc aggggctgct gctgttgctg    1080
ctgctgagca tgggcgggac atgggcatcc aaggagccgc ttcggccacg gtgccgcccc    1140
atcaatgcca ccctggctgt ggagaaggag ggctgccccg tgtgcatcac cgtcaacacc    1200
accatctgtg ccggctactg ccccaccatg acccgcgtgc tgcagggggt cctgccggcc    1260
ctgcctcagg tggtgtgcaa ctaccgcgat gtgcgcttcg agtccatccg gctccctggc    1320
tgcccgcgcg gcgtgaaccc cgtggtctcc tacgccgtgg ctctcagctg tcaatgtgca    1380
ctctgccgcc gcagcaccac tgactgcggg ggtcccaagg accacccctt gacctgtgat    1440
gacccccgct tccaggactc ctcttcctca aaggcccctc cccccagcct tccaagtcca    1500
tcccgactcc cggggccctc ggacaccccg atcctcccac aa                       1542
```